US008814860B2

(12) United States Patent
Davalos et al.

(10) Patent No.: US 8,814,860 B2
(45) Date of Patent: Aug. 26, 2014

(54) IRREVERSIBLE ELECTROPORATION USING NANOPARTICLES

(71) Applicant: Virginia Tech Intellectual Properties, Inc., Blacksburg, VA (US)

(72) Inventors: Rafael V. Davalos, Blacksburg, VA (US); Marissa N. Rylander, Blacksburg, VA (US); Christopher B. Arena, Burlington, NC (US); Yong Woo Lee, Blacksburg, VA (US)

(73) Assignee: Virginia Tech Intellectual Properties, Inc., Blacksburg, VA (US)

( * ) Notice: Subject to any disclaimer, the term of this patent is extended or adjusted under 35 U.S.C. 154(b) by 0 days.

(21) Appl. No.: 13/919,640

(22) Filed: Jun. 17, 2013

(65) Prior Publication Data
US 2013/0281968 A1 Oct. 24, 2013

Related U.S. Application Data

(63) Continuation of application No. 12/609,779, filed on Oct. 30, 2009, now Pat. No. 8,465,484, which is a continuation-in-part of application No. 12/491,151, filed on Jun. 24, 2009, which is a continuation-in-part of application No. 12/432,295, filed on Apr. 29, 2009.

(60) Provisional application No. 61/125,840, filed on Apr. 29, 2008, provisional application No. 61/171,564, filed on Apr. 22, 2009, provisional application No. 61/167,997, filed on Apr. 9, 2009, provisional application No. 61/075,216, filed on Jun. 24, 2008.

(51) Int. Cl.
*A61B 18/18* (2006.01)
*A61N 1/32* (2006.01)
*C12N 13/00* (2006.01)
*A61N 1/05* (2006.01)

(52) U.S. Cl.
CPC . *A61N 1/327* (2013.01); *A61N 1/05* (2013.01); *C12N 13/00* (2013.01)
USPC ................................ 606/41; 607/116; 604/20

(58) Field of Classification Search
USPC .............. 606/27–37, 41, 42, 48–50; 607/101, 607/102, 116; 128/898; 604/20–22
See application file for complete search history.

(56) References Cited

U.S. PATENT DOCUMENTS 1,653,819 A   12/1927   Northcott et al.
4,016,886 A   4/1977   Doss et al.
(Continued)

FOREIGN PATENT DOCUMENTS

DE   863111tr   1/1953
DE   4000893tr   7/1991
(Continued)

OTHER PUBLICATIONS

Co-Pending U.S. Appl. No. 12/491,151, filed Jun. 24, 2009.
(Continued)

*Primary Examiner* — Linda Dvorak
*Assistant Examiner* — Jocelyn D Ram
(74) *Attorney, Agent, or Firm* — New River Valley IP Law, PC; Michele L. Mayberry

(57) ABSTRACT

The present invention provides methods, devices, and systems for in vivo treatment of cell proliferative disorders. The invention can be used to treat solid tumors, such as brain tumors. The methods rely on non-thermal irreversible electroporation (IRE) to cause cell death in treated tumors. In embodiments, the methods comprise the use of high aspect ratio nanoparticles with or without modified surface chemistry.

16 Claims, 28 Drawing Sheets

(56) References Cited

U.S. PATENT DOCUMENTS

| | | | |
|---|---|---|---|
| 4,226,246 A | 10/1980 | Fragnet | |
| 4,262,672 A | 4/1981 | Kief | |
| 4,407,943 A | 10/1983 | Cole et al. | |
| 4,416,276 A | 11/1983 | Newton et al. | |
| 4,810,963 A | 3/1989 | Blake-Coleman et al. | |
| 4,907,601 A | 3/1990 | Frick | |
| 4,946,793 A | 8/1990 | Marshall, III | |
| 5,019,034 A | 5/1991 | Weaver et al. | |
| 5,052,391 A | 10/1991 | Silberstone et al. | |
| 5,058,605 A | 10/1991 | Slovak | |
| 5,098,843 A | 3/1992 | Calvin | |
| 5,134,070 A | 7/1992 | Casnig | |
| 5,173,158 A | 12/1992 | Schmukler | |
| 5,192,312 A | 3/1993 | Orton | |
| 5,193,537 A | 3/1993 | Freeman | |
| 5,273,525 A | 12/1993 | Hofmann | |
| 5,283,194 A | 2/1994 | Schmukler | |
| 5,318,563 A | 6/1994 | Malis et al. | |
| 5,328,451 A | 7/1994 | Davis et al. | |
| 5,389,069 A | 2/1995 | Weaver | |
| 5,403,311 A | 4/1995 | Abele et al. | |
| 5,425,752 A | 6/1995 | Vu Nguyen | |
| 5,439,440 A | 8/1995 | Hofmann | |
| 5,458,625 A | 10/1995 | Kendall | |
| 5,533,999 A | 7/1996 | Hood et al. | |
| 5,536,240 A | 7/1996 | Edwards et al. | |
| 5,575,811 A | 11/1996 | Reid et al. | |
| 5,626,146 A | 5/1997 | Barber et al. | |
| 5,634,899 A | 6/1997 | Shapland et al. | |
| 5,674,267 A | 10/1997 | Mir et al. | |
| 5,702,359 A | 12/1997 | Hofmann et al. | |
| 5,718,246 A | 2/1998 | Vona | |
| 5,720,921 A | 2/1998 | Meserol | |
| 5,778,894 A | 7/1998 | Dorogi et al. | |
| 5,782,882 A | 7/1998 | Lerman et al. | |
| 5,800,378 A | 9/1998 | Edwards et al. | |
| 5,810,762 A | 9/1998 | Hofmann | |
| 5,836,905 A | 11/1998 | Lemelson et al. | |
| 5,843,026 A | 12/1998 | Edwards et al. | |
| 5,843,182 A | 12/1998 | Goldstein | |
| 5,873,849 A | 2/1999 | Bernard | |
| 5,919,142 A | 7/1999 | Boone et al. | |
| 5,947,889 A | 9/1999 | Hehrlein | |
| 5,983,131 A | 11/1999 | Weaver et al. | |
| 5,991,697 A | 11/1999 | Nelson et al. | |
| 5,999,847 A | 12/1999 | Elstrom | |
| 6,009,347 A | 12/1999 | Hofmann | |
| 6,010,613 A | 1/2000 | Walters et al. | |
| 6,016,452 A | 1/2000 | Kasevich | |
| 6,041,252 A | 3/2000 | Walker et al. | |
| 6,055,453 A | 4/2000 | Hofmann et al. | |
| 6,068,650 A * | 5/2000 | Hofmann et al. | 607/2 |
| 6,085,115 A | 7/2000 | Weaver et al. | |
| 6,090,106 A | 7/2000 | Goble et al. | |
| 6,102,885 A | 8/2000 | Bass | |
| 6,106,521 A | 8/2000 | Blewett et al. | |
| 6,109,270 A | 8/2000 | Mah et al. | |
| 6,122,599 A | 9/2000 | Mehta | |
| 6,132,419 A | 10/2000 | Hofmann | |
| 6,159,163 A | 12/2000 | Strauss et al. | |
| 6,208,893 B1 | 3/2001 | Hofmann | |
| 6,210,402 B1 | 4/2001 | Olsen et al. | |
| 6,212,433 B1 | 4/2001 | Behl | |
| 6,216,034 B1 | 4/2001 | Hofmann et al. | |
| 6,219,577 B1 | 4/2001 | Brown, III et al. | |
| 6,241,702 B1 | 6/2001 | Lundquist et al. | |
| 6,241,725 B1 | 6/2001 | Cosman | |
| 6,261,831 B1 | 7/2001 | Agee | |
| 6,278,895 B1 | 8/2001 | Bernard | |
| 6,287,293 B1 | 9/2001 | Jones et al. | |
| 6,300,108 B1 | 10/2001 | Rubinsky et al. | |
| 6,326,177 B1 | 12/2001 | Schoenbach et al. | |
| 6,347,247 B1 | 2/2002 | Dev et al. | |
| 6,349,233 B1 | 2/2002 | Adams | |
| 6,351,674 B2 | 2/2002 | Silverstone | |
| 6,387,671 B1 | 5/2002 | Rubinsky et al. | |
| 6,403,348 B1 | 6/2002 | Rubinsky et al. | |
| 6,470,211 B1 | 10/2002 | Ideker et al. | |
| 6,482,619 B1 | 11/2002 | Rubinsky et al. | |
| 6,493,592 B1 | 12/2002 | Leonard et al. | |
| 6,500,173 B2 | 12/2002 | Underwood et al. | |
| 6,526,320 B2 | 2/2003 | Mitchell | |
| 6,562,604 B2 | 5/2003 | Rubinsky et al. | |
| 6,607,529 B1 | 8/2003 | Jones et al. | |
| 6,611,706 B2 | 8/2003 | Avrahami et al. | |
| 6,613,211 B1 | 9/2003 | Mccormick et al. | |
| 6,627,421 B1 | 9/2003 | Unger et al. | |
| 6,653,091 B1 | 11/2003 | Dunn et al. | |
| 6,669,691 B1 | 12/2003 | Taimisto | |
| 6,692,493 B2 | 2/2004 | Mcgovern et al. | |
| 6,697,669 B2 | 2/2004 | Dev et al. | |
| 6,697,670 B2 | 2/2004 | Chomenky et al. | |
| 6,702,808 B1 | 3/2004 | Kreindel | |
| 6,795,728 B2 | 9/2004 | Chornenky et al. | |
| 6,801,804 B2 | 10/2004 | Miller et al. | |
| 6,865,416 B2 | 3/2005 | Dev et al. | |
| 6,892,099 B2 | 5/2005 | Jaafar et al. | |
| 6,912,417 B1 | 6/2005 | Bernard et al. | |
| 6,927,049 B2 | 8/2005 | Rubinsky et al. | |
| 6,962,587 B2 | 11/2005 | Johnson et al. | |
| 6,972,014 B2 | 12/2005 | Eum et al. | |
| 6,994,706 B2 | 2/2006 | Chornenky et al. | |
| 7,053,063 B2 | 5/2006 | Rubinsky et al. | |
| 7,054,685 B2 | 5/2006 | Dimmer et al. | |
| 7,063,698 B2 | 6/2006 | Whayne et al. | |
| 7,113,821 B1 | 9/2006 | Sun et al. | |
| 7,130,697 B2 | 10/2006 | Chornenky et al. | |
| 7,211,083 B2 | 5/2007 | Chornenky et al. | |
| 7,267,676 B2 | 9/2007 | Chornenky et al. | |
| 7,291,146 B2 | 11/2007 | Steinke et al. | |
| 7,344,533 B2 | 3/2008 | Pearson et al. | |
| 7,655,004 B2 | 2/2010 | Long | |
| 7,680,543 B2 | 3/2010 | Azure | |
| 7,742,795 B2 | 6/2010 | Stone et al. | |
| 8,048,067 B2 * | 11/2011 | Davalos et al. | 606/32 |
| 8,282,631 B2 | 10/2012 | Davalos et al. | |
| 8,465,484 B2 | 6/2013 | Davalos et al. | |
| 2001/0044596 A1 | 11/2001 | Jaafar | |
| 2002/0010491 A1 | 1/2002 | Schoenbach et al. | |
| 2002/0055731 A1 | 5/2002 | Atala et al. | |
| 2002/0077676 A1 | 6/2002 | Schroeppel et al. | |
| 2002/0099323 A1 | 7/2002 | Dev et al. | |
| 2002/0115208 A1 | 8/2002 | Mitchell et al. | |
| 2002/0119437 A1 | 8/2002 | Grooms et al. | |
| 2002/0138117 A1 | 9/2002 | Son | |
| 2002/0183684 A1 | 12/2002 | Dev et al. | |
| 2002/0193831 A1 | 12/2002 | Smith | |
| 2003/0009110 A1 | 1/2003 | Tu et al. | |
| 2003/0060856 A1 | 3/2003 | Chornenky et al. | |
| 2003/0088189 A1 | 5/2003 | Tu et al. | |
| 2003/0096407 A1 | 5/2003 | Atala et al. | |
| 2003/0130711 A1 | 7/2003 | Pearson et al. | |
| 2003/0170898 A1 | 9/2003 | Gundersen et al. | |
| 2003/0199050 A1 | 10/2003 | Mangano et al. | |
| 2003/0208200 A1 | 11/2003 | Palanker et al. | |
| 2003/0225360 A1 | 12/2003 | Eppstein et al. | |
| 2004/0009459 A1 | 1/2004 | Anderson et al. | |
| 2004/0019371 A1 | 1/2004 | Jaafar et al. | |
| 2004/0059389 A1 | 3/2004 | Chornenky et al. | |
| 2004/0146877 A1 | 7/2004 | Diss et al. | |
| 2004/0153057 A1 | 8/2004 | Davison | |
| 2004/0176855 A1 | 9/2004 | Badylak | |
| 2004/0193097 A1 * | 9/2004 | Hofmann et al. | 604/20 |
| 2004/0236376 A1 | 11/2004 | Miklavcic et al. | |
| 2004/0243107 A1 | 12/2004 | Macoviak et al. | |
| 2004/0267189 A1 | 12/2004 | Mavor et al. | |
| 2005/0013870 A1 | 1/2005 | Freyman et al. | |
| 2005/0043726 A1 | 2/2005 | Mchale et al. | |
| 2005/0049541 A1 | 3/2005 | Behar et al. | |
| 2005/0165393 A1 * | 7/2005 | Eppstein | 606/41 |
| 2005/0171523 A1 | 8/2005 | Rubinsky et al. | |
| 2005/0171574 A1 | 8/2005 | Rubinsky et al. | |
| 2005/0182462 A1 | 8/2005 | Chornenky et al. | |
| 2005/0261672 A1 | 11/2005 | Deem et al. | |

(56) References Cited

U.S. PATENT DOCUMENTS

| | | |
|---|---|---|
| 2005/0288730 A1 | 12/2005 | Deem et al. |
| 2006/0015147 A1 | 1/2006 | Persson et al. |
| 2006/0024359 A1 | 2/2006 | Walker et al. |
| 2006/0025760 A1 | 2/2006 | Podhajsky |
| 2006/0079883 A1 | 4/2006 | Elmouelhi et al. |
| 2006/0121610 A1 | 6/2006 | Rubinsky et al. |
| 2006/0142801 A1 | 6/2006 | Demarais et al. |
| 2006/0212078 A1 | 9/2006 | Demarais et al. |
| 2006/0217703 A1 | 9/2006 | Chornenky et al. |
| 2006/0235474 A1 | 10/2006 | Demarais |
| 2006/0264752 A1 | 11/2006 | Rubinsky et al. |
| 2006/0264807 A1 | 11/2006 | Westersten et al. |
| 2006/0269531 A1 | 11/2006 | Beebe et al. |
| 2006/0293713 A1 | 12/2006 | Rubinsky et al. |
| 2006/0293725 A1 | 12/2006 | Rubinsky et al. |
| 2006/0293731 A1* | 12/2006 | Rubinsky et al. .............. 607/98 |
| 2007/0021803 A1 | 1/2007 | Deem et al. |
| 2007/0025919 A1 | 2/2007 | Deem et al. |
| 2007/0043345 A1 | 2/2007 | Davalos et al. |
| 2007/0060989 A1 | 3/2007 | Deem et al. |
| 2007/0118069 A1 | 5/2007 | Persson et al. |
| 2007/0230757 A1 | 10/2007 | Trachtenberg et al. |
| 2007/0287950 A1* | 12/2007 | Kjeken et al. .................. 604/21 |
| 2008/0015571 A1 | 1/2008 | Rubinsky et al. |
| 2008/0033340 A1 | 2/2008 | Heller et al. |
| 2008/0033417 A1 | 2/2008 | Nields et al. |
| 2008/0045880 A1 | 2/2008 | Kjeken et al. |
| 2008/0052786 A1 | 2/2008 | Lin et al. |
| 2008/0071262 A1 | 3/2008 | Azure |
| 2008/0097422 A1 | 4/2008 | Edwards et al. |
| 2008/0103529 A1 | 5/2008 | Schoenbach et al. |
| 2008/0200912 A1 | 8/2008 | Long |
| 2009/0024075 A1 | 1/2009 | Schroeppel et al. |
| 2009/0198231 A1* | 8/2009 | Esser et al. ..................... 606/41 |
| 2009/0247933 A1 | 10/2009 | Maor et al. |
| 2009/0248012 A1 | 10/2009 | Maor et al. |
| 2009/0269317 A1* | 10/2009 | Davalos ..................... 424/93.7 |
| 2009/0281477 A1* | 11/2009 | Mikus et al. .................. 604/21 |
| 2009/0292342 A1 | 11/2009 | Rubinsky et al. |
| 2009/0318905 A1 | 12/2009 | Bhargav et al. |
| 2010/0023004 A1 | 1/2010 | Francischelli et al. |
| 2010/0030211 A1* | 2/2010 | Davalos et al. ................ 606/41 |
| 2010/0049190 A1 | 2/2010 | Long et al. |
| 2010/0087813 A1 | 4/2010 | Long |
| 2010/0130975 A1 | 5/2010 | Long |
| 2010/0152725 A1 | 6/2010 | Pearson et al. |
| 2010/0160850 A1 | 6/2010 | Ivorra et al. |
| 2010/0179530 A1 | 7/2010 | Long et al. |
| 2010/0204560 A1 | 8/2010 | Salahieh et al. |
| 2010/0204638 A1 | 8/2010 | Hobbs et al. |
| 2010/0249771 A1 | 9/2010 | Pearson et al. |
| 2010/0250209 A1 | 9/2010 | Pearson et al. |
| 2010/0256630 A1 | 10/2010 | Hamilton, Jr. et al. |
| 2010/0261994 A1* | 10/2010 | Davalos et al. .............. 600/411 |
| 2010/0331758 A1* | 12/2010 | Davalos et al. ................ 604/20 |
| 2011/0106221 A1 | 5/2011 | Neal, II et al. |
| 2012/0071874 A1 | 3/2012 | Davalos et al. |
| 2012/0089009 A1* | 4/2012 | Omary et al. ................. 600/411 |
| 2012/0109122 A1 | 5/2012 | Arena et al. |
| 2013/0090646 A1* | 4/2013 | Moss et al. ..................... 606/41 |
| 2013/0108667 A1* | 5/2013 | Soikum et al. ................ 424/400 |
| 2013/0184702 A1 | 7/2013 | Neal, II et al. |
| 2013/0253415 A1 | 9/2013 | Sano et al. |

FOREIGN PATENT DOCUMENTS

| | | |
|---|---|---|
| EP | 0378132 A | 7/1990 |
| EP | 0935482 B1 | 5/2005 |
| WO | 9639531 A | 12/1996 |
| WO | 9814238 A | 4/1998 |
| WO | 0020554 A | 4/2000 |
| WO | 0107583 A | 2/2001 |
| WO | 0107584 A | 2/2001 |
| WO | 0107585 A | 2/2001 |
| WO | 0110319 A | 2/2001 |
| WO | 0148153 A | 7/2001 |
| WO | 0181533 A | 11/2001 |
| WO | 02078527 A | 10/2002 |
| WO | 02089686 A | 11/2002 |
| WO | 02100459 A | 12/2002 |
| WO | 03099382 A | 12/2003 |
| WO | 2004037341 A2 | 5/2004 |
| WO | 2005065284 A | 7/2005 |
| WO | 2009134876 A | 11/2009 |
| WO | 2010117806 A1 | 10/2010 |
| WO | 2010118387 A1 | 10/2010 |
| WO | 2010151277 A | 12/2010 |
| WO | 2011047387 A | 4/2011 |
| WO | 2012071526 A | 5/2012 |
| WO | 2012088149 A | 6/2012 |

OTHER PUBLICATIONS

Co-Pending U.S. Appl. No. 13/332,133, filed Dec. 20, 2011.
Co-Pending U.S. Appl. No. 13/550,307, filed Jul. 16, 2012.
Co-Pending U.S. Appl. No. 13/958,152, filed Aug. 2, 2013.
Co-Pending U.S. Appl. No. 13/969,175, filed May 23, 2013.
Co-Pending U.S. Appl. No. 14/012,832, filed Aug. 28, 2013.
Co-Pending U.S. Appl. No. 14/017,210, filed Sep. 3, 2013.
Co-pending European Application No. 10 824 248.8, Invitation Pursuant to rule 62a(1) EPC (Sep. 25, 2013).
Cowley, Good News for Boomers, Newsweek, Dec. 30, 1996/Jan. 6, 1997.
Cox, et al., Surgical Treatment of Atrial Fibrillation: A Review, Europace (2004) 5, S20-S-29.
Crowley, Electrical Breakdown of Biomolecular Lipid Membranes as an Electromechanical Instability, Biophysical Journal, vol. 13, pp. 711-724, 1973.
Davalos et al., Theoretical Analysis of the Thermal Effects During In Vivo Tissue Electroporation, Bioelectrochemistry, vol. 61, pp. 99-107, 2003.
Davalos, et al., A Feasibility Study of Electrical Impedance Tomography as a Means to Monitor Tissue Electroporation for Molecular Medicine, IEEE Transactions on Biomedical Engineering, vol. 49, No. 4, Apr. 2002.
Davalos, et al., Tissue Ablation with Irreversible Electroporation, Annals of Biomedical Engineering, vol. 33, No. 2, p. 223-231, Feb. 2005.
Davalos, R. V. & Rubinsky, B. Temperature considerations during irreversible electroporation. International Journal of Heat and Mass Transfer 51, 5617-5622, doi:10.1016/j.ijheatmasstransfer.2008.04.046 (2008).
Davalos, Real-Time Imaging for Molecular Medicine through Electrical Impedance Tomography of Electroporation, Dissertation for Ph.D. in Engineering-Mechanical Engineering, Graduate Division of University of California, Berkeley, 2002.
Dean, Nonviral Gene Transfer to Skeletal, Smooth, and Cardiac Muscle in Living Animals, Am J. Physiol Cell Physiol 289: 233-245, 2005.
Dev, et al., Medical Applications of Electroporation, IEEE Transactions of Plasma Science, vol. 28, No. 1, pp. 206-223, Feb. 2000.
Dev, et al., Sustained Local Delivery of Heparin to the Rabbit Arterial Wall with an Electroporation Catheter, Catheterization and Cardiovascular Diagnosis, Nov. 1998, vol. 45, No. 3, pp. 337-343.
Duraiswami, et al., Boundary Element Techniques for Efficient 2-D and 3-D Electrical Impedance Tomography, Chemical Engineenng Science, vol. 52, No. 13, pp. 2185-2196, 1997.
Duraiswami, et al., Efficient 2D and 3D Electrical Impedance Tomography Using Dual Reciprocity Boundary Element Techniques, Engineering Analysis with Boundary Elements 22, (1998) 13-31.
Duraiswami, et al., Solution of Electrical Impedance Tomography Equations Using Boundary Element Methods, Boundary Element Technology XII, 1997, pp. 226-237.
Edd, J., et al., In-Vivo Results of a New Focal Tissue Ablation Technique: Irreversible Electroporaton, IEEE Trans. Biomed. Eng. 53 (2006) p. 1409-1415.

(56) References Cited

OTHER PUBLICATIONS

Edd, J.F, et al., 2007, "Mathematical modeling of irreversible electroporation fortreatment planning.", Technology in Cancer Research and Treatment., 6:275-286.

Erez, et al., Controlled Destruction and Temperature Distributions in Biological Tissues Subjected to Monoactive Electrocoagulation, Transactions of the ASME: Journal of Mechanical Design, vol. 102, Feb. 1980.

Extended European Search Report. May 11, 2012. PCT/US2009042100 from EP 09739678.2.

Foster, R.S., et al., Production of Prostatic Lesions in Canines Using Transrectally Administered High-Intensity Focused Ultrasound. Eur. Urol., 1993; 23: 330-336.

Fox, et al., Sampling Conductivity Images via MCMC, Mathematics Department, Auckland University, New Zealand, May 1997.

Garcia et al., "Irreversible electroporation (IRE) to treat brain cancer." ASME Summer Bioengineering Conference, Marco Island, FL, Jun. 25-29, 2008.

Garcia, P. et al. Intracranial nonthermal irreversible electroporation: in vivo analysis. J Membr Biol 236, 127-136 (2010).

Gauger, et al., A Study of Dielectric Membrane Breakdown in the Fucus Egg, J. Membrane Biol., vol. 48, No. 3, pp. 249-264, 1979.

Gehl, et al., In Vivo Electroporation of Skeletal Muscle: Threshold, Efficacy and Relation to Electric Field Distribution, Biochimica et Biphysica Acta 1428, 1999, pp. 233-240.

Gençer, et al., Electrical Impedance Tomography: Induced-Current Imaging Achieved with a Multiple Coil System, IEEE Transactions on Biomedical Engineering, vol. 43, No. 2, Feb. 1996.

Gilbert, et al., Novel Electrode Designs for Electrochemotherapy, Biochimica et Biophysica Acta 1334, 1997, pp. 9-14.

Gilbert, et al., The Use of Ultrasound Imaging for Monitoring Cryosurgery Proceedings 6th Annual Conference, IEEE Engineering in Medicine and Biology, 107-111, 1984.

Gilbert, T. W., et al., "Decellularization of tissues and organs", Biomaterials, Elsevier Science Publishers, Barking, GB, vol. 27, No. 19, Jul. 1, 2006, pp. 3675-3683.

Glidewell, et al., The Use of Magnetic Resonance Imaging Data and the Inclusion of Anisotropic Regions in Electrical Impedance Tomography, Biomed, Sci. Instrum. 1993; 29: 251-7.

Gothelf, et al., Electrochemotherapy: Results of Cancer Treatment Using Enhanced Delivery of Bleomycin by Electroporation, Cancer Treatment Reviews 2003: 29: 371-387.

Griffiths, et al., A Dual-Frequency Electrical Impedance Tomography System, Phys. Med. Biol., 1989, vol. 34, No. 10, pp. 1465-1476.

Griffiths, The Importance of Phase Measurement in Electrical Impedance Tomography, Phys. Med. Biol., 1987, vol. 32, No. 11, pp. 1435-1444.

Griffiths, Tissue Spectroscopy with Electrical Impedance Tomography: Computer Simulations, IEEE Transactions on Biomedical Engineering, vol. 42, No. 9, Sep. 1995.

Gumerov, et al., The Dipole Approximation Method and Its Coupling with the Regular Boundary Element Method for Efficient Electrical Impedance Tomography, Boundary Element Technology XIII, 1999.

Hapala, Breaking the Barrier: Methods for Reversible Permeabilization of Cellular Membranes, Critical Reviews in Biotechnology, 17(2): 105-122, 1997.

Heller, et al., Clinical Applications of Electrochemotherapy, Advanced Drug Delivery Reviews, vol. 35, pp. 119-129, 1999.

Ho, et al., Electroporation of Cell Membranes: A Review, Critical Reviews in Biotechnology, 16(4): 349-362, 1996.

Holder, et al., Assessment and Calibration of a Low-Frequency System for Electrical Impedance Tomography (EIT), Optimized for Use in Imaging Brain Function in Ambulant Human Subjects, Annals of the New York Academy of Science, vol. 873, Issue 1, Electrical BI, pp. 512-519, 1999.

Huang, et al., Micro-Electroporation: Improving the Efficiency and Understanding of Electrical Permeabilization of Cells, Biomedical Microdevices, vol. 21, pp. 145-150, 1999.

Hughes, et al., An Analysis of Studies Comparing Electrical Impedance Tomography with X-Ray Videofluoroscopy in the Assessment of Swallowing, Physiol. Meas. 15, 1994, pp. A199-A209.

Issa, et al., The TUNA Procedure for BPH: Review of the Technology: The TUNA Procedure for BPH: Basic Procedure and Clinical Results, Reprinted from Infections in Urology, Jul./Aug. 1998 and Sep./Oct. 1998.

Ivanuša, et al., MRI Macromolecular Contrast Agents as Indicators of Changed Tumor Blood Flow, Radiol. Oncol. 2001; 35(2): 139-47.

Al-Sakere, B. et al., 2007, "Tumor ablation with irreversible electroporation." PLoS ONE 2.

Amasha, et al., Quantitatve Assessment of Impedance Tomography for Temperature Measurements in Microwave Hyperthermia, Clin. Phys. Physiol. Meas., 1998, Suppl. A, 49-53.

Andreason, Electroporation as a Technique for the Transfer of Macromolecules into Mammalian Cell Lines, J. Tiss. Cult. Meth., 15:56-62, 1993.

Baker, et al., Calcium-Dependent Exocytosis in Bovine Adrenal Medullary Cells with Leaky Plasma Membranes, Nature, vol. 276, pp. 620-622, 1978.

Barber, Electrical Impedance Tomography Applied Potential Tomography, Advances in Biomedical Engineering, Beneken and Thevenin, eds., IOS Press, 1993.

Beebe, S.J., et al., Nanosecond pulsed electric field (nsPEF) effects on cells and tissues: apoptosis induction and tumor growth inhibition. PPPS-2001 Pulsed Power Plasma Science 2001, 28th IEEE International Conference on Plasma Science and 13th IEEE International Pulsed Power Conference, Digest of Technical Papers (Cat. No. 01CH37251). IEEE, Part vol. 1, 2001, pp. 211-215, vol. I, Piscataway, NJ, USA.

Blad, et al., Impedance Spectra of Tumour Tissue in Comparison with Normal Tissue; a Possible Clinical Application for Electrical Impedance Tomography, Physiol. Meas. 17 (1996) A105-A115.

Bolland, F., et al., "Development and characterisation of a full-thickness acellular porcine bladder matrix for tissue engineering", Biomaterials, Elsevier Science Publishers, Barking, GB, vol. 28, No. 6, Nov. 28, 2006, pp. 1061-1070.

Boone, K., Barber, D. & Brown, B. Review—Imaging with electricity: report of the European Concerted Action on Impedance Tomography. J. Med. Eng. Technol. 21, 201-232 (1997).

BPH Management Strategies: Improving Patient Satisfaction, Urology Times, May 2001, vol. 29, Supplement 1.

Brown, et al., Blood Flow Imaging Using Electrical Impedance Tomography, Clin. Phys. Physiol. Meas., 1992. vol. 13, Suppl. A, 175-179.

Brown, S.G., Phototherapy of tumors. World J. Surgery, 1983. 7: p. 700-9.

Chandrasekar, et al., Transurethral Needle Ablation of the Prostate (TUNA)—a Propsective Study, Six Year Follow Up, (Abstract), Presented at 2001 National Meeting, Anaheim, CA, Jun. 5, 2001.

Coates, C.W.,et al., "The Electrical Discharge of the Electric Eel, Electrophorous Electricus," Zoologica, 1937, 22(1), pp. 1-32.

Cook, et al., ACT3: A High-Speed, High-Precision Electrical Impedance Tomograph, IEEE Transactions on Biomedical Engineering, vol. 41, No. 8, Aug. 1994.

Co-pending U.S. Appl. No. 10/571,162, filed Oct. 18, 2006 (published as 2007/0043345 on Feb. 22, 2007).

Co-Pending U.S. Appl. No. 12/432,295, filed Apr. 29, 2009.

Co-Pending U.S. Appl. No. 12/432,295, Final Rejection dated Mar. 21, 2012, 14 pages.

Co-Pending U.S. Appl. No. 12/432,295, Non-Final Rejection dated Nov. 10, 2011, 10 pages.

Co-Pending U.S. Appl. No. 12/432,295, Requirement for Restriction/Election dated Aug. 9, 2011, 7 pages.

Co-Pending U.S. Appl. No. 12/432,295, Response to Non-Final Rejection dated Jan. 23, 2012, 9 pages.

Co-Pending U.S. Appl. No. 12/432,295, Response to Requirement for Restriction/Election dated Sep. 2, 2011, 2 pages.

Co-Pending U.S. Appl. No. 12/432,295, Response with RCE to Final Rejection dated Jul. 23, 2012, 13 pages.

Co-Pending U.S. Appl. No. 12/491,151, Final Rejection dated Apr. 20, 2012, 8 pages.

(56) References Cited

OTHER PUBLICATIONS

Co-Pending U.S. Appl. No. 12/491,151, Non-Final Rejection dated Dec. 28, 2011, 7 pages.
Co-Pending U.S. Appl. No. 12/491,151, Requirement for Restriction/Election dated Dec. 2, 2011, 6 pages.
Co-Pending U.S. Appl. No. 12/491,151, Response to Non-Final Rejection dated Mar. 28, 2012, 10 pages.
Co-Pending U.S. Appl. No. 12/491,151, Response to Requirement for Restriction/Election dated Dec. 13, 2011, 2 pages.
Co-Pending U.S. Appl. No. 12/491,151, Response with RCE to Final Rejection dated Aug. 20, 2012, 14 pages.
Co-Pending U.S. Appl. No. 12/491,151, Supplemental Amendment dated Dec. 17, 2012, 6 pages.
Co-Pending U.S. Appl. No. 12/609,779, filed Oct. 30, 2009.
Co-Pending U.S. Appl. No. 12/609,779, Final Rejection dated Oct. 25, 2012, 20 pages.
Co-Pending U.S. Appl. No. 12/609,779, Non-Final Rejection dated May 23, 2012, 17 pages.
Co-Pending U.S. Appl. No. 12/609,779, Notice of Allowance dated Feb. 12, 2013, 7 pages.
Co-Pending U.S. Appl. No. 12/609,779, Notice of Allowance dated May 23, 2013, 2 pages.
Co-Pending U.S. Appl. No. 12/609,779, Response to Non-Final Rejection dated Sep. 24, 2012, 37 pages.
Co-Pending U.S. Appl. No. 12/609,779, Response with RCE to Final Rejection dated Dec. 18, 2012, 20 pages.
Co-pending U.S. Appl. No. 12/751,826, filed Mar. 31, 2010 (published as 2010/0250209 on Sep. 30, 2010).
Co-pending U.S. Appl. No. 12/751,854, filed Mar. 31, 2010 (published as 2010/0249771 on Sep. 30, 2010).
Co-Pending U.S. Appl. No. 12/757,901, filed Apr. 9, 2010.
Co-Pending U.S. Appl. No. 12/906,923, filed Oct. 18, 2010.
Co-Pending Application No. PCT/US04/43477, filed Dec. 21, 2004.
Co-Pending Application No. PCT/US09/42100, filed Apr. 29, 2009.
Co-Pending Application No. PCT/US09/62806, filed Oct. 30, 2009.
Co-Pending Application No. PCT/US10/30629, filed Apr. 9, 2010.
Co-Pending Application No. PCT/US10/53077, filed Oct. 18, 2010.
Co-Pending Application No. PCT/US11/32067, filed Nov. 23, 2011.
Co-Pending Application No. PCT/US11/62067, filed Nov. 23, 2011.
Co-Pending Application No. PCT/US11/66239, filed Dec. 20, 2011.
Co-pending Application No. PCT/US2010/029243, filed Mar. 30, 2010, published as WO 2010/117806 on Oct. 14, 2010.
Jaroszeski, et al., In Vivo Gene Delivery by Electroporation, Advanced Drug Delivery Review, vol. 35, pp. 131-137, 1999.
Jossinet et al., Electrical Impedance Endo-Tomography: Imaging Tissue From Inside, IEEE Transactions on Medical Imaging, vol. 21, No. 6, Jun. 2002, pp. 560-565.
Kinosita, et al., Hemolysis of Human Erythrocytes by a Transient Electric Field, Proc. Natl. Acad. Sci. USA, vol. 74, No. 5, pp. 1923-1927, 1977.
Lee, E. W. et al. Advanced Hepatic Ablation Technique for Creating Complete Cell Death : Irreversibie Electroporation. Radiology 255, 426-433, doi:10.1148/radiol.10090337 (2010).
Liu, et al., Measurement of Pharyngeal Transit Time by Electrical Impedance Tomography, Clin. Phys. Physiol. Meas., 1992, vol. 13, Suppl. A, pp. 197-200.
Lundqvist, et al., Altering the Biochemical State of Individual Cultured Cells and Organelles with Ultramicroelectrodes, Proc. Natl. Acad. Sci. USA, vol. 95, pp. 10356-10360. Sep. 1998.
Lurquin, Gene Transfer by Electroporation, Molecular Biotechnology, vol. 7, 1997.
Lynn, et al., A New Method for the Generation and Use of Focused Ultrasound in Experimental Biology, The Journal of General Physiology, vol. 26, 179-193, 1942.
Maor et al., The Effect of Irreversible Electroporation on Blood Vessels, Tech. in Cancer Res. and Treatment, vol. 6, No. 4, Aug. 2007, pp. 307-312.
Maor, E., A. Ivorra, and B. Rubinsky, Non Thermal Irreversible Electroporation: Novel Technology for Vascular Smooth Muscle Cells Ablation. PLoS ONE, 2009, 4(3): p. e4757.

Maor, E., A. Ivorra, J. Leor, and B. Rubinsky, Irreversible electroporation attenuates neointimal formation after angioplasty, IEEE Trans Biomed Eng, Sep. 2008, 55(9): p. 2268-74.
Miklavčič, et al., A Validated Model of an in Vivo Electric Field Distribution in Tissues for Electrochemotherapy and for DNA Electrotransfer for Gene Therapy, Biochimica et Biophysica Acta 1523 (2000), pp. 73-83.
Miklavčič, et al., The Importance of Electric Field Distribution for Effective in Vivo Electroporation of Tissues, Biophysical Journal, vol. 74, May 1998, pp. 2152-2158.
Miller, L., et al., Cancer cells ablation with irreversible electroporation, Technology in Cancer Research and Treatment 4 (2005) 699-706.
Mir et al., "Mechanisms of Electrochemotherapy" Advanced Drug Delivery Reviews 35:107-118 (1999).
Mir, et al., Effective Treatment of Cutaneous and Subcutaneous Malignant Tumours by Electrochemotherapy, British Journal of Cancer, vol. 77, No. 12, pp. 2336-2342, 1998.
Mir, et al., Electrochemotherapy Potentiation of Antitumour Effect of Bleomycin by Local Electric Pulses, European Journal of Cancer, vol. 27, No. 1, pp. 68-72, 1991.
Mir, et al., Electrochemotherapy, a Novel Antitumor Treatment: First Clinical Trial, C.R. Acad. Sci. Paris, Ser. III, vol. 313, pp. 613-618, 1991.
Mir, L.M. and Orlowski, S., The basis of electrochemotherapy, in Electrochemotherapy, electrogenetherapy, and transdermal drug delivery: electrically mediated delivery of molecules to cells, M.J. Jaroszeski. R. Heller, R. Gilbert, Editors, 2000, Humana Press, p. 99-118.
Mir, L.M., et al., Electric Pulse-Mediated Gene Delivery to Various Animal Tissues, in Advances in Genetics, Academic Press, 2005, p. 83-114.
Mir, Therapeutic Perspectives of In Vivo Cell Electropermeabilization, Bioelectrochemistry, vol. 53, pp. 1-10, 2000.
Narayan, et al., Establishment and Characterization of a Human Primary Prostatic Adenocarcinoma Cell Line (ND-1), The Journal of Urology, vol. 148, 1600-1604, Nov. 1992.
Naslund, Cost-Effectiveness of Minimally Invasive Treatments and Transurethral Resection (TURP) in Benign Prostatic Hyperplasia (BPH), (Abstract), Presented at 2001 AUA National Meeting,, Anaheim. CA, Jun. 5, 2001.
Naslund, Michael J., Transurethral Needle Ablation of the Prostate, Urology, vol. 50, No. 2, Aug. 1997.
Neal II, Robert E. and R.V. Davalos, The Feasibility of Irreversible Electroporation for the Treatment of Breast Cancer and Other Heterogeneous Systems, Ann Biomed Eng, 2009, 37(12): p. 2615-2625.
Neumann, et al., Gene Transfer into Mouse Lyoma Cells by Electroporation in High Electric Fields, J. Embo., vol. 1, No. 7, pp. 841-845, 1982.
Neumann, et al., Permeability Changes Induced by Electric Impulses in Vesicular Membranes, J. Membrane Biol., vol. 10, pp. 279-290, 1972.
Okino, et al., Effects of High-Voltage Electrical Impulse and an Anticancer Drug on In Vivo Growing Tumors, Japanese Journal of Cancer Research, vol. 78, pp. 1319-1321, 1987.
Onik, et al., Sonographic Monitoring of Hepatic Cryosurgery in an Experimental Animal Model, AJR American J. of Roentgenology, vol. 144, pp. 1043-1047, May 1985.
Onik, et al., Ultrasonic Characteristics of Frozen Liver, Cryobiology. vol. 21, pp. 321-328, 1984.
Organ, L.W., Electrophysiological principles of radiofrequency lesion making, Apply. Neurophysiol., 1976. 39: p. 69-76.
Ott, H. C., et al., "Perfusion-decellularized matrix: using nature's platform to engineer a bioartificial heart", Nature Medicine, Nature Publishing Group, New York, NY, US, vol. 14, No. 2, Feb. 1, 2008, pp. 213-221.
Pavselj, N. et al. The course of tissue permeabilization studied on a mathematical model of a subcutaneous tumor in small animals. IEEE Trans Biomed Eng 52, 1373-1381 (2005).
PCT International Preliminary Repot on Patentability of Corresponding International Application No. PCT/2011/062067, dated May 28, 2013.

(56) References Cited

OTHER PUBLICATIONS

PCT International Preliminary Report on Patentability of Corresponding International Application No. PCT/2011/066239, dated Jun. 25, 2013.
PCT International Search Report (Aug. 2, 2011), Written Opinion (Aug. 2, 2011), and International Preliminary Report on Patentability (Apr. 17, 2012) of PCT/US10/53077.
PCT International Search Report (Aug. 22, 2012), and Written Opinion (Aug. 22, 2012) of PCT/US11/66239.
PCT International Search Report (Aug. 26, 2005), Written Opinion (Aug. 26, 2005), and International Preliminary Report on Patentability (Jun. 26, 2006) of PCT/US2004/043477.
PCT International Search Report (Jan. 19, 2010), Written Opinion (Jan. 19, 2010), and International Preliminary Report on Patentability (Jan. 4, 2010) of PCT/US09/62806, 15 pgs.
PCT International Search Report (Jul. 15, 2010), Written Opinion (Jul. 15, 2010), and International Preliminary Report on Patentability (Oct. 11, 2011) from PCT/US2010/030629.
PCT International Search Report (Jul. 9, 2009), Written Opinion (Jul. 9, 2009), and International Preliminary Report on Patentability (Nov. 2, 2010) of PCT/US2009/042100.
PCT International Search Report and Written Opinion (Jul. 25, 2012) of PCT/US2011/062067.
PCT International Search Report, 4 pgs, (Jul. 30, 2010), Written Opinion, 7 pgs, (Jul. 30, 2010), and International Preliminary Report on Patentability, 8 pgs, (Oct. 4, 2011) from PCT/US2010/029243.
Phillips, M., Maor, E. & Rubinsky, B. Non-Thermal Irreversible Electroporation for Tissue Decellularization. J. Biomech. Eng, doi:10.1115/1.4001882 (2010).
Piñero, et al., Apoptotic and Necrotic Cell Death Are Both Induced by Electroporation in HL60 Human Promyeloid Leukaemia Cells, Apoptosis, vol. 2, No. 3, 330-336, Aug. 1997.
Precision Office Tuna System, When Patient Satisfaction is Your Goal, VidaMed 2001.
Rajagopal, V. and S.G. Rockson, Coronary restenosis: a review of mechanisms and management, The American Journal of Medicine, 2003, 115(7): p. 547-553.
Rols, M.P., et al., Highly Efficient Transfection of Mammalian Cells by Electric Field Pulses: Application to Large Volumes of Cell Culture by Using a Flow System, Eur. J. Biochem. 1992, 206, pp. 115-121.
Rubinsky, B., "Irreversible Electroporation in Medicine", Technology in Cancer Research and Treatment, vol. 6, No. 4, Aug. 1, 2007, pp. 255-259.
Rubinsky, B., ed, Cryosurgery. Annu Rev. Biomed. Eng. vol. 2 2000. 157-187.
Sano, M. B., et al., "Towards the creation of decellularized organ constructs using irreversible electroporation and active mechanical perfusion", Biomedical Engineering Online, Biomed Central LTD, London, GB, vol. 9, No. 1, Dec. 10, 2010, p. 83.
Schmukler, Impedance Spectroscopy of Biological Cells, Engineering in Medicine and Biology Society. Engineering Advances: New Opportunities for Biomedical Engineers, Proceedings of the 16th Annual Internal Conference of the IEEE, vol. 1, p. A74, downloaded from IEEE Xplore website, 1994.
Sel, D. et al. Sequential finite element model of tissue electropermeabilization. IEEE Transactions on Biomedical Engineering 52, 816-827, doi:10.1109/tbme.2005.845212 (2005).
Sel, D., Lebar, A. M. & Miklavcic, D. Feasibility of employing model-based optimization of pulse amplitude and electrode distance for effective tumor electropermeabilization. IEEE Trans Biomed Eng 54, 773-781 (2007).
Sersa, et al., Reduced Blood Flow and Oxygenation in SA-1 Tumours after Electrochemotherapy with Cisplatin, British Journal of Cancer, 87, 1047-1054, 2002.
Sersa, et al., Tumour Blood Flow Modifying Effects of Electrochemotherapy: a Potential Vascular Targeted Mechanism, Radiol. Oncol., 37(1): 43-8, 2003.
Sharma, et al., Poloxamer 188 Decreases Susceptibility of Artificial Lipid Membranes to Electroporation, Biophysical Journal, vol. 71, No. 6, pp. 3229-3241, Dec. 1996.
Shiina, S., et al, Percutaneous ethanol injection therapy for hepatocellular carcinoma: results in 146 patients. AJR, 1993, 160: p. 1023-8.
Tekle, Ephrem, R. Dean Astumian, and P. Boon Chock, Electroporation by using bipolar oscillating electric field: An improved method for DNA transfection of NIH 3T3 cells, Proc. Natl. Acad. Sci., vol. 88, pp. 4230-4234, May 1991, Biochemistry.
Thompson, et al., To determine whether the temperature of 2% lignocaine gel affects the initial discomfort which may be associated with its instillation into the male urethra. BJU International (1999), 84, 1035-1037.
TUNA—Suggested Local Anesthesia Guidelines, no date available.
Vidamed, Inc., Transurethral Needle Ablation (TUNA): Highlights from Worldwide Clinical Studies, Vidamed's Office TUNA System, 2001.
Weaver, Electroporation: A General Phenomenon for Manipulating Cells and Tissues, Journal of Cellular Biochemistry, 51: 426-435, 1993.
Weaver, et al., Theory of Electroporation: A Review, Bioelectrochemistry and Bioenergetics, vol. 41, pp. 136-160, 1996.
Weaver, J. C., Electroporation of biological membranes from multicellular to nano scales, IEEE Trns. Dielectr. Electr. Insul. 10, 754-768 (2003).
Weisstein: Cassini Ovals. From MathWorld—A. Wolfram Web Resource; Apr. 30, 2010; http://mathworld.wolfram.com/ (updated May 18, 2011).
Zimmermann, et al., Dielectric Breakdown of Cell Membranes, Biophysical Journal, vol. 14, No. 11, pp. 881-899, 1974.
Zlotta, et al., Long-Term Evaluation of Transurethral Needle Ablation of the Prostate (TUNA) for Treatment of Benign Prostatic Hyperplasia (BPH): Clinical Outcome After 5 Years. (Abstract) Presented at 2001 AUA National Meeting, Anaheim, CA—Jun. 5, 2001.
Zlotta, et al., Possible Mechanisms of Action of Transurethral Needle Ablation of the Prostate on Benign Prostatic Hyperplasia Symptoms: a Neurohistochemical Study, Reprinted from Journal of Urology, vol. 157, No. 3, Mar. 1997, pp. 894-899.
Agerholm-Larsen, B., et al., "Preclinical Validation of Electrochemotherapy as an Effective Treatment for Brain Tumors", Cancer Research 71: 3753-3762 (2011).
Appelbaum, L., et al., "US Findings after Irreversible Electroporation Ablation: Radiologic-Pathologic Correlation" Radiology 262(1), 117-125 (2012).
Arena, Christopher B., et al., "Towards the development of latent heat storage electrodes for electroporation-based therapies", Applied Physics Letters, 101, 083902 (2012).
Arena, Christopher B., et al.,"Phase Change Electrodes for Reducing Joule Heating During Irreversible Electroporation". Proceedings of the ASME 2012 Summer Bioengineering Conference, SBC2012, Jun. 20-23, 2012, Fajardo, Puerto Rico.
Bagla, S. and Papadouris, D., "Percutaneous Irreversible Electroporation of Surgically Unresectable Pancreatic Cancer: A Case Report" J. Vascular Int. Radiol. 23(1), 142-145 (2012).
Bancroft, et al., Design of a Flow Perfusion Bioreactor System for Bone Tissue-Engineering Applications, Tissue Engineering, vol. 9, No. 3, 2003, p. 549-554.
Ben-David, E.,et al., "Characterization of Irreversible Electroporation Ablation in In Vivo Procine Liver" Am. J. Roentgenol. 198(1), W62-W68 (2012).
Cemazar M, Parkins CS, Holder AL, Chaplin DJ, Tozer GM, et al., "Electroporation of human microvascular endothelial cells: evidence for an anti-vascular mechanism of electrochemotherapy", Br J Cancer 84: 565-570 (2001).
Co-Pending U.S. Appl. No. 12/432,295, Non-Final Office Action dated Nov. 26, 2013, 15 pages.
Co-Pending U.S. Appl. No. 12/906,923, Requirement for Restriction/Election, dated Jan. 29, 2014, 9 pages.
Corovic, S., et al., "Analytical and numerical quantification and comparison of the local electric field in the tissue for different electrode configurations," Biomed Eng Online, 6, 2007.

(56) References Cited

OTHER PUBLICATIONS

Daud, A.I., et al., "Phase I Trial of Interleukin-12 Plasmid Electroporation in Patients With Metastatic Melanoma," Journal of Clinical Oncology, 26, 5896-5903, Dec. 20, 2008.
Davalos, R.V., et al., "Electrical impedance tomography for imaging tissue electroporation," IEEE Transactions on Biomedical Engineering, 51, 761-767, 2004.
Demirbas, M. F., "Thermal Energy Storage and Phase Change Materials: An Overview" Energy Sources Part B 1(1), 85-95 (2006).
Ellis TL, Garcia PA, Rossmeisl JH, Jr., Henao-Guerrero N, Robertson J, et al., "Nonthermal irreversible electroporation for intracranial surgical applications. Laboratory investigation", J Neurosurg 114: 681-688 (2011).
Faroja, M., et al., "Irreversible Electroporation Ablation: Is the entire Damage Nonthermal?", Radiology, 266(2), 462-470 (2013).
Foster RS, "High-intensity focused ultrasound in the treatment of prostatic disease", European Urology, 1993, vol. 23 Suppl 1, pp. 29-33.
Garcia P.A., et al., "7.0-T Magnetic Resonance Imaging Characterization of Acute Blood-Brain-Barrier Disruption Achieved with Intracranial Irreversible Electroporation", PLOS ONE, Nov. 2012, 7:11, e50482.
Garcia P.A., et al., "Pilot study of irreversible electroporation for intracranial surgery", Conf Proc IEEE Eng Med Biol Soc, 2009:6513-6516, 2009.
Garcia PA, Rossmeisl JH, Jr., Neal RE, 2nd, Ellis TL, Davalos RV, "A Parametric Study Delineating Irreversible Electroporation from Thermal Damage Based on a Minimally Invasive Intracranial Procedure", Biomed Eng Online 10: 34 (2011).
Garcia, P. A., et al., "Towards a predictive model of electroporation-based therapies using pre-pulse electrical measurements," Conf Proc IEEE Eng Med Biol Soc, vol. 2012, pp. 2575-2578, 2012.
Garcia, P. A., et al., "Non-thermal Irreversible Electroporation (N-TIRE) and Adjuvant Fractioned Radiotherapeutic Multimodal Therapy for Intracranial Malignant Glioma in a Canine Patient" Technol. Cancer Res. Treatment 10(1), 73-83 (2011).
Hjouj, M., et al., "Electroporation-Induced BBB Disruption and Tissue Damage Depicted by MRI", Neuro-Oncology 13: Issue suppl 3, abstract ET-32 (2011).
Hjouj, M., et al., "MRI Study on Reversible and Irreversible Electroporation Induced Blood Brain Barrier Disruption", PLOS ONE, Aug. 2012, 7:8, e42817.
Lee, E.W., et al., "Imaging guided percutaneous irreversible electroporation: ultrasound and immunohistological correlation", Technol Cancer Res Treat 6: 287-294 (2007).
Li, W., et al., "The Effects of Irreversible Electroporation (IRE) on Nerves" PloS One, Apr. 2011, 6(4), e18831.
Mahmood, F., et al., "Diffusion-Weighted MRI for Verification of Electroporation-Based Treatments", Journal of Membrane Biology 240: 131-138 (2011).
Mahnic-Kalamiza, S., et al., "Educational application for visualization and analysis of electric field strength in multiple electrode electroporation," BMC Med Educ, vol. 12, p. 102, 2012
Marty, M., et al., "Electrochemotherapy—An easy, highly effective and safe treatment of cutaneous and subcutaneous metastases: Results of ESOPE (European Standard Operating Procedures of Electrochemotherapy) study," European Journal of Cancer Supplements, 4, 3-13, 2006.
Neal II, R. E., et al., "Experimental characterization and numerical modeling of tissue electrical conductivity during pulsed electric fields for irreversible electroporation treatment planning," IEEE Trans Biomed Eng., vol. 59:4, pp. 1076-1085. Epub 2012 Jan. 6, 2012.
Neal II, R. E., et al., "Successful Treatment of a Large Soft Tissue Sarcoma with Irreversible Electroporation", Journal of Clinical Oncology, 29:13, e372-e377 (2011).
Rubinsky, B., et al., "Irreversible Electroporation: A New Ablation Modality—Clinical Implications" Technol. Cancer Res. Treatment 6(1), 37-48 (2007).
Salford, L.G., et al., "A new brain tumour therapy combining bleomycin with in vivo electropermeabilization", Biochem. Biophys. Res. Commun., 194(2): 938-943 (1993).
Sharma, A. , et al., "Review on Thermal Energy Storage with Phase Change Materials and Applications", Renewable Sustainable Energy Rev. 13(2), 318-345 (2009).
Thomson, K. R., et al., "Investigation of the Safety of Irreversible Electroporation in Humans" J. Vascular Int. Radiol. 22 (5), 611-621 (2011).
Co-Pending U.S. Appl. No. 12/432,295, Final Rejection dated Jun. 16, 2014, 14 pages.
Co-Pending U.S. Appl. No. 12/432,295, Response to Non-Final Office Action, dated Apr. 28, 2014, 14 pages.
Co-Pending U.S. Appl. No. 12/491,151, Non-Final Rejection dated Apr. 4, 2014, 12 pages.
Co-Pending U.S. Appl. No. 12/906,923, Response to Restriction Requirement, dated Mar. 19, 2014, 3 pages.

\* cited by examiner

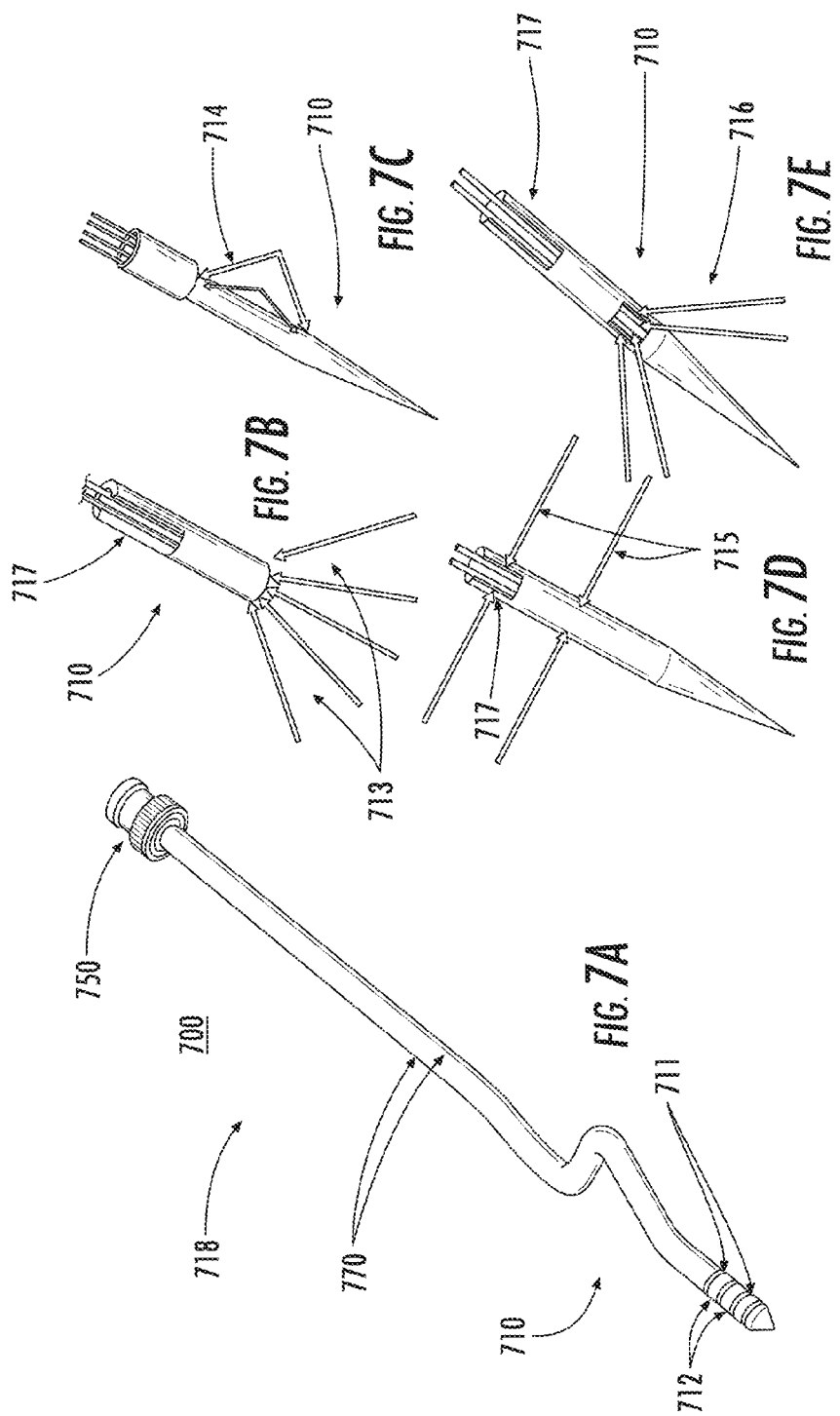

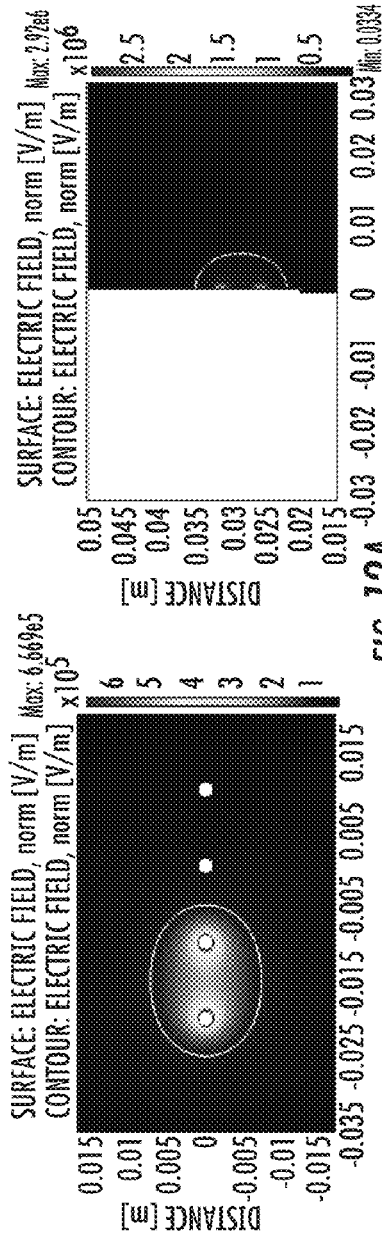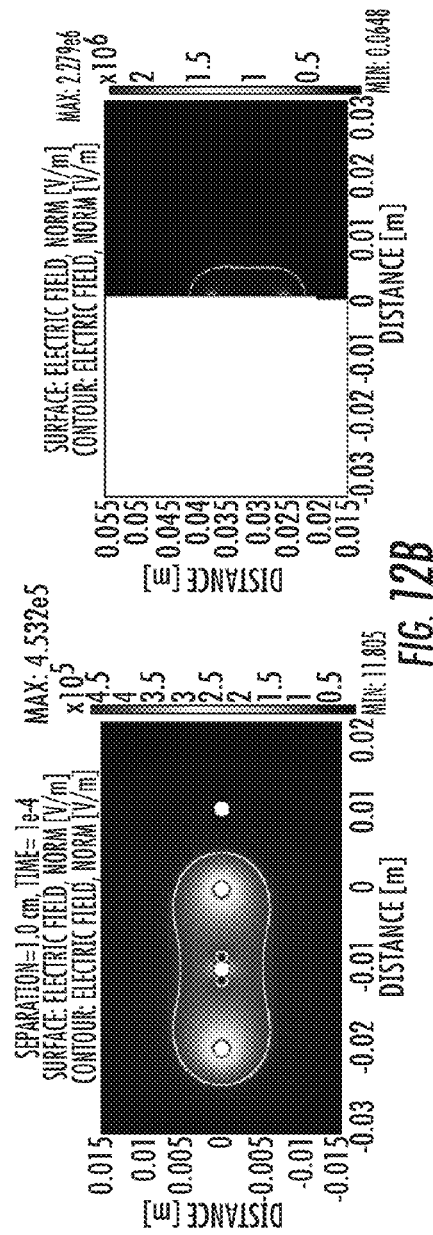
FIG. 12A
FIG. 12B

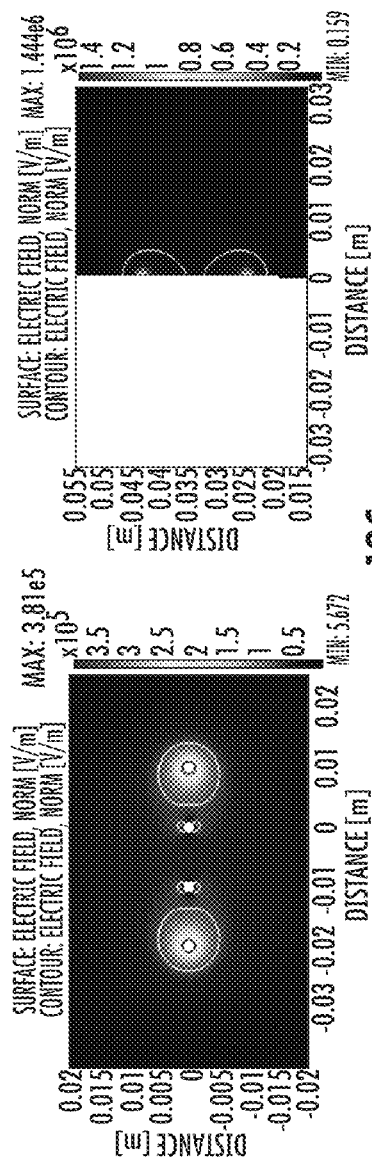
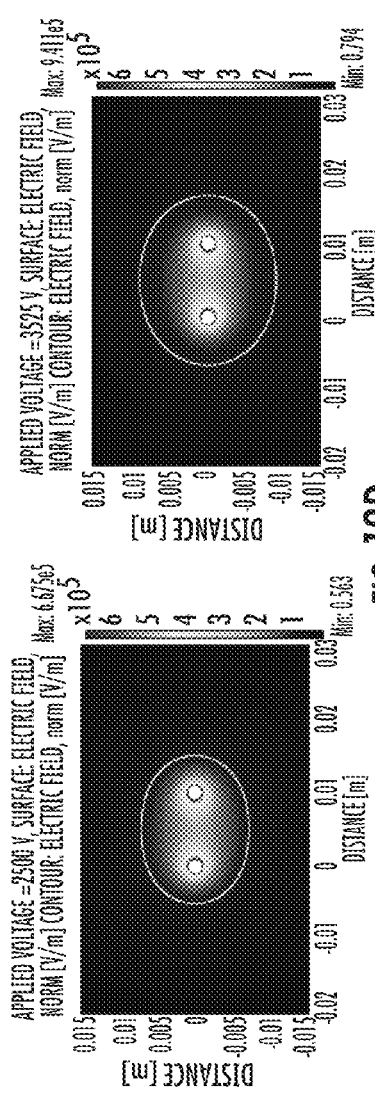
FIG. 12C
FIG. 12D

IRREVERSIBLE ELECTROPORATION USING NANOPARTICLES

CROSS-REFERENCE TO RELATED APPLICATIONS

The present application is a Continuation application of U.S. patent application Ser. No. 12/609,779 filed on Oct. 30, 2009, which is a Continuation-In-Part application of U.S. patent application Ser. No. 12/491,151, filed on 24 Jun. 2009, which is a Continuation-in-Part application of U.S. patent application Ser. No. 12/432,295, filed on Apr. 29, 2009, which application claims priority to U.S. provisional application No. 61/125,840, filed on Apr. 29, 2008; U.S. patent application Ser. No. 12/491,151 also claims the benefit of the filing date of U.S. provisional application No. 61/171,564, filed on Apr. 22, 2009, U.S. provisional application No. 61/167,997, filed on Apr. 9, 2009, and U.S. provisional application No. 61/075,216, filed on Jun. 24, 2008. The disclosures of which are hereby incorporated herein by reference in their entireties.

BACKGROUND OF THE INVENTION

1. Field of the Invention

The present invention relates to the field of biomedical engineering and medical treatment of diseases and disorders. More specifically, the invention relates to devices and methods for destroying aberrant cell masses, including tumor tissues, such as cancerous tissues of the brain and leukemias.

2. Description of Related Art

Treatment of abnormal cell growth in or on normal body tissues and organs can be achieved, in many different ways to achieve reduced cell growth, reduction of the resulting aberrant cell mass, and even destruction of the aberrant cell mass. In general, treatments known in the art involve surgical intervention to physically remove the aberrant cell mass, radiation to kill the cells of the aberrant cell mass, exposure of aberrant cells to toxic chemicals chemotherapy), or a combination of two or all three of these. While each treatment modality has shown significant effectiveness m treatment of various cell proliferative diseases, no one technique has been shown to be highly effective at treating all types of cell proliferative diseases and disorders. Furthermore, each technique has significant drawbacks. For example, surgical intervention is highly effective at removal of solid tumors on tissues and organs that are physically accessible and capable of sustaining physical damage or capable of regeneration. However, surgical intervention can be difficult to perform on tumors that are not readily accessible or on organs that do not regenerate (e.g., brain tumors), and can involve substantial physical damage to the patient, requiring extensive recuperation times and follow-on treatments. Likewise, treatment with radiation can result in collateral damage to tissue surrounding the tumor, and can cause long-lasting side-effects, which can lower the quality of life of the patient. Similarly, chemotherapeutic treatments cause systemic damage to the patient, and can result in significant side-effects that might require a long recuperation period or permanent damage to the patient.

In the treatment of tumors, including malignant tumors, it is recognized in the medical arts that it is important to achieve ablation of the undesirable tissue in a well-controlled and precise way without affecting the surrounding healthy tissue. The inventors and their colleagues recently developed a new method to treat tumors, known as irreversible electroporation (IRE). The procedure involves placing electrodes within or near the targeted region to deliver a series of low energy, microsecond electric pulses for approximately 1 minute. These pulses permanently destabilize the cell membranes of the targeted tissue (e.g., tumor), thereby killing the cells, IRE does not affect major blood vessels, does not require the use of drugs and non-thermally kills neoplastic cells in a precise and controllable manner, without significantly damaging surrounding tissue. The inventors and their colleagues also recently showed the complete regression in 12 out of 13 treated tumors in vivo using IRE on a type of aggressive sarcoma implanted in nude mice (Al-Sakere, B. et al., 2007, "Tumor ablation with irreversible electroporation." PLoS ONE 2.).

Although advances have been made recently in the field of IRE and the concept of treatment of tumors with IRE has been established, the present inventors have recognized that there still exists a need in the art for improved devices and methods for ablating diseased or disordered tissues, such as tumor tissues, using IRE. The present invention addresses those needs.

SUMMARY OF THE INVENTION

The present invention provides an advancement over tissue ablation techniques previously devised by providing improved devices and methods for precisely and rapidly ablating diseased, damaged, disordered, or otherwise undesirable biological tissues in situ. As used herein the term ablation is used to indicate destruction of cells, but not necessarily destruction of the underlying extracellular matrix. More specifically, the present invention provides new devices and methods for ablating target tissues for the treatment of diseases and disorders, and particularly neoplasias, including both solid tumors and leukemias, using IRE in combination with nanoparticles. Use of IRE to decellularize diseased tissue provides a controlled, precise way to destroy aberrant cells of a tissue or organ, such as tumor or cancer cells or masses.

Non-thermal IRE is a method to kill undesirable cells using electric fields in tissue while preserving the ECM, blood vessels, and neural tubes/myelin sheaths. Certain electrical fields, when applied across a cell, have the ability to permeabilize the cell membrane through a process that has come to be called "electroporation". When electrical fields permeabilize the cell membrane temporarily, after which the cells survive, the process is known as "reversible electroporation". Reversible electroporation has become an important tool in biotechnology and medicine. Other electrical fields can cause the cell membrane to become permeabilized, after which the cells die. This deadly process is known as "irreversible electroporation". According to the present invention, non-thermal irreversible electroporation is a minimally invasive surgical technique to ablate undesirable tissue, for example, neoplastic cells or tissues. The technique is easy to apply, can be monitored and controlled, is not affected by local blood flow, and does not require the use of adjuvant drugs. The minimally invasive procedure involves placing needle-like electrodes into or around the targeted area to deliver a series of short and intense electric pulses that induce structural changes in the cell membranes that promote cell death. The voltages are applied in order to electroporate tissue without inducing significant Joule heating that would significantly damage major blood vessels and the ECM. For a specific tissue type and set of pulse conditions, the primary parameter determining the volume irreversibly electroporated is the electric field distribution within the tissue. Recent IRE animal experiments have verified the many beneficial effects resulting from this special mode of non-thermal cell ablation, such as preservation of major structures including the extracellular matrix, major blood vessels, and myelin sheaths, no scar formation, as well as its promotion of a beneficial immune response.

In a first aspect, the present invention provides a method for treating aberrant cell growth in animals. In general, the method comprises inserting one or more electrodes into or immediately adjacent to aberrant cell masses or in a region of neoplastic cell growth and applying IRE to cause irreversible cell death to the aberrant cells. In some embodiments, two or more electrodes are used to treat aberrant cells and effect cell death. The electrodes may be present on the same or different devices. Preferably, the parameters for IRE are selected to minimize or avoid excessive heating of the treated tissue and surrounding tissue, thus reducing collateral damage to healthy tissue near the aberrant cells being treated. In addition, it is preferable to minimize the total electrical charge delivered when treating, tissues, such as brain tissue, to avoid complications. The methods can be applied to treat a number of neoplasias, including any number of solid tumors, such as liver cancer, prostate cancer, and pancreatic adenoearcinoma. Exemplary in vivo therapeutic methods include regeneration of organs after treatment for a tumor, preparation of a surgical site for implantation of a medical device, skin grafting, and replacement of part or all of a tissue or organ, such as one damaged or destroyed by a disease or disorder (e.g., the liver). Exemplary organs car tissues include: heart lung, liver, kidney, urinary bladder, brain, ear, eye, or skin. In view of the fact that a subject may be a human or animal, the present invention has both medical and veterinary applications.

Viewed differently, the method for treating aberrant cell growth in animals can be considered a method of treating an animal (including humans) having an aberrant cell growth or mass in or on a tissue or an organ. In exemplary embodiments, the organ is a brain, and the aberrant cell mass is a benign or malignant tumor. In other exemplary embodiments, the cells to be treated are leukemia cells, such as those resident in bone marrow. Under this view, the method can be a method of treating an animal suffering from a disease or disorder resulting from aberrant cell growth by reducing or eliminating some or all of a mass (e.g., tumor) produced by the aberrant cell growth. In certain embodiments, the aberrant cell mass to be treated includes cells with cell cycling dysfunctions, including cells that are not dying or undergoing, apoptotic mechanisms of cell death or similar programmed cell death at appropriate, natural, or naturally induced, times, such as those mediated through protein bindings or intracellular cascades, in addition, the aberrant cell mass in certain embodiments includes cells with alterations (including genetic and protein expression and post-translational alterations and modifications) leading to immune system evasion or immune system indifference.

In embodiments of the methods of the present invention, IRE with nanoparticles is used to increase the treatment area without increasing the applied voltage and without causing significant thermal damage. Nanoparticles offer a promising solution for treatment of neoplasias because of their size (about 1 to about 1,000 nm) and ability to diffuse through extracellular spaces. The three most important properties of a nanoparticle for enhancing electric fields are its shape, orientation with respect to the applied field, and electrical properties (conductivity and permittivity). The contribution of each of these properties towards enhancing electric fields are shown in FIG. 18 for a spherical nanoparticle, a rod-shaped particle oriented perpendicular to the applied field, and a rod-shaped particle oriented parallel to the applied field with a range of conductivity and permittivity ratios. However, nanoparticle embodiments suitable for IRE are not limited to rod or spherical shaped particles. Other nanoparticle embodiments may include, but are not limited to, fullerenes (a.k.a. $C_{60}$, $C_{70}$, $C_{76}$, $C_{80}$, $C_{84}$), endohedral metallofullerenes (EMI's) (a.k.a. buckyballs, which contain additional atoms, ions, or clusters inside their fullerene cage), trimetallic nitride templated endohedral metallofullerenes (TNT EMFs, high-symmetry four-atom molecular cluster endohedrals which are formed in a trimetallic nitride template within the carbon cage), single-walled and multi-walled carbon nanotubes, branched and dendritic carbon nantotubes, gold nanorods, silver nanorods, single-walled and multi-walled boroninitrade nanotubes, carbon nanotube peapods (nanotubes with internal metallo-fullerenes and/or other internal chemical structures), carbon nanohorns, carbon nanohorn peapods, liposoines, nanoshells, dendrimers, quantum dots, superparamagnetic nanoparticles, nanorods, and cellulose nanoparticles. The particle embodiment can also include microparticles with the capability to enhance IRE effectiveness or selectivity. Other non-limiting exemplary nanoparticles include glass and polymer micro- and nano-spheres, biodegradable PLGA micro- and nano-spheres, gold, silver, carbon, and iron nanoparticles. In embodiments, the nanoparticles of the methods of the invention, including insulative and conductive nanoparticles of varying shape, can enhance pulsed electric field therapies by lowering the electric field threshold required for inducing IRE and enlarging the treatable area.

The nanoparticles can comprise modified surface chemistries to cause the localized destruction of targeted cells, while leaving untargeted cells intact. Although IRE has been shown to promote tumor regression, it cannot selectively kill cancer cells within a tumor mass without also killing healthy cells. The selectivity of pulsed electric field therapies can be enhanced through the use of nanoparticles that can be functionalized to target specific cancer cells using various antibodies or chemical compounds. These methods can be employed to reduce or eliminate neoplastic cells from a subject within and beyond the treatment margin, while maintaining proper organ function.

To effect the methods according to the invention, the present invention provides devices designed to treat aberrant cell masses using irreversible electroporation (IRE). While IRE devices have been disclosed prior to the priority date of this document, advanced surgical tools for in vivo IRE to treat diseased tissues and organs had not been developed. The present invention provides devices suitable for in vivo IRE treatment of diseases and disorders, particularly those associated with abnormal cell growth in or on a tissue or organ, which allow for minimally invasive treatment of patients suffering from such abnormal cell growth. The present inventors have designed microsurgical tools to treat currently inoperable tumors in humans and other animals through IRE. While not so limited, the designs provided herein are sufficient to ablate the majority of tumors smaller than about 3 cm in diameter, such as those about 14 cc in volume or less. The devices and methods of the invention are also suitable for treatment of non-solid tumors, such as leukemias.

BRIEF DESCRIPTION OF THE DRAWINGS

The accompanying drawings, which are incorporated in and constitute a part of this specification, illustrate several embodiments of the invention, and together with the written description, serve to explain certain principles of the invention.

FIG. 1A shows an MRI before IRE. T2 weighted; FIG. 1B shows superficial non-thermal IRE decellularization site. T2 weighted; and FIG. 1C shows post-contrast T1 weighted; the dog's right is conventionally projected on the left.

FIGS. 7A-7E depict various exemplary embodiments of a device according to the invention. FIG. 7A depicts a device, showing a connector, wiring, and electrodes disposed at the tip. FIGS. 7B-7E depict alternative placement of electrodes, which can be retractable.

FIG. 8A depicts an exploded view of the various concentric layers of materials making up the electrode tip.

FIGS. 9A and 9B depict an embodiment of the device of the invention, comprising a hollow core for delivery of bioactive agents.

FIGS. 12A-12E depict electrical field outputs from various configurations employing two electrodes. FIG. 12A depicts the use of two electrodes spaced 0.5 cm apart. FIG. 12B depicts the use of two electrodes spaced. 1.0 cm apart. FIG. 12C depicts the use of two electrodes spaced 1.5 cm apart. FIG. 12D depicts the use of two electrodes spaced 1.0 cm apart. FIG. 12E depicts a side view of electrical field outputs from one device having two electrically conductive regions separated by an insulative region of a length of 0.5 cm.

FIG. 13A depicts the use of electrodes of 2 mm, 0.5 mm, and 1 mm (from left to right). FIG. 13B depicts the use of electrodes of 2 mm, 1 mm, and 0.5 mm (from left to right). FIG. 13C depicts the use of electrodes of 1 mm, 2 mm, and 0.5 mm (from left to right).

FIG. 14A depicts a two-dimensional display for the use of four electrodes of alternating polarity. FIG. 14B depicts an axis symmetric display for the use of four similar electrodes of alternating polarity. FIG. 14C depicts a two-dimensional display for the use of four charged electrodes, the center two at 5000V and 0V and the outer two at 2500V. FIG. 14D depicts an axis symmetric display for the use of a similar electrode set up as FIG. 14C. FIG. 14E depicts a two-dimensional display for the use of three electrodes with the center one at 2500V and the outer two at 0V. FIG. 14F depicts an axis symmetric display for the use of three electrodes similar to FIG. 14E, FIG. 14G depicts a two-dimensional display for the use of three charged electrodes, the center at 0V, the left at 5000V, and the right at 2500V. FIG. 14H depicts an axis symmetric display for the use of a similar electrode set up as FIG. 14G. FIG. 14I depicts a two-dimensional display for the use of three charged electrodes, the center at 1750V, the left at 3000V, and the right at 0V.

FIG. 15A shows thermal effects without cooling, while FIG. 15B shows the thermal effects under the same pulsing conditions, but with electrode cooling. FIG. 15C shows thermal effects without cooling, while FIG. 15D shows the thermal effects under the same pulsing conditions, but with electrode, cooling.

DETAILED DESCRIPTION OF VARIOUS EMBODIMENTS OF THE INVENTION

Figure 1A:
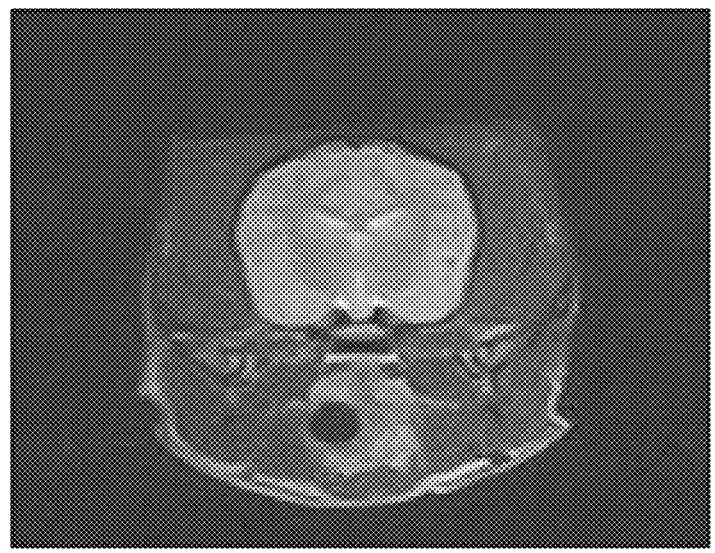
FIGS. 1A-1C show magnetic resonance imaging (MRI) images of tissue after non-thermal IRE on canine tissue. The images show that non-thermal IRE decellularization zones were sharply demarcated T1 iso- to hypo-intense, T2 hyper-intense and mild and peripherally contrast enhancing following intravenous administration of gadolinium, consistent with fluid accumulation within decellularization sites and a focal disruption of the blood-brain-barrier.

Reference will now be made in detail to various exemplary embodiments of the invention. It is to be understood that the following discussion of exemplary embodiments is not intended as a limitation on the invention, as broadly disclosed above. Rather, the following discussion is provided to give the reader a more detailed understanding of certain aspects and features of the invention.

Before embodiments of the present invention are described in detail, it is to be understood that the terminology used herein is for the purpose of describing particular embodiments only, and is not intended to be limiting. Further, where a range of values is provided, it is understood that each intervening, value, to the tenth of the unit of the lower limit, unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither, or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which the term belongs. Although any methods and materials similar or equivalent to those described herein can be used in the practice or testing of the present invention, the preferred methods and materials are now described. All publications mentioned herein are incorporated herein by reference to disclose and describe the methods and/or materials in connection with which the publications are cited. The present disclosure is controlling to the extent it conflicts with any incorporated publication.

As used herein and in the appended claims, the singular forms "a", "an", and "the" include plural referents unless the context clearly dictates otherwise. Thus, for example, reference to "a pulse" includes a plurality of such pulses and reference to "the sample" includes reference to one or more samples and equivalents thereof known to those skilled in the art, and so forth. Furthermore, the use of terms that can be described using equivalent terms include the use of those equivalent terms. Thus, for example, the use of the term "patient" is to be understood to include the terms "subject", "animal", "human", and other terms used in the art to indicate one who is subject to a medical treatment.

Electroporation is the phenomenon in which permeability of the cell membrane to ions and macromolecules is increased by exposing the cell to short (microsecond to millisecond) high voltage electric pulses. The application of the electric pulses can have no effect, can have a transient effect known as reversible electroporation, or can cause permanent permeation known as irreversible electroporation (IRE), which leads to non-thermal cell death by necrosis.

Davalos, Mir, and Rubinsky (Davalos, R. V. et al., 2005, "Tissue ablation with irreversible electroporation." Annals of Biomedical Engineering, 3(2):223-231) recently postulated and demonstrated that IRE can be used as an independent drug-free tissue ablation modality for particular use in cancer therapy. This minimally invasive procedure involves placing electrodes into or around the targeted area to deliver a series of short and intense electric pulses to induce the irreversible structural changes in the membranes. To achieve IRE, the electric field in the targeted region needs to be above a critical value, which is dependent on a variety of conditions such as tissue type and pulse parameters.

The present invention extends and improves on prior techniques for IRE by providing new methods and devices for IRE treatment of neoplasias, including those associated with brain cancer. Because the brain is susceptible to small fluctuations in temperature, the present invention provides devices and techniques for non-thermal IRE to kill undesirable cells and tissues. In addition, because the brain functions by way of electrical charges, the present invention provides devices and techniques that limit or precisely control the amount of electrical charge delivered to tissue. Other neoplasias also show similar sensitivities, and the invention is equally applicable to all neoplasias. To achieve the invention, a device has been developed that contains both conducting and non-conducting surfaces and that is capable of delivering controlled pulses of electricity to tumor tissues while substantially protecting surrounding healthy tissue. In exemplary embodiments, the device has a laminate structure of at least one electrically conductive and at least one electrically insulative material. In some exemplary embodiments, the device has at least two concentric disk electrodes separated by an insulating material similar in dimensions to those already used in deep brain stimulation (SDBS). DBS is an FDA approved therapy that alleviates the symptoms of otherwise treatment-resistant disorders, such as chronic pain, Parkinson's disease, tremor, and dystonia. The Examples, below, present results demonstrating that an IRE procedure does not induce substantial thermal effects in the brain and bone marrow, and delivers electrical charges to highly defined regions of tissues, supporting the conclusion that IRE can be used as a minimally invasive surgical technique for the treatment of brain cancer and other diseases and disorders involving aberrant cell mass development. The methods employ the unique designs discussed herein, which provide improved controlled delivery of electrical pulses with controlled three-dimensional patterns and controlled thermal outputs. The present devices and systems provide surgical tools and methods for IRE treatment of subcutaneous tumors that expand the application space for this new technology, with the potential to treat a number of solid tumor cancers, including brain, liver, prostate and pancreatic adenocarcinoma and non-solid, tumor cancers, including all types of leukemia.

The following detailed description focuses mainly on devices, systems, and methods for treatment of brain cancer. However, those of skill in the art will recognize that the concepts discussed have equivalent application to other diseases and disorders involving aberrant cell growth and/or production of deleterious cell masses on or by organs and tissues.

While the prognosis for many patients has improved with new drugs and radiosurgery, options to treat primary brain tumor patients are limited because of the need for techniques to be non-thermal, i.e., not propagate a convective hot spot in normal brain tissue not being treated. The current invention allows for IRE as an extremely useful, minimally invasive surgical technique for the treatment of brain cancer and other neoplasias. The present designs for a surgical tool/treatment system for brain cancer is readily translated into the development of tools for other types of cancer.

As mentioned above, the present invention provides a method for treating aberrant cell growth in animals. The aberrant cell growth can be any type of aberrant cell growth, but in exemplary embodiments detailed herein, it is generally described in terms of tumors, such as brain tumors. In general the method of treating comprises temporarily implanting one or more electrodes, which may be present on the same or different devices, into or immediately adjacent a neoplasia, and applying an electrical field to the neoplasia in multiple pulses or bursts over a prescribed or predetermined period of time to cause irreversible cell death to some or all of the neoplastic cells. Preferably, irreversible damage to non-neoplastic cells in proximity to the treated neoplastic cells is minimal and does not result in significant or long-lasting damage to healthy tissues or organs (or a significant number of cells of those tissues or organs). According to the method of the invention, cell killing is predominantly, essentially, or completely due to non-thermal effects of the electrical pulsing. The method further comprises removing the electrode(s) after suitable treatment with the electrical fields. In preferred embodiments, the method also includes administering to the subject being treated an effective amount of a nanoparticle such that the nanoparticles infiltrate the neoplastic cell mass that is to be treated with IRE. The presence of the nanoparticles at the site of treatment improves treatment outcome. As a general matter, because the method involves temporary implantation of relatively small electrodes, it is minimally invasive and does not result in the need for significant post-treatment procedures or care. Likewise, it does not result in significant ancillary or collateral damage to the subject being treated.

In practicing the method, the number of electrodes, either on a single or multiple devices, used can be selected by the practitioner based on the size and shape of the neoplasia to be treated and the size and shape of the electrode. Thus, embodiments of the invention include the use of one, two, three, four, five, or more electrodes. Each electrode can be independently sized, shaped, and positioned in or adjacent the tissue to be treated. In addition, the number and spacing of electrodes on a single device can be adjusted as desired. As detailed, below, the location, shape, and size of electrodes can be selected to produce three-dimensional killing zones of numerous shapes and sizes, allowing for non-thermal treatment of neoplasias of varying shapes and sizes.

Surprisingly, it has been found that pulse durations for ablation of neoplasias, and in particular solid tumors, can be relatively short, thus reducing, the probability of generation of thermal conditions and excessive charges that cause collateral damage to healthy tissues. More specifically, the present invention recognizes for the first time that, in contrast to prior disclosures relating to IRE, the pulse length for highly efficient tissue ablation can be lower than 100 microseconds (100 μs). Indeed, it has surprisingly been determined that a pulse length of 25 microseconds (25 μs) or lower can successfully cause non-thermal cell death. Thus, in embodiments, the method of treatment uses pulse lengths of 10 μs, 15 μs, 20 μs, 25 μs, 30 μs, 35 μs, 40 μs, 45 μs, 50 μs, 55 μs, 60 μs, 65 μs, 70 μs, 75 μs, 80 μs, 85 μs, or 90 μs. Preferably, to most effectively minimize peripheral damage due to heat, pulse lengths are limited to 90 μs or less, for example 50 μs or less, such as 25 μs. By reducing the pulse length, as compared to prior art techniques for IRE, larger electric fields can be applied to the treatment area while avoiding, thermal damage to non-target tissue (as well as to target tissue). As a result of the decreased pulse length and concomitant reduction in heat production, the methods of the invention allow for treatment of tissues having higher volumes (e.g., larger tumors, non-solid tumors) than possible if prior art methods were to be employed for in vivo treatment of tumors.

It has also been determined that voltages traditionally used for IRE are too high for beneficial treatment of tumors in situ. For example, typically, IRE is performed using voltages of between 4000 V/cm to 1500 V/cm. The present invention provides for use of voltages of much lower power. For example, the present methods can be performed using less than 1500 V/cm. Experiments performed by the inventors have shown that 2000 V/cm can cause excessive edema and stroke in patients when applied to brain tissue. Advantageously, for treatment of brain tumors, applied fields of about 500 V/cm to 1000 V/cm are used. Thus, in general for treatment of brain tumors, applied fields of less than 1000 V/cm can be used.

Further, it has been discovered that the number of electrical pulses that can be applied to successfully treat tumors can be quite high. Prior art methods of using IRE for various purposes included, the use of relatively few pulses, for example 8 pulses or so. Reports of use of up to 80 pulses for IRE have been published; however, to the inventors' knowledge, a higher number of pulses has not been recommended. The present invention provides for the use of a relatively high number of pulses, on the order of 90 pulses or greater. For example, in exemplary embodiments, 90 pulses are used. Other embodiments include the use of more than 90 pulses, such as 100 pulses, 110 pulses, or more. Moderately high numbers of pulses, such as those in the range of 50-90 pulses can also be used according to the invention, as well as moderate numbers of pulses, such as those in the range of 20-50 pulses.

According to the method of the invention, cycle times for pulses are set generally about 1 Hz. Furthermore, it has been found that alternating polarity of adjacent electrodes minimizes charge build up and provides a more uniform treatment zone. More specifically, in experiments performed by the inventors, a superficial focal ablative IRE lesion was created in the cranial aspect of the temporal lobe (ectosylvian gyms) using the NanoKnife®B (Angiodynamics, Queensbury, N.Y.) generator, blunt tip bipolar electrode (Angiodynamics, No. 204002XX) by delivering 9 sets of ten 50 μs pulses (voltage-to-distance ratio 2000 V/cm) with alternating polarity between the sets to prevent charge build-up on the stainless steel electrode surfaces. These parameters were determined from ex-vivo experiments on canine brain and they ensured that the charge delivered during the procedure was lower than the charge delivered to the human brain during electroconvulsive therapy (an FDA approved treatment for major depression). Excessive charge delivery to the brain can induce memory loss, and thus is preferably avoided.

The method of the invention encompasses the use of multiple electrodes and different voltages applied for each electrode to precisely control the three-dimensional shape of the electric field for tissue ablation. More specifically, it has been found that varying the amount of electrical energy emitted by different electrodes placed in a tissue to be treated allows the practitioner to finely tune the three-dimensional shape of the electrical field that irreversibly disrupts cell membranes, causing cell death. Likewise, the polarity of electrodes can be varied to achieve different three-dimensional electrical fields. Furthermore, one of the advantages of embodiments of the invention is to generate electric field distributions that match complex tumor shapes by manipulating the potentials of multiple electrodes. In these embodiments, multiple electrodes are energized with different potential combinations, as opposed to an "on/off" system like radio frequency ablation, to maximize tumor treatment and minimize damage to surrounding healthy tissue.

According to the method of the invention, the separation of the electrodes within or about the tissue to be treated can be varied to provide a desired result. For example, the distance between two or more electrodes can be varied to achieve different three-dimensional electrical fields for irreversible disruption of cell membranes. The three-dimensional shape can thus be set to ablate diseased tissue, but partially or completely avoid healthy tissue in situations where the interface between healthy and diseased tissue shows a complex three dimensional shape.

The methods of the invention are well suited for treatment of solid tumors and other neoplasias using non-thermal IRE. To better ensure that cell ablation is a result of non-thermal effect, and to better protect healthy tissue surrounding the site of treatment, the method can further comprise cooling the electrodes during the treatment process. By applying a heat sink, such as a cooling element in an electrode (discussed below), generation of heat in and around tissue in close proximity to the electrodes can be minimized, resulting in a more consistent application of non-thermal IRE to the tissue and as more controlled application of cell killing to only those tissues desired to be treated.

The method of the invention, in embodiments, includes the use of electrodes of different sizes and shapes. Studies performed by the inventors have shown that the electrical field distribution may be altered by use of electrodes having different diameters, lengths, and shapes. Thus, the use of different sizes and shapes of conducting surfaces can be used to control the electrical fields used for cell ablation. In certain embodiments, the method includes the use of a variable size electrode. For example, an electrode may be used that, in one configuration has a relatively small diameter, which is used for minimally invasive implantation of the electrode into the site to be treated. Once inserted, a sheath or other covering can be retracted to allow expansion of the electrode tip to a different size for application of the electric field. After treatment, the sheath can be moved to cover the tip again, thus reducing, the size of the tip to its original size, and the electrode withdrawn from the treated tissue. The expandable element can be thought of as a balloon structure, which can have varying diameters and shapes, depending on original material shape and size.

Figure 18:
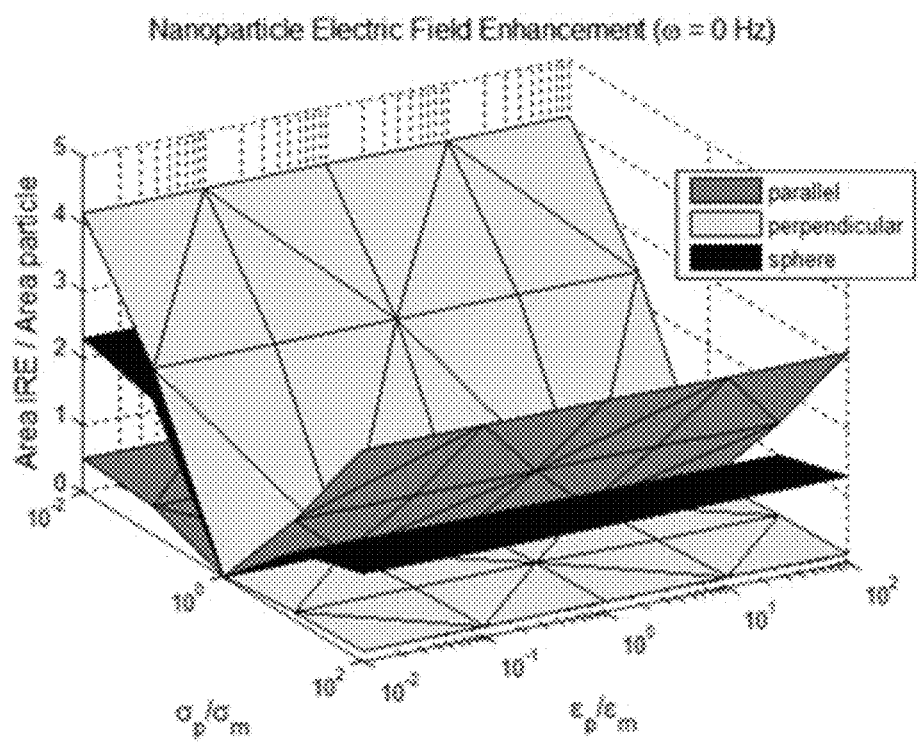
FIG. 18 depicts the results of a finite-element model showing the IRE treatment area (electric field >600 V/cm) normalized, by the area of the nanoparticle for varying ratios of conductivity (a) and permittivity (c) between the nanoparticle (p) and surrounding medium (m) when the nanoparticles are placed in a uniform electric field of 500 V/cm. The results were obtained by solving the complex Laplace equation in a FEM with an adaptive mesh and performing a subdomain integration within the nanoparticle and its surrounding medium.

In embodiments, the method of the invention comprises the use of nanoparticles, as shown, for example, in FIG. 18. In the presence of an electric field, a nanoparticle, such as a nanosphere or nanorod, experiences a charge polarization. In the case of a conductive nanorod, this polarization is larger in the direction parallel to the axis than the radial direction, and charge accumulates at the tips, forming a dipole. The dipole serves to simultaneously align the nanoparticle in the direction of the electric field and locally amplify the electric field at the nanoparticle tips. In this scenario, the nanorod behaves like a downscaled dipole antenna from classical antenna theory, which indicates that a higher aspect ratio nanoparticle is more effective at concentrating the field. Conversely, if an insulative nanorod is employed, a large field enhancement can still be obtained if the long dimension of the particle is oriented perpendicular to the applied electric field, and a higher aspect ratio particle still serves to enhance this effect. Field enhancement can also be obtained for a conductive and insulative sphere, while to a lesser extent than the scenarios described above. However, when multiple spheres are employed, the high surface charge density concentrates the electric field between the spheres, as shown, for example, in FIG. 20. In other words, the field enhancement of closely spaced spheres becomes very strong, and is on the order of that seen in prolate nanoparticles. Examples of nanoparticles include, but are not limited to, fullerenes (a.k.a. $C_{60}$, $C_{70}$, $C_{76}$, $C_{80}$, $C_{84}$), endohedral metallofullerenes (EMI's) buckyballs, which contain additional atoms, ions, or clusters inside their fullerene cage), trimetallic nitride templated endohedral metallofullerenes (TNT EMEs, high-symmetry four-atom molecular cluster endohedrals, which are formed in a trimetallic nitride template within the carbon cage), single-walled and mutli-walled carbon nanotubes, branched and dendritic carbon nanotubes, gold nanorods, silver nanorods, single-walled and multi-walled boron/nitrate nanotubes, carbon nanotube peapods (nanotubes with internal metallofullerenes and/or other internal chemical structures), carbon nanohorns, carbon nanohorn peapods, liposomes, nanoshells, dendrimers, quantum dots, superparamagnetic nanoparticles, nanorods, and cellulose nanoparticles. The particle embodiment can also include microparticles with the capability to enhance IRE effectiveness or selectivity. Other non-limiting exemplary nanoparticles include glass and polymer micro- and nano-spheres, biodegradable PLGA micro- and nano-spheres, gold, silver, carbon, and iron nanoparticles.

As should be evident by the present disclosure, the invention also encompasses use of particles on the micrometer scale in addition to the nanometer scale. Where microparticles are used, it is preferred that they are relatively small, on the order of 1-50 micrometers. For ease of discussion, the use herein of "nanoparticles" encompasses true nanoparticles (sizes of from about 1 nm to about 1000 nm), microparticles (e.g., from about 1 micrometer to about 50 micrometers), or both. In preferred embodiments, the nanoparticles do not comprise carbon and/or are not carbon nanotubes.

Nanoparticles, in embodiments, may be modified with surface chemistry to cause the localized destruction of targeted cells, while leaving untargeted cells intact. The surface of nanoparticles can be functionalized to target specific cancer cells with various antibodies and chemical compounds. Due to the electric field enhancement and the ability of functionalized nanoparticles to target cancer cells, electric pulse protocols can be optimized, such that only cancer cells with selectively bound nanoparticles experience a localized electric field above the threshold for achieving IRE, and healthy cells remain intact. This methodology can be employed to purge a subject of cancer cells within and beyond the treatment margin, while maintaining proper organ function. Tumors can be comprised of as much as 80% healthy cells, and selectively destroying the cancer cells, including cancer stem cells (CSCs), reduces the potential for tumor recurrence.

Figure 17:
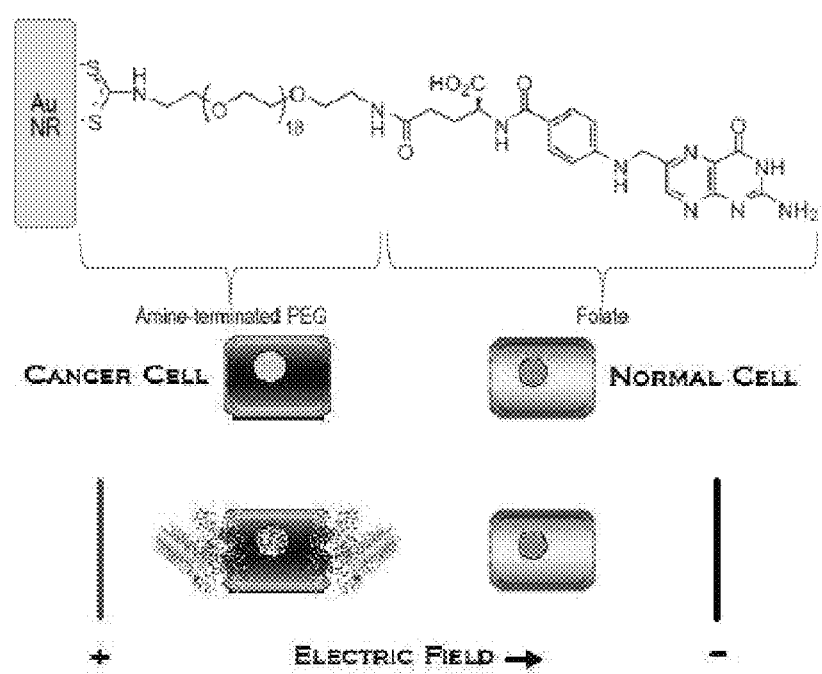
FIG. 17 depicts a gold nanorod (Au NR) with modified surface chemistry that can be used to selectively target and kill a cancer cell when placed in an electric field.

There are many examples of nanoparticle targeting techniques known in the art. For example, folic acid conjugations can be used to selectively bind to cancer cells with up-regulated folate receptors, such as breast and brain cancer cells (see FIG. 17). As another example, antibodies can be conjugated to selectively bind to cancer cells presenting distinct antigens, such as leukemic cells. As a further example, the simple tendency of well suspended nanoparticles (coated with polymers) to diffuse into tumor masses over time following systemic delivery can be employed as a nanoparticle targeting technique.

The methods of the invention comprise, in embodiments, treatment of tissue surrounding neoplastic tissue, particularly in the context of solid tumors. The surrounding tissue is treated by way of reversible electroporation. As such, bioactive agents can be introduced into the reversibly electroporated cells. In such embodiments, additional cell killing, under controlled conditions, can be effected in healthy tissue. Such a treatment is preferred when treating highly aggressive malignant: tumors, which often show invasion of healthy tissue surrounding the tumor. Alternatively, the bioactive agents can provide a protective effect to cells in which they are introduced via reversible electroporation.

In embodiments, the method for treating aberrant cell growth in animals is a method of treating a subject suffering from a neoplasia. It thus may be a method of treating a subject suffering from cancer. Using different terminology, the method can be a method of treating a neoplasia or a method of treating cancer. As such, the method can be a method of treating either a benign tumor or a malignant tumor. In embodiments, the method is best suited for treatment of solid tumors. In exemplary embodiments, the method is a method of treating a subject suffering from a brain tumor, such as brain cancer.

In clinical settings, the method of treating according to the invention can have ameliorative effects or curative effects. That is, a method of treating a subject can provide a reduction in neoplastic cell growth of a tumor, a reduction in tumor size, or total ablation of the tumor and/or neoplastic cells.

The method of the invention can include as single round of treatment or two or more rounds of treatment. That is, the method of cell ablation, either intentionally or as a result of tumor size or shape, can result in less than complete destruction of a tumor. In such a situation, the method can be repeated one or more times to effect the desired level of tumor reduction. As the method of the invention is relatively minimally: invasive, multiple rounds of treatment are not as harmful to the patient as multiple rounds of traditional surgical intervention.

The method of the invention can be part of a multi-modal treatment. The method thus may comprise other cell-killing techniques known in the art. For example, the method may further comprise exposing the neoplastic cells or tissue to radiation, or treating the patient with a chemotherapeutic agent. It likewise may be performed after or between surgical intervention to remove all or part of a tumor. Those of skill in the art are fully are of the parameters for treatment with other modalities; thus, details of those treatment regimens need not be detailed herein.

The method of the invention is implemented using devices and systems. The devices according to the invention are suitable for minimally invasive temporary implantation into a patient, emission of a tissue-ablating level of electricity, and removal from the patient. The device according to the invention thus may be used in the treatment of neoplasias and the treatment of patients suffering from neoplasias. The devices can take multiple forms, based on the desired three-dimensional shape of the electrical field for cell killing. However, in general, the devices include two or more regions of differing conductivity. In some embodiments, the device comprises alternating regions of conductivity, for example a region of electrical conductivity, which is adjacent a region of electrical non-conductivity, which is adjacent a different region of conductivity. In embodiments, the device comprises two or more layers of conductive and insulative materials, in a laminate structure with alternating conductive properties. To protect tissue that is not to be treated, the outer layer can be insulative except, at the region where treatment is to be effected. According to embodiments of the device, the amount of conductive material exposed to the tissue to be treated can be adjusted by a movable non-conductive element disposed on the outer surface of the device.

Further, in general, the device takes a rod-like shape, with one dimension (i.e., length) being substantially longer than the other (i.e., width or diameter). While exemplary embodiments are configured in a generally cylindrical shape, it is to be understood that the cross-sectional shape of the electrode can take any suitable geometric shape. It thus may be circular, square, rectangular, oval, elliptical, triangular, pentagonal, hexagonal, octagonal, etc.

The devices of the invention comprise one or more electrodes, which are electrically conductive portions of the device. The devices are thus electrically conductive elements suitable for temporary implantation into living tissue that are capable of delivering an electrical pulse to the living tissue. The device of the invention has a proximal end and a distal end. The proximal end is defined as the end at which the device is attached to one or more other elements, for control of the function of the device. The distal end is defined by the end that contacts target tissue and delivers electrical pulses to the tissue. The distal end thus comprises an exposed or exposable electrically conductive material for implantation into a target tissue typically, the distal end is described as including a "tip" to denote the region of the distal end from which an electrical pulse is delivered to a tissue. The device further comprises at least one surface defining the length and circumference of the device.

In exemplary embodiments, the device comprises a laminate structure, with alternating conductive and non-conductive or insulative layers expanding outward from the proximal-distal center axis to the surface of the device. In typical embodiments, the center most layer, which shows the smallest diameter or width, is electrically conductive and comprises a part of the electrode tip. However, in alternative embodiments, the center-most layer is an open channel through which a fluid may be passed or through which additional physical elements may be placed. Yet again, the center-most layer may comprise an insulative material. In embodiments comprising, a laminate structure, the structure can provide a more customizable electric field distribution by varying the separation distances between electrically conductive regions. Alternatively, in embodiments, certain electrically conductive regions can be exposed or concealed by movement of an outer, non-conductive sheath. In embodiments that do not comprise a laminate structure, the separation lengths can be achieved by disposing on the surface non-conductive materials at various regions.

In some embodiments, one or more substantially open channels are disposed along the center axis or in place of one of the conductive or insulative layers. The channel(s) may be used as heat sinks for heat produced by the device during use. In embodiments, water or another fluid is held or entrained in the channel to absorb and/or remove heat.

The device of the invention comprises an electrode tip at the distal end. The electrode tip functions to deliver electrical pulses to target tissue. The tip may be represented by a single conductive layer of the device or may be represented by two or more conductive layers that are exposed to the tissue to be treated. Furthermore, the tip may be designed to have any number of geometrical shapes. Exemplary embodiments include tips having a needle-like shape (i.e., electrical pulses emanate from a small cone-like structure at the distal end of the device) or having a circular shape (i.e., electrical pulses emanate from the cylindrical outer surface of the device, which is a section of the device where the outer insulative layer has been removed to expose the next layer, which is conductive). For use in treatment of brain tumors, the tip advantageously comprises a blunt or rounded end to minimize laceration of brain tissue. In embodiments, the rounded or blunt end comprises a hole that allows for a sharp or needle-like structure to be deployed into tumor tissue at the appropriate time.

The device comprises a proximal end, which generally functions for attachment of the device to a power source/controller and a handle. The proximal end thus may comprise connections for electrical wires that run from the power source/controller to the electrically conductive layers of the device. Standard electrical connections may be used to connect the conductive elements to the wires. In embodiments, the device is attached to a handle for ease of use by a human. While, not limited in the means for attaching the device to the handle, in embodiments, the connection is made by way of a friction fit between the outer surface of the device and the handle, for example by way of an insulative O-ring (e.g., a Norprene O-ring) on the handle. In other embodiments, the device comprises, on its outer surface, ridges or other surface features that mate with surface features present on the handle. In yet other embodiments, the proximal end comprises one or more structures that allow for controlled movement of the outer surface along the length of the device. In such embodiments, the outer surface will comprise an outer sheath that is electrically non-conductive, and which surrounds an electrically conductive layer. Using the structures at the proximal end, the outer sheath may be moved, relative to the rest of the device, to expose or conceal varying portions of the electrically conductive material beneath it. In this way, the amount of surface area of the conductive material at the tip can be adjusted to provide a desired height of exposure of tissue to the electrode tip. Of course, other structures for securely fastening the device to a holder may be used, such as clips, set screws, pins, and the like. The device is not limited by the type of structure used to connect the device to the holder.

The device of the invention can be designed to have any desired size. Typically, it is designed to be minimally invasive yet at the same time suitable for delivery of an effective electrical field for IRE. The diameter or width is thus on the order of 0.5 mm to 1 cm. Preferably, the diameter or width is about 0.5 mm to about 5 mm, such as about 1 mm, 2 mm, 3 mm, or 4 mm. The length of the device is not particularly limited, but is generally set such that a surgeon can use the device comfortably to treat tumors at any position in the body. Thus, for human use, the device is typically on the order of 40 cm or less in length, such as about 30 cm, 25 cm, or 15 cm, whereas for veterinary use, the length can be much larger, depending on the size of animal to be treated. For treatment of human brain tumors, the length can be on the order of 40 cm.

In some embodiments, the device, or a portion of it, is flexible. A flexible device is advantageous for use in accessing tumors non-invasively or minimally invasively through natural body cavities. In embodiments where the device or a portion of it is flexible, the shape of the device can change based on contact with body tissues, can be pre-set, or can be altered in real-time through use of wires or other control elements, as known in the art, for example in use with laparoscopic instruments.

The device of the invention can be part of a system. In addition to the device, the system can comprise a handle into or onto which the device is disposed. The handle can take any of a number of shapes, but is generally designed to allow a surgeon to use the device of the invention to treat a patient in need. It thus typically has a connector for connecting the device to the holder, and a structure for the surgeon to grasp and maneuver the device. The handle further can comprise a trigger or other mechanism that allows the surgeon to control delivery of electrical pulses to the device, and thus to the tissue to be treated. The trigger can be a simple on/off switch or can comprise a variable control that allows for control of the amount of power to be delivered, to the device. Additionally, the handle may be created in such a manner that it may be attached to additional pieces of equipment, such as ones that allow precise placement of the electrode relative to an inertial or the patient's frame of reference, allowing steady and accurate electrode positioning throughout an entire procedure, which may entail the application of electric pulses in addition to radiotherapy, imaging, and injections (systemically and locally) of bioactive agents. Furthermore, the handle may be attached to machines that are operated remotely by practitioners (e.g., the Da Vinci machine).

The system can further comprise a power source and/or a power control unit. In embodiments, the power source and control unit are the same object. The power source provides electrical power to the device, typically by way of an electrical connection through the handle. The power source can be any suitable source that can deliver the proper amount of electrical power to the device of the invention. Suitable power sources are commercially available, and the invention is not limited by the type or manufacturer. The power control unit provides the user with the ability to set the power output and pulse time for electrical pulses to be delivered to the device, and thus to the tissue to be treated. Suitable control units are commercially available, and the invention is not limited by the type or manufacturer. For example, an appropriate power source/controller is available front Angiodynamics (Queensbury, N.Y.).

The device of the invention can be disposable or reusable. Where the device is designed to be reusable, it is preferably fabricated from materials that can be sterilized multiple times without destruction of the device. For example, the device can be fabricated from rust-resistant metals or alloys, such as stainless steel, and plastic or other synthetic polymeric materials that can withstand cleaning and sterilization. Exemplary materials are those that can be subjected to detergents, steam heat (e g., autoclaving), and/or irradiation for at least one cycle of sterilization. Those of skill in the art can select the appropriate materials without undue experimentation, based on materials used in other medical devices designed to withstand common sterilization techniques.

EXAMPLES

The invention will be further explained by the following Examples, which are intended to be purely exemplary of the invention, and should not be considered as limiting the invention in any way.

As a general background to the Examples, it is noted that the inventors and their colleagues have successfully demonstrated decellularization using IRE 1) in vivo and ex vivo, 2) to show that different tissues can be utilized, 3) to show that the area affected can be predicted using numerical modeling, 4) to show how numerical modeling can be used to ensure the ECM, blood vessels, and neural tubes are not thermally damaged, 5) while the organ was attached to a perfusion system, 6) while demonstrating preservation of major vasculature and ECM, and 7) with verification through imaging.

Example 1

Example IRE Performance Indicia

To illustrate 1) the possibility to monitor creation of a cell-free tissue section in brain in real-time using imaging techniques, 2) the variety of tissues that can be used, and 3) how to preserve vasculature, a healthy female purpose bred beagle was used. Nine sets of ten pulses were delivered with alternating polarity between the sets to minimize charge build-up on the electrode, surfaces. The maximum voltage-to-distance ratio used was 2000 V/cm because the resulting current did not exceed 2 amps. The charge that was delivered to the brain during the IRE procedure was 22.5 mC, assuming ninety pulses (50 µs pulse durations) that would result from a maximum hypothetical current of 5 amps.

TABLE 1

IRE pulse parameters

| ELECTRODES | EXPOSURE LENGTH [mm] | GAP DISTANCE [mm] | VOLTAGE [V] | VOLTAGE TO DISTANCE RATIO [V/cm] | PULSES | PULSE DURATION [µs] |
|---|---|---|---|---|---|---|
| 1 mm | 5 | 5 | 500 | 1000 | 90 | 50 |
| Bipolar | Standard | 7 | 1600 | 2000 | 90 | 50 |

Method: After induction of general anesthesia, a routine parietotemporal craniectomy defect was created to expose the right temporal lobe of the brain. Two decelluarization sites were performed: 1) a deep lesion within the caudal aspect of the temporal lobe using a monopolar electrode configuration (6 mm electrode insertion depth perpendicular to the surface of the target gyrus, with 5 mm interelectrode distance), and 2) a superficial lesion in the cranial aspect of the temporal lobe using a bipolar electrode (inserted 2 cm parallel to the rostro-caudal length of the target gyms, and 2 mm below the external surface of the gyrus). Intraoperative adverse effects that were encountered included gross microhemorrhages around the sharp monopolar electrode needles following insertion into the gyms. This hemorrhage was controlled with topical application of hemostatic foam. Subject motion was completely obliterated prior to ablating the superficial site by escalating the dose of atracurium to 0.4 mg/kg. Grossly visible brain edema and surface blanching of the gyrus overlying the bipolar electrode decelluarization site was apparent within 2 minutes of completion of IRE at this site. This edema resolved completely following intravenous administration of 1.0 g/kg of 20% mannitol. No adverse clinically apparent effects attributable to the IRE procedure, or significant deterioration in neurologic disability or coma scale scores from baseline evaluations were observed. However, the results indicated to the inventors that a lower voltage would provide adequate results but with less ancillary trauma to the brain.

Methods to monitor creation of cell-free tissues in vivo: A unique advantage of IRE to ablate tissues in vivo is its ability to be monitored in real-time using imaging techniques, such as electrical impedance tomography, MRI, and ultrasound. Below, this Example shows MRI examinations performed immediate post-operatively, which demonstrate that IRE decelluarization zones were sharply demarcated. (FIGS. 1A-C).

Figure 1B:
Figure 1C:
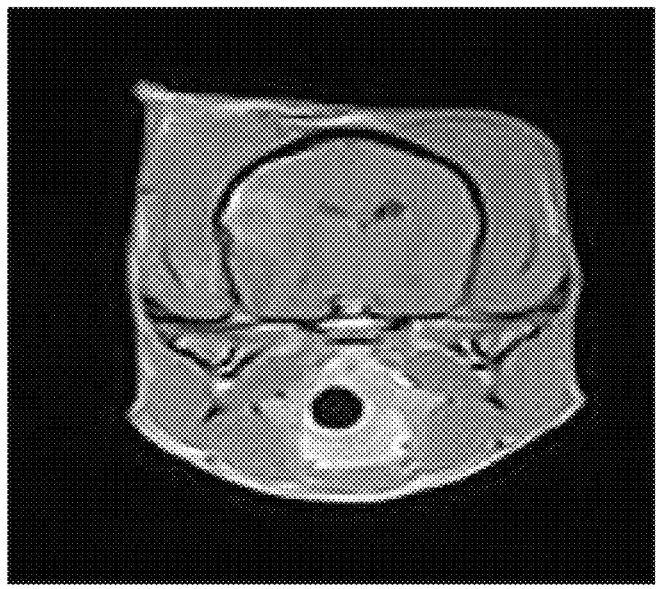
Figure 2:
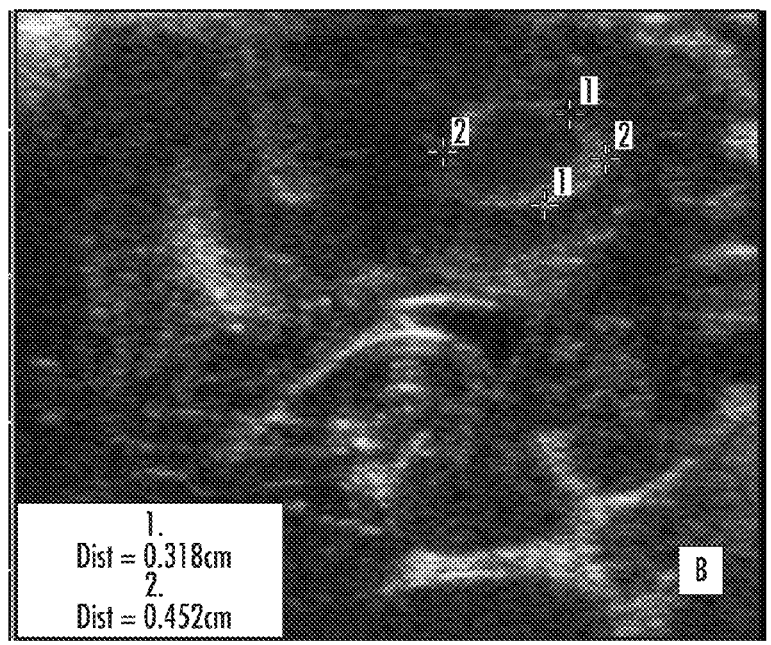
FIG. 2 shows an ultrasound image of brain tissue 24 hour post-IRE treatment. The IRE decelluarization zone is clearly visible as a well demarcated, hypoechoic circular lesion with a hyperechoic rim.

As shown in FIGS. 1A-C, neurosonography performed intraoperatively and at hour and 24 hours post-procedure demonstrated clearly demarcated decellttlarization zones and visible needle tracts within the targeted brain parenchyma. Intraoperatively and immediately postoperatively, the decelluarization zones appeared as hypoechoic foci with needle tracts appearing as distinct hyperechoic regions (FIG. 2). Neurosonographically, at the 24 hour examination the IRE decellularization zone was hypoechoic with a hyperechoic rim (FIG. 2). Compared to the 1 hour post-operative sonogram, the IRE decelluarization zone appeared slightly larger (1-2 mm increase in maximal, two dimensional diameter), EEG performed in the post-operative period revealed focal slowing of the background rhythm over the right temporal region in association with the decelluarization zones.

Figure 3:
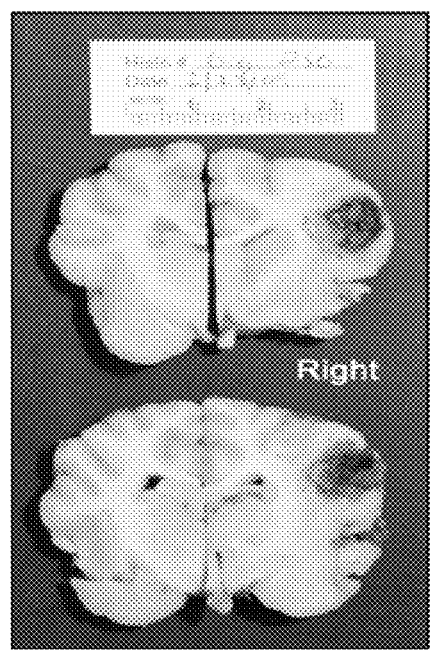
FIG. 3 depicts images of brain tissue after non-thermal IRE treatment.

Macrolevel and histologic verification of treating cells: The brain was collected within 2 hours of the time of death and removed from the cranium. Care was taken to inspect soft tissues and areas of closure created at the time of surgery. The brain, was placed in 10% neutral buffered formalin solution for a minimum of 48 hours. Then, the brain was sectioned at 3 mm intervals across the short axis of the brain, in order to preserve symmetry and to compare lesions. Following gross dissection of fixed tissues, photographs were taken of brain sections in order to document the position and character of lesions, as shown in FIG. 3. Readily apparent in gross photographs of the sectioned brain are lesions created either by the physical penetration of brain substance with electrodes or created by the application of pulse through the electrodes. There are relatively well-demarcated zones of hemorrhage and malacia at the sites of pulse delivery.

Figure 4A:
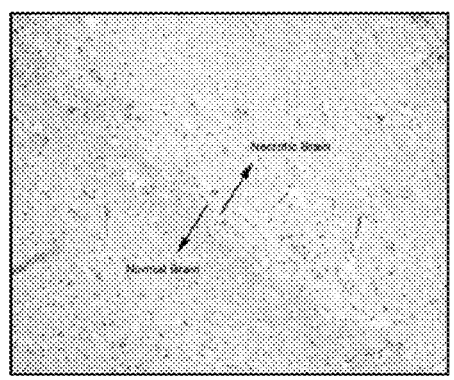
FIG. 4A shows a sharp delineation of brain tissue showing the regions of normal and necrotic canine brain tissue after IRE.
Figure 4B:
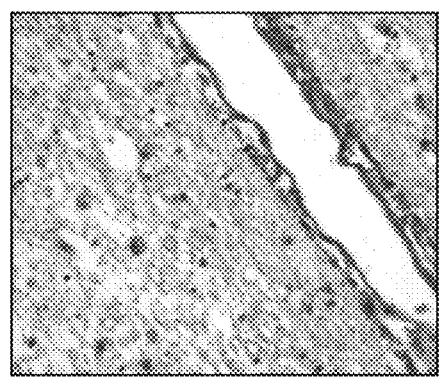
FIG. 4B shows IRE treated brain tissue showing sparing of major blood vessels.

Microscopic lesions correlated well with macroscale appearance. Areas of treatment are represented by foci of malacia and dissociation of white and grey matter. Small perivascular hemorrhages are present and there is sparing of major blood vessels (see FIG. 4B). Notable in multiple sections is a relatively sharp line of demarcation (approximately 20-30 micrometers) between areas of frank malacia and more normal, organized brain substance (see FIG. 4A).

Figure 5:
FIG. 5 shows a three-dimensional MRI source reconstruction of a superficial lesion site.

Analysis to determine IRE threshold: To determine the electric field needed to irreversibly electroporate tissue, one can correlate the lesion size that was observed in the ultrasound and MRI images with that in the histopathological analysis to determine the percentage of lesion growth. Decellularized site volumes can be determined after identification and demarcation of IRE decellularization zones from surrounding brain tissue using hand-drawn regions of interest (ROI). A representative source sample image is provided in FIG. 5.

Example 2

Use of IRE to Kill Brain Cells

There are advantages to a strategy to treat cancer using IRE. IRE to treat cancer has advantages over existing thermal ablation, including the ability to: monitor what area has been irreversibly electroporated in real-time using ultra-sound c other imaging techniques; spare neural tubes and blood vessels, enabling treatment in otherwise inoperable areas; preserve the microvasculature, which promotes rapid healing of the treated volume; predict the affected area using numerical modeling for designing protocols; not be affected by blood flow as is the temperature distribution during thermal therapies; image the success of the treatment using MRI or other imaging techniques; and administer the electric fields in time periods of less than 5 minutes.

The present methods and devices provide a technology for treatment of tumors with IRE. Prior to the present invention, devices designed to irreversibly electroporate deep tissues did not exist. The experiments conducted and reported in the prior art utilized reversible electroporation systems. These devices usually consist of large plate electrodes (intended for transdermal drug delivery), needle electrodes with a large probe (intended for targeting in or for small animal studies), or cuvettes (used for in vitro applications). Applying an electric pulse over the skin presents challenges for deep tissue applications due to the significant voltage drop across the skin, generating, considerable skin damage. (The same issue arises with an organ containing an epithelial layer.) Other devices that use needle electrodes are limited to superficial tumors. Furthermore, these tools have a large mechanical housing making the treatment of subcutaneous tumors impossible without invasive surgery. A tool designed specifically for IRE for subcutaneous delivery of the electric field dramatically enhances the application space of IRE for tissue ablation.

To provide an initial proof of concept, a device according to the invention was used to kill brain cells in vitro. Representing a unique pathobiological phenomenon, high-grade canine gliomas exhibit essentially the same properties as human gliomas, including pathology (markers), genetics, behavior (invasiveness), lack of metastases, and a similar clinical course of the disease. Dogs diagnosed with these tumors have poor prognosis and most are humanely euthanized to prevent further suffering from the progression of the disease. Primary brain tumors (PBTs) account for 1-3% of all deaths in aged dogs where necropsy is performed. The many similarities of glial tumors in people and dogs make these tumors w dogs an excellent translational approach for new diagnostic and treatment methods.

Figure 6:
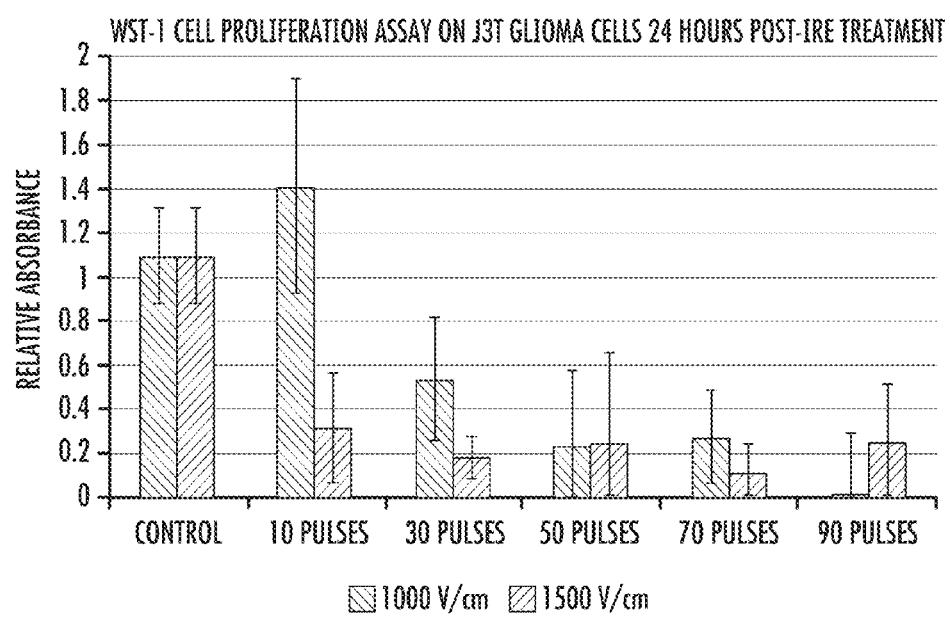
FIG. 6 shows a bar graph indicating results of IRE performed in vitro on J3T glioma cells at different pulse values.

As shown in FIG. 6, cell proliferation of canine glioma cells was significantly reduced or eliminated by treatment with IRE. More specifically. FIGS. 1A-C show the results of J3T glioma cells after treatment with electric, pulses of length 50 microseconds (μs) for 2 electric fields (1000 V/cm and 1500 V/cm) and multiple numbers of pulses. To develop the data shown in the figure, a WST-1 cell proliferation, assay was performed on J3T glioma cells, and the data collected 24 hours post-IRE treatment. Two electric fields (1000 and 1500 V/cm) at 5 different pulse combinations were analyzed. A value of relative absorbance of 0.2 represents 100% cell death. Therefore, it is clear that for as low as 1000 V/cm at 50 pulses total will achieve complete cell death for 50 μs length pulses, proving this a viable IRE treatment parameter.

Example 3

Modeling of Electrode Shape and Placement

The present invention provides simple and elegant minimally invasive microsurgical tools to treat currently inoperable tumors in humans and animals through IRE. Exemplary designs are shown in FIGS. 7A-E, 8A-C, 9A-B, 10, and 11.

FIG. 7A depicts an example of a device 700 according to one embodiment of the invention. This embodiment is fully compatible with existing, electroporation electronics and comprises a surgical probe/electrode tip 710 at its distal end, which includes both ground electrodes 711 and energized electrodes 712. The device further comprises a universal connector 750 at its proximal end. The device also comprises internal wiring 770 to deliver electrical impulses to the tip 710. The body of the device is defined by surface 718.

The size and shape of the IRE area is dictated by the voltage applied and the electrode configuration and is readily predictable through numerical modeling. Therefore, different surgical tips can be fashioned to achieve the same therapeutic result. For example, tip 710 can comprises retractable conductive spikes 713 emanating from a blunt end tip 710 and disposed, when deployed, at an acute angle to tip 710 (see FIG. 7B). Alternatively, tip 710 can be fashioned as a point or needle, and can include retractable accordion-type conductive elements 714 (see FIG. 7C). In other exemplary embodiments, tip 710 can comprise multiple retractable spikes 715 that, when deployed, emanate at 90° C. from tip 710 (see FIG. 7D). Yet again, tip 710 can comprise retractable conductive spikes 716 emanating from a needle-end tip 710 and disposed, when deployed, at an acute angle to tip 710 (see FIG. 7E). FIGS. 7B, 7D, and 7E show probes with parallel circular channels 717 of approximately 1 mm that protrude through the length of the electrode holder. Each channel has the capability of guiding individual 1 mm electrodes to the treatment area. Towards the bottom of the holder, the channels deviate from their straight path at a specific angle. The electrodes can be Platinum/Iridium with an insulating polyurethane jacket to ensure biocompatibility, similar to materials that are used in DBS implants. Different protrusion depths of the electrodes within the tissue as well as the applied voltage can be used to control the size of the treated area.

The devices can comprise interchangeable surgical tips, allowing for versatility in creating a device well suited for different tissues or different sized or shaped tumors. Varying electrode diameters (varied in part by selection of the type and length of deployable spikes) and separation distances will be sufficient to ablate the majority of tumors about or smaller than 3 cm by selecting the appropriate voltages to match different tumor sizes and shapes. As shown in later figures, some of the embodiments of the device comprise an element at the tip to introduce anti-cancer drugs for ECT, cytotoxic proteins, or other bioactive agents into the targeted area.

While not depicted in detail, embodiments of the device comprise durable carbon coatings over portions of the device that act both to insulate normal tissue and to increase the efficiency of IRE pulsing.

With general reference to FIGS. 7A-D, in brain tumor IRE treatment, for example, a single blunt-end device, with embedded active and ground electrodes can be used. In an embodiment not particularly depicted in the figures, the device contains a primary blunt-end tip with a hole disposed in the end, for insertion through delicate, soft brain tissue. The device of these embodiments further comprises a secondary sharp tip, which can be deployed through the hole in the blunt-end primary tip, which allows for penetration into the tumor tissue, which can be substantially more dense or hard, and not easily punctured by a blunt-end tip. In general, the device of the invention is typically similar in dimensions (2 mm) to those already used in deep brain stimulation (DBS), which ensures that they are feasible for surgical applications. DBS uses electrodes in an FDA approved therapy to alleviate the symptoms of otherwise treatment-resistant disorders, such as Parkinson's disease and dystonia. Furthermore, the electrode positioning frame, which is used in stereotactic surgery in conjunction with imaging systems, can be used to position the surgical probes and ensure that the position of the electrodes is optimal. Simulations of a design similar to the one in FIG. 7A show treatment volumes comparable to typical brain tumors.

Figure 8A:
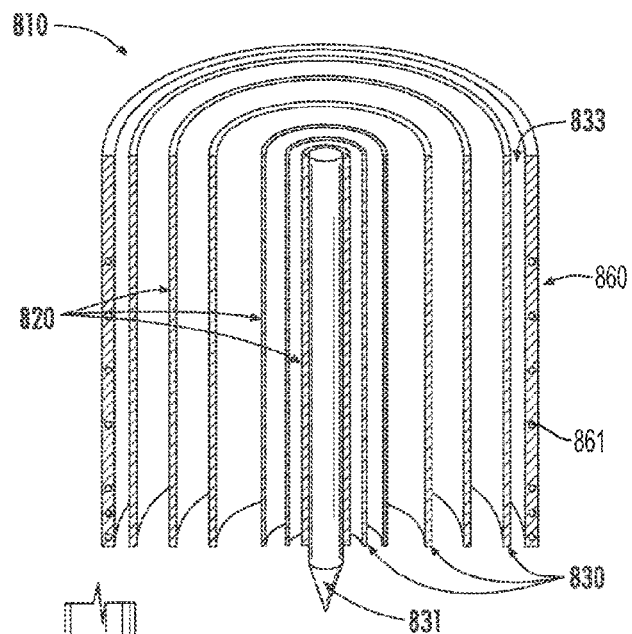
FIGS. 8A-SC depict an expanded view of an electrode tip according to one embodiment of the invention.
Figure 8B:
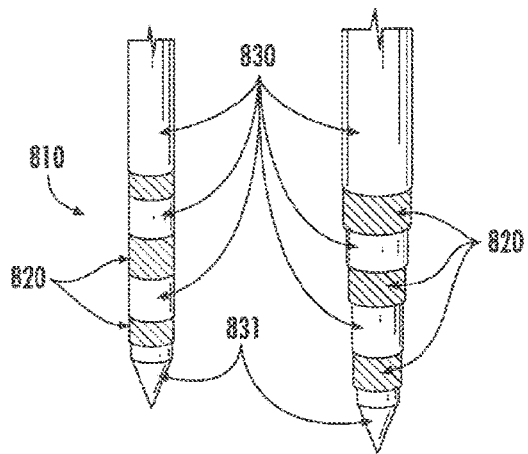
FIG. 8B depicts a side view of the electrode of FIG. 8A, showing the various layers in cut-away fashion.
Figure 8C:
FIG. 8C depicts the electrode tip viewed along: the proximal-distal plane.

FIGS. 8A-C depict in more detail an embodiment of a tip 810 according to the invention. FIG. 8A depicts an exploded view of tip 810, showing multiple concentric layers of conducting 820 and non-conducting 830 materials. An outer layer or sheath 860 of non-conducting, material is shown with perforations 861. The outer, perforated layer 860 is disposed around the concentric rings of materials, to allow for delivery of bioactive substances to cells in proximity to the device when in use. Perforated layer 860 may be disposed in full, direct contact with the outermost layer of the concentric ring structure, or may be substantially separated from the ring structure by chamber 833 that holds cooling fluid.

As shown in the cut-away depiction in FIG. 8A, device tip 819 has multiple alternating layers of conducting 820 and non-conducting 830 materials surrounding an non-conducting inner core 831. In FIG. 8B, the top and bottom conducting regions 820 are energized electrodes while the middle conducting region 820 is a ground electrode. The present invention provides the conducting and non-conducting (insulative) regions in varying lengths to fine tune electrical field generation. More specifically, using imaging techniques directed at the tumor to be treated, a surgeon can determine what type of electrical field is best suited for the tumor size and shape. The device can comprise one or more movable elements on the surface of the tip (not depicted) or can be designed such that one or more of the alternating conducting 820 or non-conducting 830 elements is movable. Through movement and setting of the outer element(s) or inner elements 820 or 830, the surgeon can configure the device to deliver a three-dimensional electrical killing field to suit the needs of the particular situation.

FIG. 8C depicts the concentric, laminate structure of tip 810, viewed from the distal end along the distal-proximal axis, showing again the laminate nature of the device.

In addition to changing charges, adapting the physical dimensions of the probe also allows flexibility in tailoring the treatment area to match the dimensions of the tumor. By altering the electrode parameters, including diameter, length, separation distance, and type, it is possible to conveniently tailor the treatment to affect only specific, targeted regions. In addition, developing an electrode capable of altering and adapting to these dimensional demands greatly enhances its usability and adaptability to treatment region demands.

Example 4

Hollow Core Device

Many IRE treatments may involve coupled procedures, incorporating several discrete aspects during the same treatment. One embodiment of the invention provides a device with a needle-like tip 910 with an incorporated hollow needle 990 with either an end outlet 991 (shown in FIG. 9A) or mixed dispersion regions 961 (shown in FIG. 9B). Such a configuration allows for highly accurate distribution of injectable solutions, including, those comprising bioactive agents. Use of such a device limits the dose of treatment required as well as ensures the correct placement of the materials prior to, during, and/or after the treatment. Some of the possible treatment enhancers that would benefit from this technology are: single or multi-walled carbon nanotubes (CNTs) chemotherapeutic agents; conductive, gels to homogenize the electric field; antibiotics; anti-inflammatories; anaesthetics; muscle relaxers; nerve relaxers; or any other substance of interest.

Figures 9A, 9B:
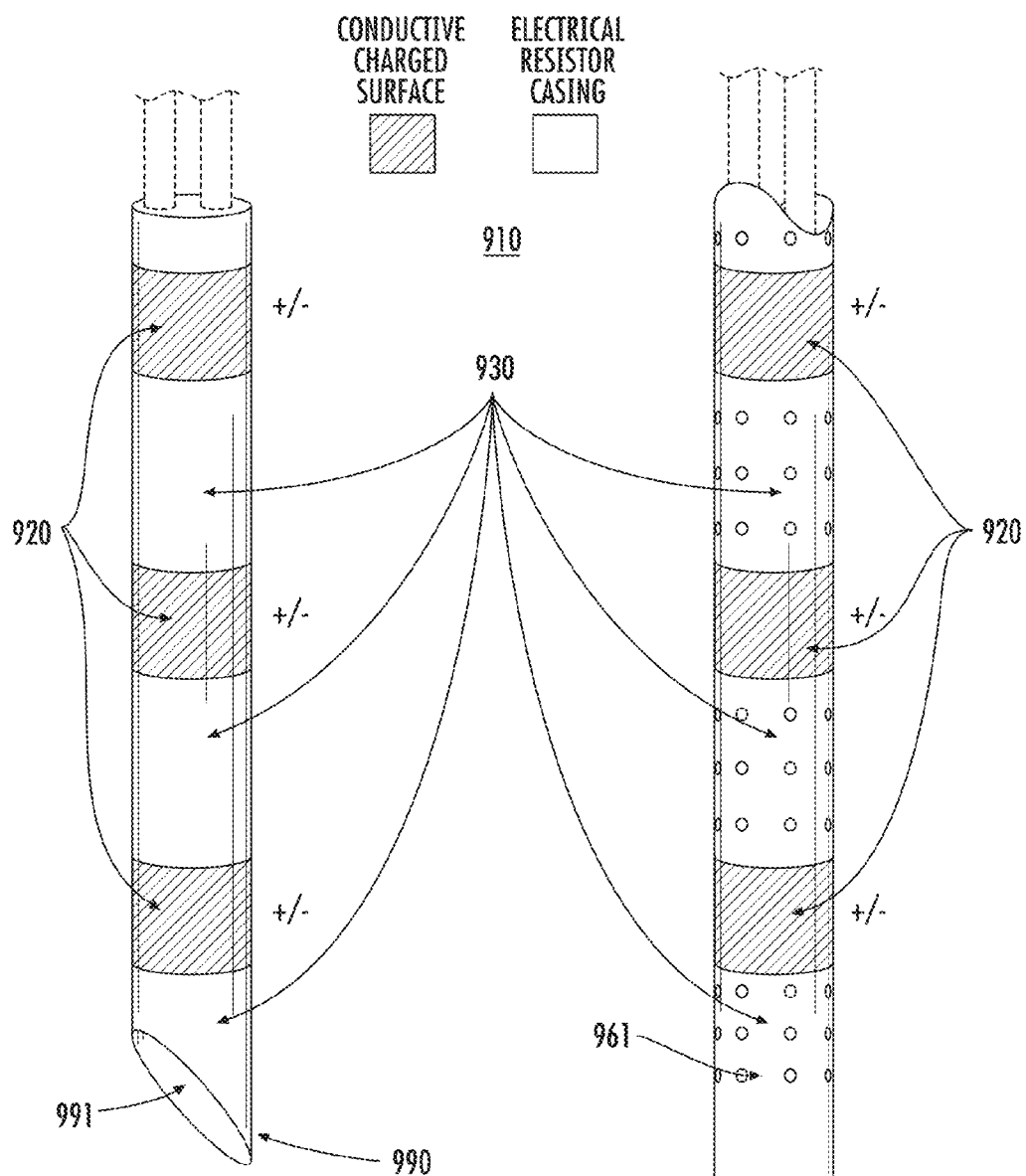
FIGS. 9A and 9B depict an embodiment of an assembled electrode tip for an exemplary treatment where the tip is inserted within a tumor embedded within benign tissue.

The schematics in FIGS. 9A-B show two basic hollow needle designs that may be implemented to enhance solution delivery prior to, during, or after IRE treatment. They both have multiple conducting surfaces 920 that may act as charged electrodes, grounded electrodes, or electric resistors, depending on the treatment protocol. FIG. 9A shows a hollow tip 910 for injection of agents at its end while FIG. 9B has distributed pores 961 throughout for a more generalized agent distribution. As shown in FIG. 9B, the pores are disposed in the non-conducting regions 930 of the device.

Example 5

Devices Comprising Active Cooling

In embodiments, the device comprises a cooling system within the electrode to reduce the highly localized temperature changes that occur from joule heating. During the electric pulses for IRE, the highest quantity of heat generation is at the electrode-tissue interface. By actively cooling (for example, via water flow) the electrode during the procedure, these effects are minimized. Further, cooling provides a heat sink for the nearby tissue, further reducing thermal effects. This allows more flexibility in treating larger tissue regions with IRE while keeping thermal effects negligible, providing a greater advantage for IRE over conventional thermal techniques. Cooling can be achieved by placement of one or more hollow chambers within the body of the device. The cooling chambers can be closed or open. Open chambers can be attached at the proximal end to fluid pumping elements to allow for circulation of the fluid (e.g., water) through the device during use.

Example 6

Movable Outer Sheath

Figure 10:
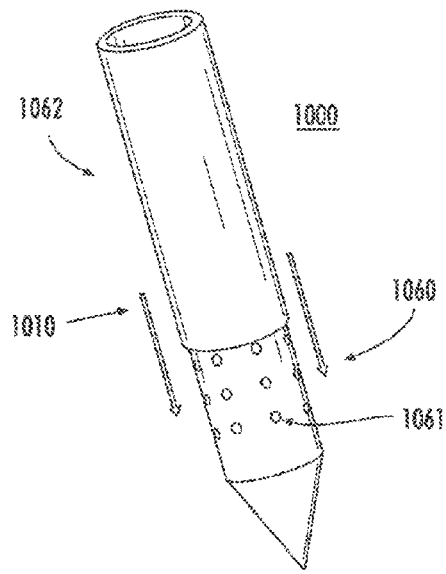
FIG. 10 depicts yet another embodiment of a device according to the invention, in which the outer, non-conductive sheath is adjustable to allow for selection of an appropriate depth/length of electrically conductive material to be exposed to tissue to be treated. The embodiment includes screw tappings (not shown) to allow real-time adjustment of the electrode layer lengths to customize electrode, dimensions prior to a procedure.

In embodiments, the device comprises an outer protector that is designed to be movable up and down along the length of the device. FIG. 10 depicts such a movable outer protector. More specifically, FIG. 10 depicts a device 1000 comprising tip 1010 that includes outer protector 1062 that can be moved up and down along the length of device 1000. In practice, outer protector 1062 is disposed fully or partially encasing outer sheath 1060. After or during insertion into tissue to be treated, outer protector 1062 is retracted partially to expose outer sheath 1060, which in the embodiment depicted comprises mixed dispersion outlets 1061. As such, the number of dispersion outlets 1061 exposed to the tissue during, treatment can be adjusted to deliver varying amounts of bioactive agent to different portions of the tissue being treated. Any mechanism for movement of the outer sheath along, the device may be used. In embodiments, screw threads are disposed on the upper portion of the device, allowing for easy adjustment by simple twisting of the outer sheath. Alternatively, set screws may be disposed in the outer sheath, allowing for locking of the sheath in place after adjustment.

Example 7

System for IRE Treatment of Tumors

Figure 11:
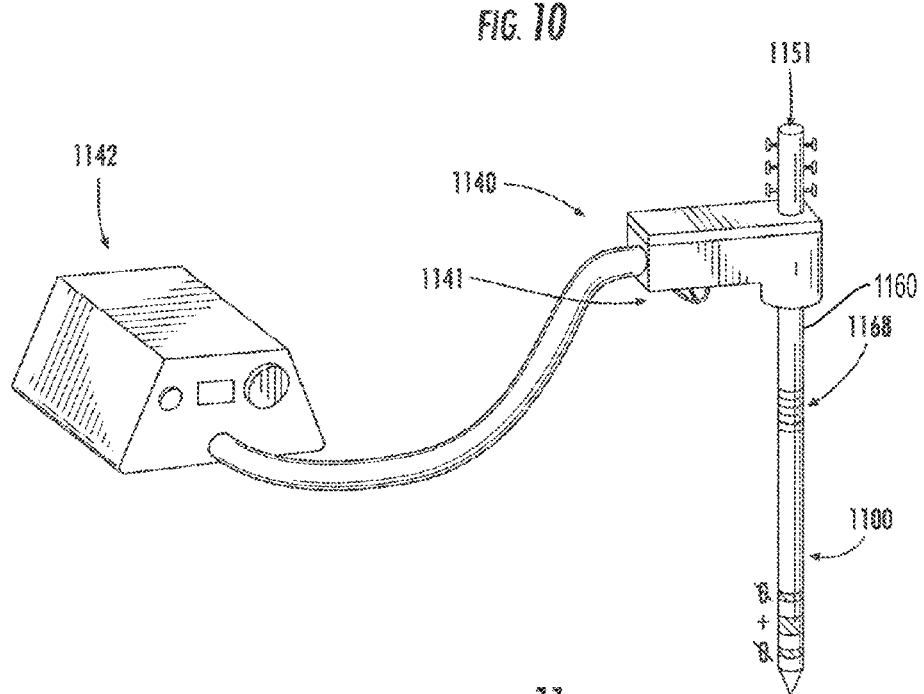
FIG. 11 depicts an exemplary system according to the invention, which includes an adjustable height electrode, a handle for physician guidance of the device into the patient, and a power source/controller to provide and control electrical pulses.

The invention provides a system for performing IRE tumor tissue ablation. As depicted in FIG. 11, an exemplary system can comprise a device 1100 reversibly attached to holder 1140. Holder 1140 can comprise trigger 1141, which allows the user to control the flow of electricity from power source/controller 1142 to device 1100.

In this embodiment, device 1100 comprises further elements for use. More specifically, device 1100 comprises a height adjustment apparatus 1151 at its proximal end to effect movement of outer sheath 1160. Outer sheath 1160 further comprises markings or scores 1168 on its surface to indicate amount of movement of outer sheath 1160 after implantation of device 1100 into tumor tissue.

Example 8

System for Controlling Multiple Electrodes

The invention provides a system for accurately controlling the distances between multiple electrodes of singular or multiple polarities during a charge. The device places electrode types within an adjustable part of a handle that may be maneuvered by a surgeon or attached to a harness system, as described above. The adjustable portion of the handle may be used to control the relative depths of penetration as well as separation distances of each electrode relative to one or more additional electrodes placed within the system.

Example 9

Modeling of Separation Distances Between Electrodes and Heat Generation

Figure 12E:
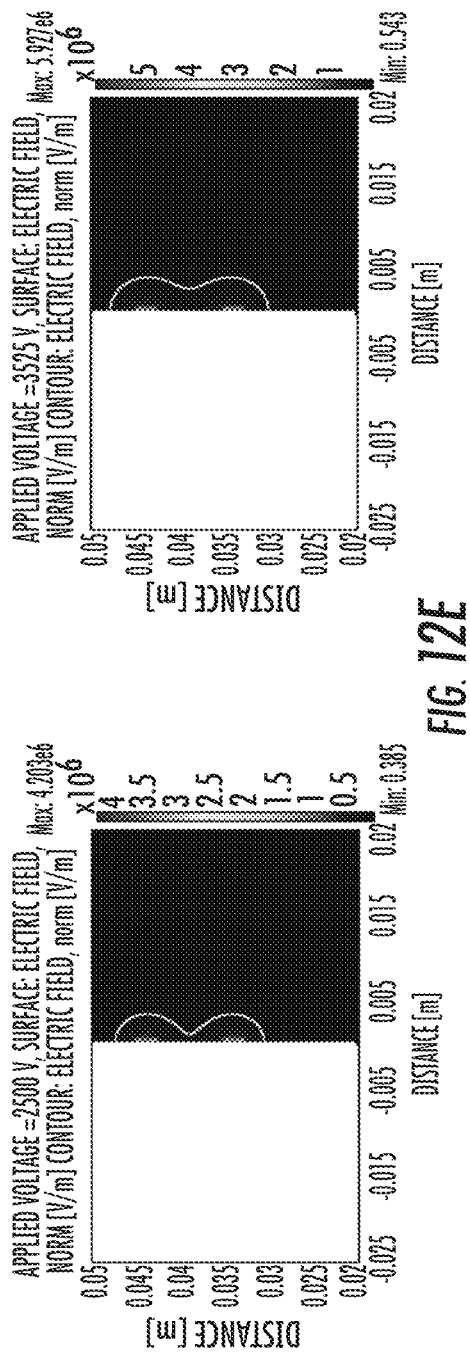

The system and method of the invention can include the use of multiple devices for treatment, of tumors. The devices can be implanted in the tumor at varying distances from each other to achieve desired cell killing. Alternatively, the system and method can include the use of a single device having multiple electrodes along its tip. Modeling of placement of multiple devices or a single device with multiple electrodes in tissue was performed, and exemplary electrical fields generated are depicted in FIGS. 12A-E. The outputs depicted in the figure demonstrate the variability in IRE treatment region that results from altering the separation distance of the conducting electrode surfaces. More specifically, FIGS. 12A-C show three model outputs for 2-dimensional needles (leftmost images) and an axis symmetric electrode (rightmost images). For all images, there were two charged surfaces, one of 2500V and one of 0V. The distances between the electrodes were 0.5 cm (FIG. 12A), 1.0 cm (FIG. 12B), and 1.5 cm (FIG. 12C). From this data, it is clear that altering the distance leads to significantly different electric field distributions, and thus makes the distance an important parameter to consider when developing IRE protocols for various tumor ablation.

Numerical models representing two needles and an axis symmetric needle electrode configuration have been developed, to compare the increase in treatment area shown by the electric field distribution for the same thermal, effects between 100 and 50 µs pulse lengths. The area/volume, of tissue that increased by at least 1 degree Kelvin was determined for a 100 µs pulse. This area/volume was then used for the 50 µs pulse to determine the electric field magnitude that would cause the same increase in temperature. A contour line has been created within these models to represent the region treated with the IRE threshold of 700 V/cm. The results are shown in FIG. 12D. More specifically, 2-D needle electrodes with 3.13 mm$^2$ area of tissue increased by one degree Kelvin for 100 µs pulse at 2500 V/c with 226.2 mm$^2$ area treated by IRE (FIG. 121D left side) and 50 µs pulse at 3525 V/cm with 325.6 mm$^2$ area affected by IRE (FIG. 120D right side). Axis symmetric needle electrode with 3.95 mm$^3$ volume of tissue increased by 1 degree Kelvin for 100 µs at 1500V with 81.1 mm$^3$ volume affected by IRE (FIG. 12E, left side) and 50 µs pulse at 2120V with a 133 mm$^3$ volume within IRE range (FIG. 12E, right side).

Example 10

Use of Different Tip Sizes

Figure 13A:
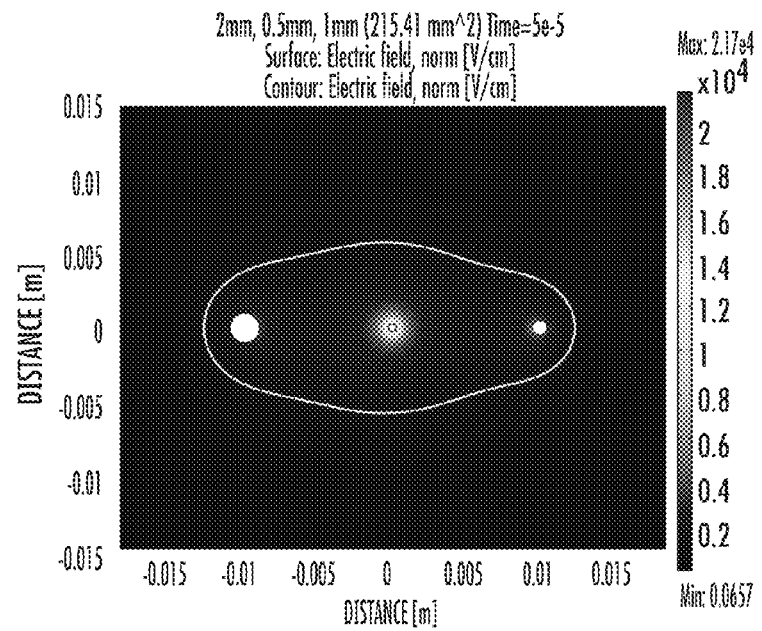
FIGS. 13A-13C depict electrical field outputs from various configurations employing three needle electrodes having, different diameters.
Figure 13B:
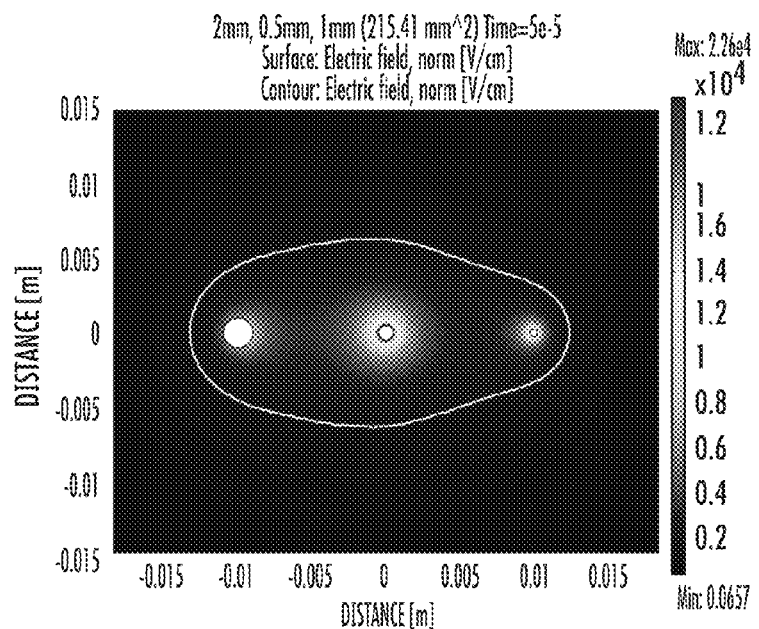
Figure 13C:
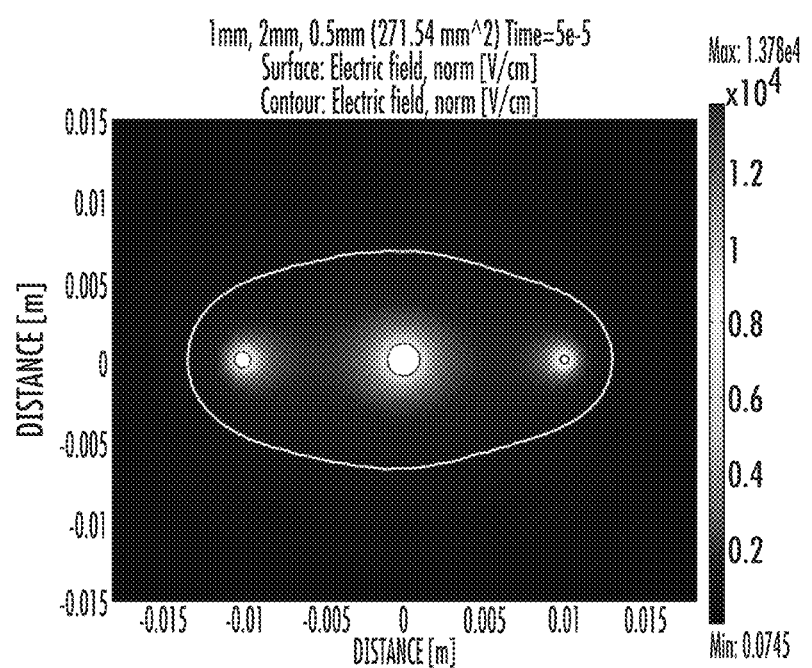

To provide exquisite control of electrical fields, and thus cell killing, the size of the electrode tips may be adjusted. In addition to real-time electrode manipulation capabilities, integrating multiple electrode types within the same procedure can make a large impact on enhancing electric field distribution selectivity. This can be done by incorporating such variations as a needle electrode with a single probe or parallel needle electrodes with the conductive surface of one being a different dimension (e.g., longer) than the other. As shown in FIGS. 13A-C, the electrical field output can be altered based on the arrangement of electrode types. More specifically, the figure shows model outputs displaying the electric field distribution for three needle electrodes, with a contour of 700 V/cm. It can be seen that by mixing up the diameter of the electrodes (as displayed with each figure) within the same treatment, the shape and area of tissue treated by the 700 V/cm threshold can be manipulated greatly. FIG. 13A shows the use of tips having, from left to right, 2 mm diameter, 0.5 mm diameter, and 1 mm diameter, providing a 700 V/cm threshold of 215.41 mm$^2$, FIG. 13B shows the use of tips having, from left to right, 1 mm diameter, 1 mm diameter, and 0.5 mm diameter, providing a 700 V/cm threshold of 243.26 mm$^2$. FIG. 13C shows the use of tips having, from left to right, 1 mm diameter, 2 mm diameter, and 0.5 min diameter, providing a 700 V/cm threshold of 271.54 mm$^2$.

Example 11

Use of Multiple Electrode Charges

Figure 14A:
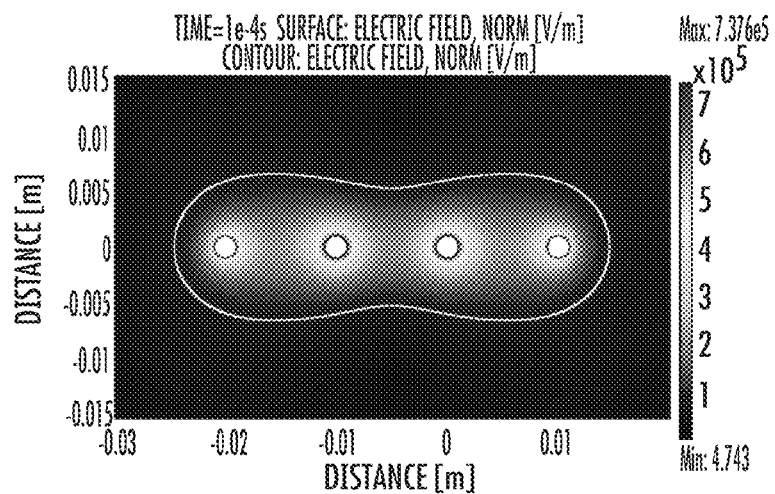
FIGS. 14A-14I depict electrical field outputs for various combinations of electrodes emitting different charges.
Figure 14B:
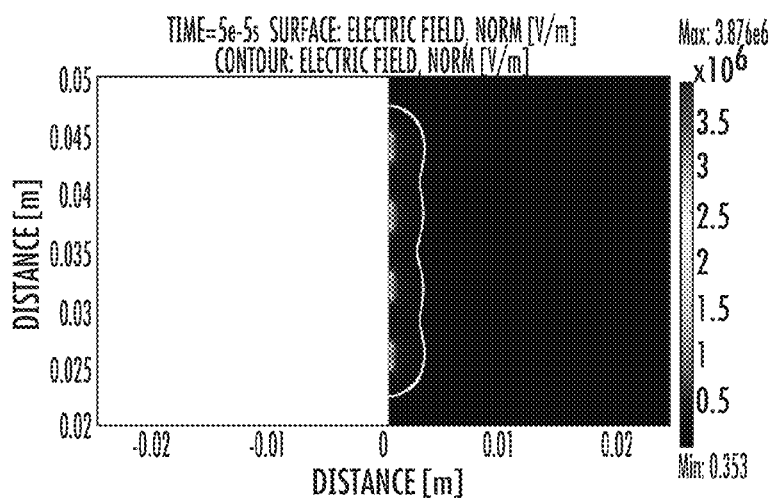
Figure 14C:
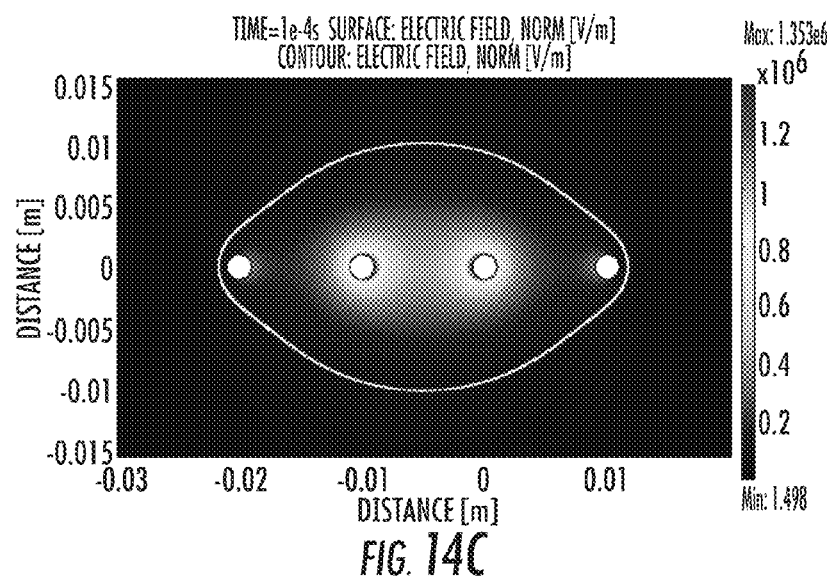
Figure 14D:
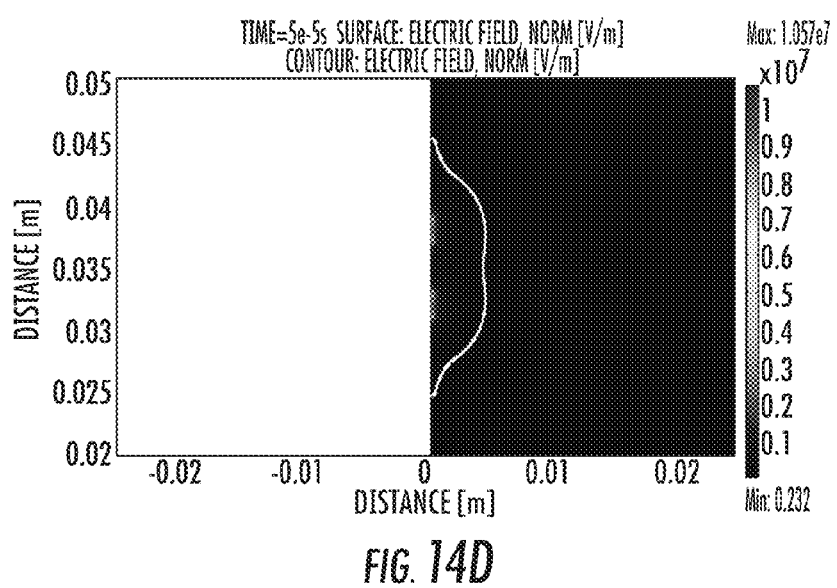
Figure 14E:
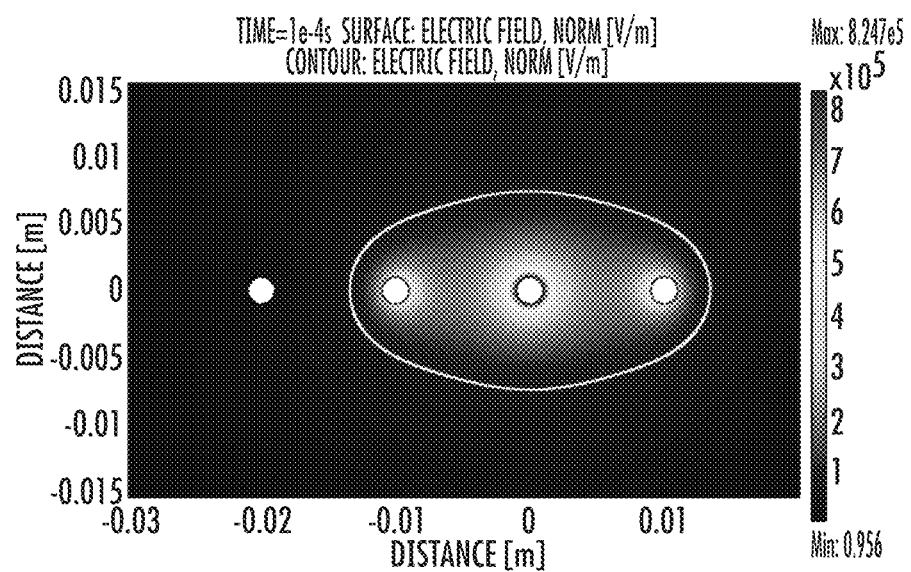
Figure 14F:
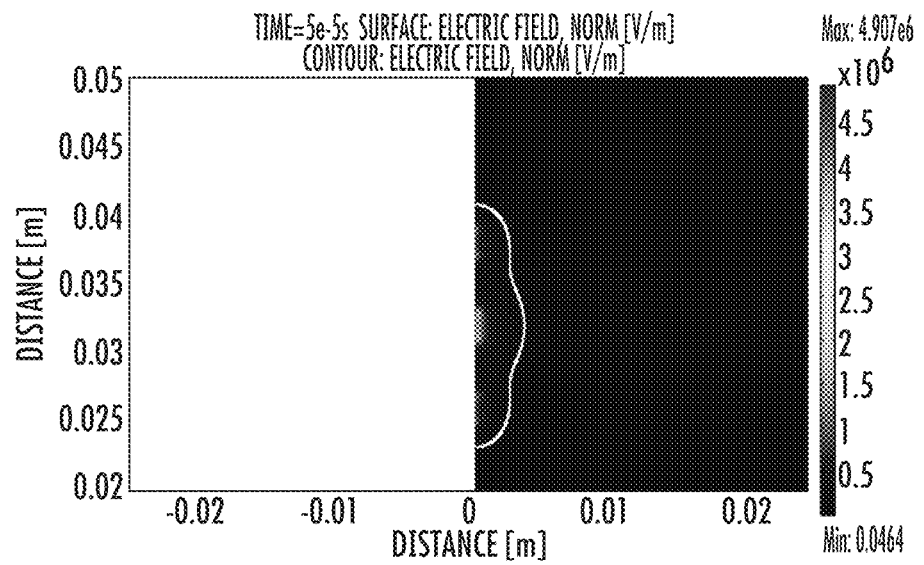
Figure 14G:
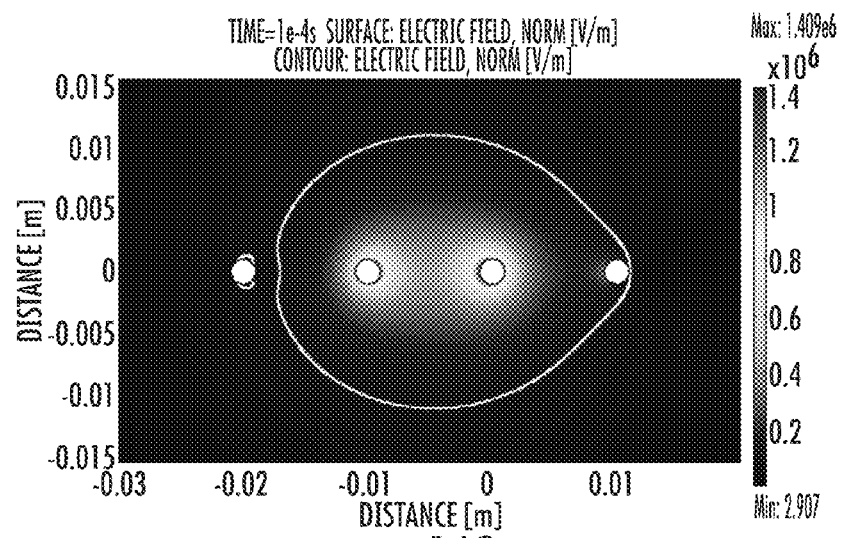
Figure 14H:
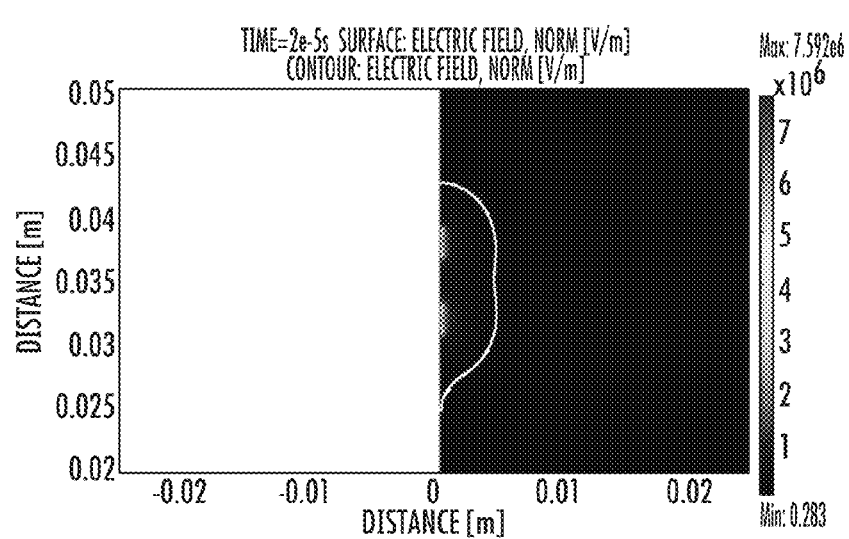
Figure 14I:
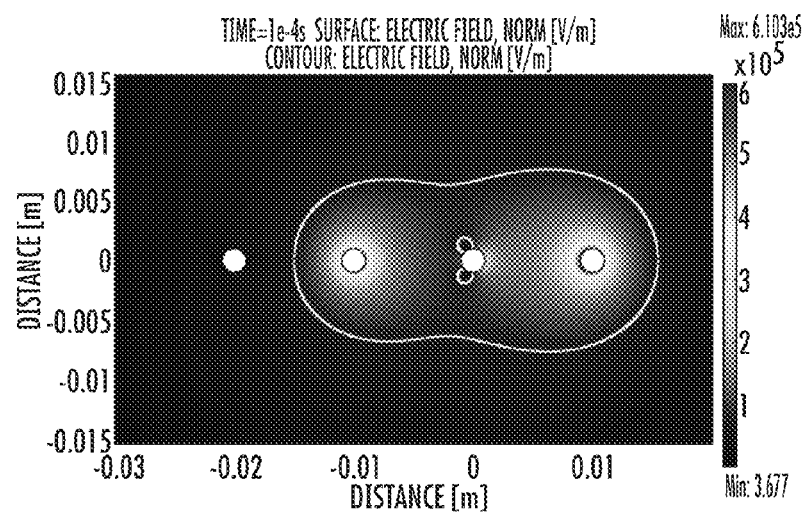
Figure 14J:
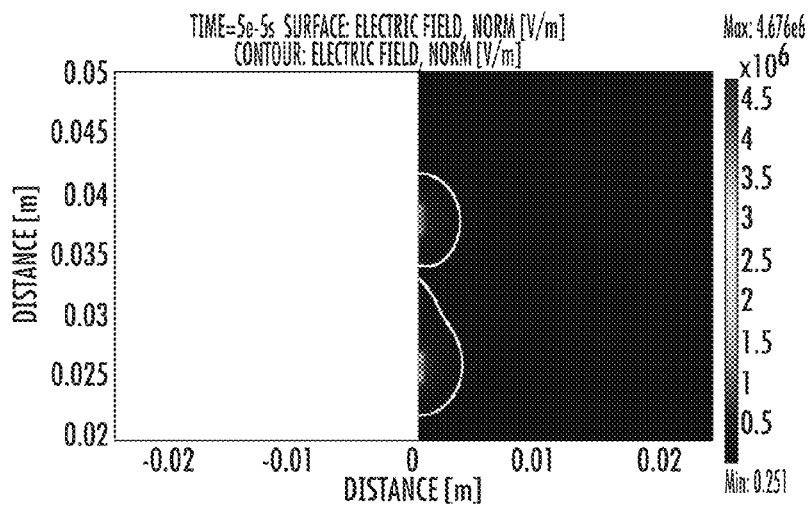
FIG. 14J depicts an axis symmetric display for the use of a similar electrode set up as FIG. 14I.

We have discovered that a highly customizable electric field distribution may be attained by combining multiple electrode charges within the same pulse. This allows a highly customized and controllable treatment protocol to match the dimensions of the target tissue. In addition, the invasiveness of the treatment may be decreased by reducing the number of electrode placements required for treatment. In order to demonstrate the great flexibility in electric field distribution shape, 2-dimensional and axis symmetric models were developed with 3 and 4 electrode arrays along a single axis. The results are depicted in FIGS. 14A-D. For development of the data, only the electric potentials of the electrodes were manipulated to achieve the great flexibility needed in IRE treatment planning. For FIGS. 14A-B, four charged electrodes of alternating polarity at 2500V and ground were used to develop a 2-D readout (FIG. 14A) and axis symmetric electrode configurations (FIG. 14B). Four charged electrodes with the center two at. 5000V and 0V and the outer two electrodes at 2500V were used to develop a 2-D readout (FIG. 14C) and axis symmetric electrode configurations (FIG. 14D). Three charged electrodes with the center one at 2500V and the outer two at 0V were used for 2-D (FIG. 14E) and axis symmetric electrode (FIG. 14F) configurations. Three charged electrodes with the center at 0V, left electrode at 5000V, and right electrode at 2500V for 2-D (FIG. 14G) and axis symmetric (FIG. 14H) scenarios. Three charged electrodes with the center at 1750V, left electrode at 3000V and right electrode at 0V for 2-D (FIG. 14I) and axis symmetric electrode (FIG. 14J) configurations.

Example 12

Thermal Effects for Long Duration Treatment

Figure 15A:
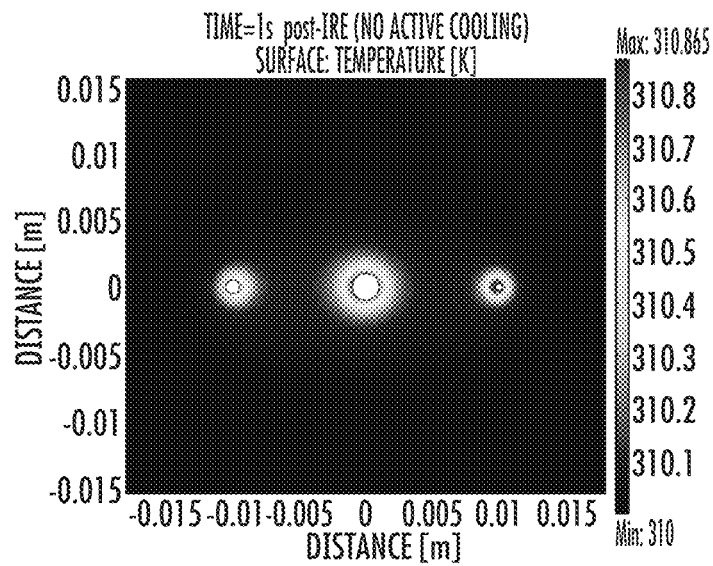
FIGS. 15A-15D depict thermal effects from use of three needle electrodes, with and without use of a cooling element in the electrode.
Figure 15B:
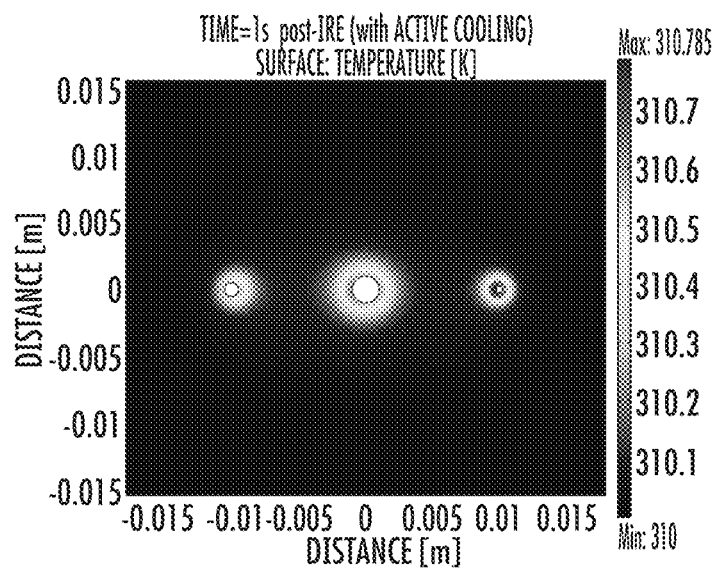
Figure 15C:
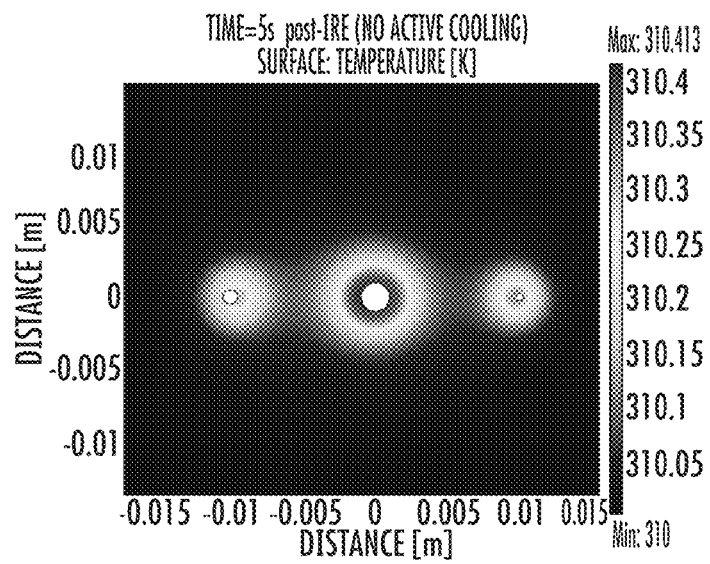
Figure 15D:
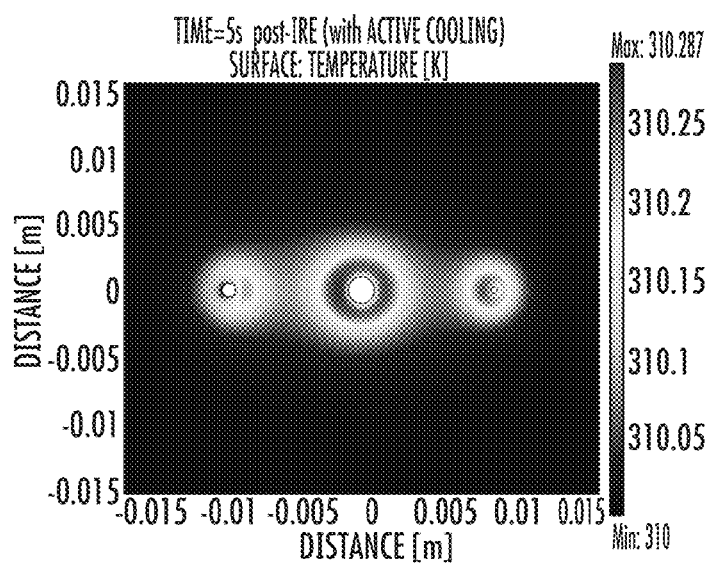

FIGS. 15A-D display the modeling outputs of thermal effects during a typical IRE treatment, but for extended treatment periods. The images in FIGS. 15A and 15C display the thermal effects without convective cooling, while the images in FIGS. 15B and 15D have the same treatment parameters, but incorporate convective cooling of the needle. FIGS. 15A and 15B: IRE treatment with 3 needles (1 second post-IRE) without (FIG. 15A) and with (FIG. 15B) convective cooling at the electrode-tissue interface. It can be seen, particularly on the large center electrode that the temperature of the tissue contacting the electrode is the region of highest temperature without cooling, but is actually a lower temperature than the peripheral regions of the tissue. FIGS. 15C and 15D: IRE treatment with 3 needles (5 seconds post-IRE) without (FIG. 15C) and with (FIG. 15D) convective cooling at the electrode-tissue interface. It can be seen, particularly on the large center electrode, that the temperature of the tissue contacting the electrode is the region of highest temperature without cooling, but is actually a lower temperature than the peripheral regions of the tissue.

Example 13

Altering the Diameter and Shape of Electrodes

Figure 16A:
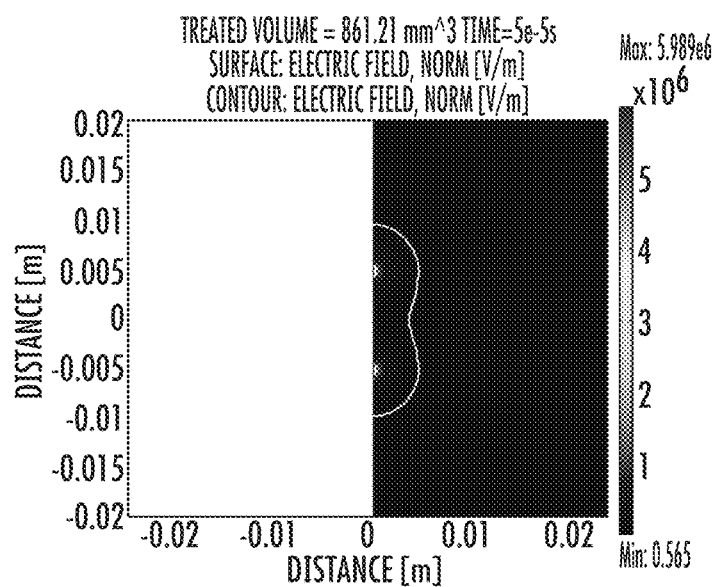
FIGS. 16A-16C depict thermal effects from use of two bipolar electrodes and an intervening balloon.
Figure 16B:
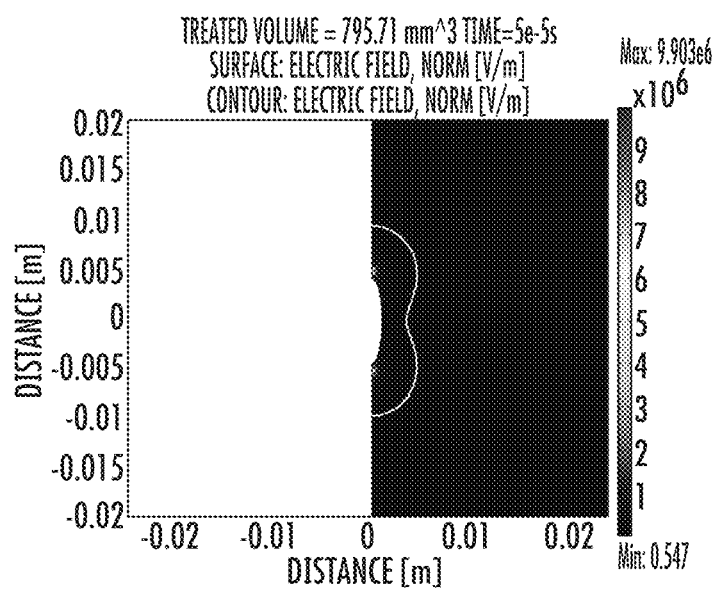
Figure 16C:
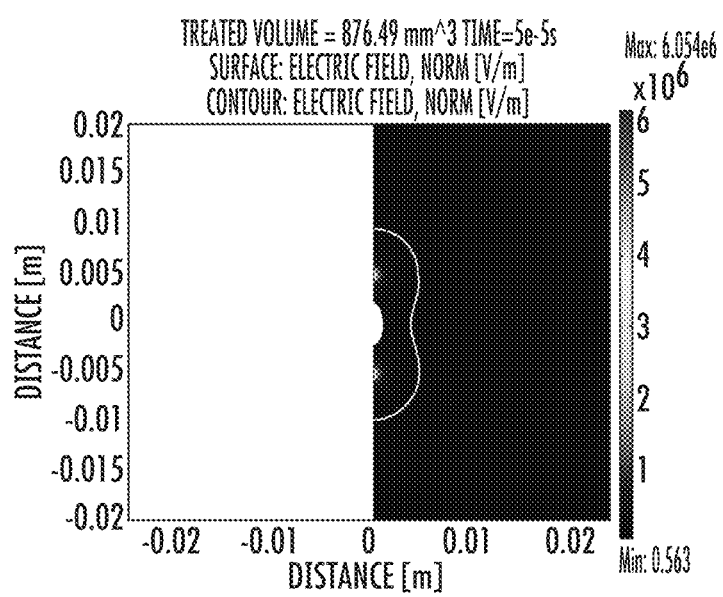

We have done some preliminary studies and determined that the electric field distribution may be altered, and thus controlled, by changing the diameter and shape of the electrode between the conducting surfaces. This fact can be used to design and develop an electrode with an expandable/contractible interior and deformable exterior to change its site in real-time before or during a treatment to alter, and thus specify the electric field distribution in a manner that may be desirable during treatment. The ability to adjust this dimension in real-time is made additionally useful by the fact that a significantly smaller electrode may be inserted to keep it minimally invasive, and then expand the dimension once the electrode has reached the target tissue. In embodiments, the invention includes the use of a balloon between regions of charge that may be inflated/deflated during treatment to alter field distribution. FIGS. 16A-C depict modeling of a bulging region between the charges in a bipolar electrode. Three different models that study the inclusion of a balloon between the two electrodes in a bipolar design are shown. FIG. 16A (861.21 mm³ treated area) has no balloon for comparison purposes. The middle design of FIG. 16B (795.71 mm³ treated area) has an elongated balloon that is in close proximity to the electrodes. The bottom design of FIG. 16C (846.79 mm³ treated area) has a smaller balloon that helps distribute the electric field.

Example 14

Alternating Polarity

With the application of electric potentials, electrical forces may drive ions towards one electrode or the other. This may also lead to undesirable behavior such as electrolysis, separating water into its hydrogen and oxygen components, and leading to the formation of bubbles at the electrode-tissue interface. These effects are further exacerbated for multiple pulse applications. Such effects may cause interference with treatment by skewing electric field distributions and altering treatment outcomes in a relatively unpredictable manner. By altering the polarity between the electrodes for each pulse, these effects can be significantly reduced, enhancing treatment predictability, and thus, outcome. This alternating polarity may be a change in potential direction for each pulse, or occur within each pulse itself (switch each electrode's polarity for every pulse or go immediately from positive to negative potential within the pulse at each electrode).

Example 15

Bipolar and Monopolar Electrodes

Using a bipolar electrode with 4 embedded electrodes, one can use the middle two electrodes to inject a sinusoidal current (~1-5 mA) that is low enough in magnitude to not generate electroporation and measure the voltage drop across the remaining two electrodes. From this setup one can calculate the impedance of the tissue and gather the conductivity of the tissue which is needed for treatment planning. One can do this analysis in a dynamic form after each electroporation pulse. Conductivity increases as a function of temperature and electroporation; therefore, for accurate treatment predictions and planning, the dynamic conductivity is needed and we can use the bipolar or unipolar electrodes to map the conductivity distribution before IRE treatment and during to adjust the pulse parameters.

Example 16

Parameters

The following are parameters that can be manipulated within the IRE treatments discussed herein.
Pulse length: 5 ∞s-1 ms
Number of pulses: 1-10,000 pulses
Electric Field Distribution: 50-5,000 V/m
Frequency of Pulse Application: 0.001-100 Hz
Frequency of pulse signal: 0-100 MHz
Pulse shape: square, exponential decay, sawtooth, sinusoidal, alternating polarity
Positive, negative, and neutral electrode charge pulses (changing polarity within probe)
Multiple sets of pulse parameters for a single treatment (changing any of the above parameters within the same treatment to specialize outcome)
Electrode Type
Parallel plate: 0.1 mm-10 cm diameter
Needle electrode(s): 0.001 mm-1 cm diameter
Single probe with embedded disk electrodes: 0.001 mm-1 cm diameter
Spherical electrodes: 0.0001 mm-1 cm diameter
Needle diameter: 0.001 mm-1 cm
Electrode length (needle): 0.1 mm to 30 cm
Electrode separation: 0.1 mm to 5 cm Example 17

Specific Conductivity

The methods used to model tissue ablation are similar to the ones described by Edd and Davalos for predicting IRE areas based on the electric field and temperature distribution in the tissue (Edd, J. F., et al., 2007, "Mathematical modeling of irreversible electroporation for treatment planning.". Technology in Cancer Research and Treatment., 6:275-286.) The methods are disclosed in Garcia et al., "Irreversible electroporation (IRE) to treat brain cancer," ASME Summer Bioengineering Conference, Marco Island, Fla., Jun. 25-29, 2008.

We have modeled a new electrode design for the application of IRE in brain tissue. According to our results, IRE can be an effective technique for minimally invasive brain tumor removal. The treatment does not induce substantial thermal effects in the brain, protecting the integrity of this organ, which is susceptible to small fluctuations in temperature. In an embodiment of the method of the invention, the method includes delivering electrical signal(s) through tissue to determine its electrical properties before administering IRE by monitoring the voltage and current. Following from that, one may apply intermittent and post-IRE pulse(s), which can be used to determine the success of the procedure and adjust IRE pulse parameters.

Specific conductivity can be important for treatment planning of irreversible electroporation (IRE). For many applications, especially when treating tumors in the brain, the volume (area) of IRE must be predicted to maximize the ablation of the tumorous tissue while minimizing the damage to surrounding healthy tissue. The specific electrical conductivity of tissue during an irreversible electroporation (IRE) procedure allows the physicians to: determine the current threshold; minimize the electric current dose; decrease the Joule heating; and reduce damage to surrounding healthy tissue. To measure the specific conductivity of tissue prior to an IRE procedure the physician must: establish the electrode geometry (shape factor); determine the physical dimensions of the tissue; apply a small excitation AC voltage signal (1 to 10 mV); measure the AC current response; calculate the specific conductivity (n) using results from the prior steps. This procedure will not generate tissue damage (low amplitude AC signals) and will supply the physician (software) with the required information to optimize IRE treatment planning, especially in sensitive organs like the brain which is susceptible to high electrical currents and temperatures. Thus, the IRE procedure is well monitored and can also serve as a feedback system in between series of pulses and even after the treatment to evaluate the area of ablation.

Special Cases for electrode geometry:
Nomenclature (units in brackets):
$V_e$=voltage on the hot electrode (the highest voltage), [V]
$R_1$=radius of electrode with highest voltage (inner radius), [m]
$R_2$=radius at which the outer electrodes are arranged (outer radius), [m]
i=total current, [A]
L=length of cylindrical electrode, [m]
σ=electrical conductivity of tissue, [S/m]

Electrical conduction between a two-cylinder (needle) arrangement of length L in an infinite medium (tissue). It is important to note that this formulation is most accurate when L>>$R_1$, $T_2$ and L>>w. The electrical conductivity cm be calculated from, $$\sigma = \frac{i \cdot S}{V_e}$$

where the shape factor (S) corresponding to the electrode dimensions and configuration is given by, $$\frac{2 \cdot \pi \cdot L}{\cosh^{-1}\left(\frac{4 \cdot w^2 - (2 \cdot R_1)^2 - (2 \cdot R_2)^2}{8 \cdot R_1 \cdot R_2}\right)}$$

The specific conductivity (σ) of the tissue can be calculated since the voltage signal ($V_e$) and the current responses (i) are known.

Explanation of electrical concepts: By using the bipolar electrode described in the priority document, one can apply, a small excitation AC voltage signal (1 to 10 mV), $$V(t)=V_0 \operatorname{Sin}(\_t)$$

where V(t) is the potential at time t, $V_0$ is the amplitude of the excitation signal and _ is the frequency in radians/s. The reason for using a small excitation signal is to get a response that is pseudo-linear since in this manner we can determine the value for the impedance indicating the ability of a system (tissue) to resist the flow of electrical current. The measured AC current (response) that is generated by the excitation signal is described by $$I(t)=I_0 \operatorname{Sin}(\_t+\_)$$

where I(t) is the response signal, $I_0$ is the amplitude of the response ($I_0$ $V_0$) and _ is the phase shift of the signal. The impedance (Z) of the system (tissue) is described by, $$Z(V(t))/(I(t))=(V_0 \operatorname{Sin}(\_t))/(I_0 \operatorname{Sin}(\_t+\_))=Z_0(\operatorname{Sin}(\_t))/(\operatorname{Sin}(\_t+\_))$$

It is important to note that the measurement of the response is at the same excitation frequency as the AC voltage signal to prevent interfering signals that could compromise the results. The magnitude of the impedance |$z_e$| is the electrical resistance of the tissue. The electrical resistivity (_m) can be determined from the resistance and the physical dimensions of the tissue in addition to the electrode geometry (shape factor). The reciprocal of the electrical resistivity is the electrical conductivity (S/m). Therefore, after deriving the electrical resistivity from the methods described above, the conductivity may be determined.

Example 18

Use of Nanoparticles in IRE

Despite its mechanism of action, a major disadvantage of IRE in terms of cancer treatment is that the pulsing protocol cannot distinguish between healthy cells and tumor cells. Additionally, the voltage that is applied during treatment is limited to the maximum voltage that can be delivered to the tissue without inducing Joule heating. Joule heating can lead to disruption of the extracellular matrix, nerve damage, and coagulation of the macrovasculature, which are undesirable treatment outcomes. This invention simultaneously addresses both of these deficiencies through the incorporation of particles, and preferably nanoparticles or microparticles of very small size, into pulsed electric field therapies. This Example provides data showing that the use of small microparticles and nanoparticles in IRE can increase treatment area without the need to increase the applied voltage, which would result in thermal damage.

The electric field to which a cell is exposed determines whether or not it will undergo IRE or supra-poration. The typical electric field threshold, which varies as a function of the cell type and pulsing parameters (frequency, duration, and number), is roughly 600 V/cm for IRE. If nanoparticles raise the electric field above the threshold for IRE, they can be incorporated into pulsed electric field therapies to expand the treatment area or to lower the necessary applied voltage to induce IRE, which reduces the extent of thermal damage. Conducting, semi-conducting, and insulating nanoparticles can be used to enhance the electric field. The permittivity of the nanoparticles is not a significant contributing factor to the calculated electric field distribution when the frequency of the applied field is below 1 MHz. For materials with a conductivity ratio below 1, a sphere or rod-shaped nanoparticle oriented perpendicular to the applied field should be employed, and for materials with a conductivity ratio above 1, a sphere or rod-shaped nanoparticle oriented parallel to the applied field should be employed. See, for example, FIG. 18.

Figure 21:
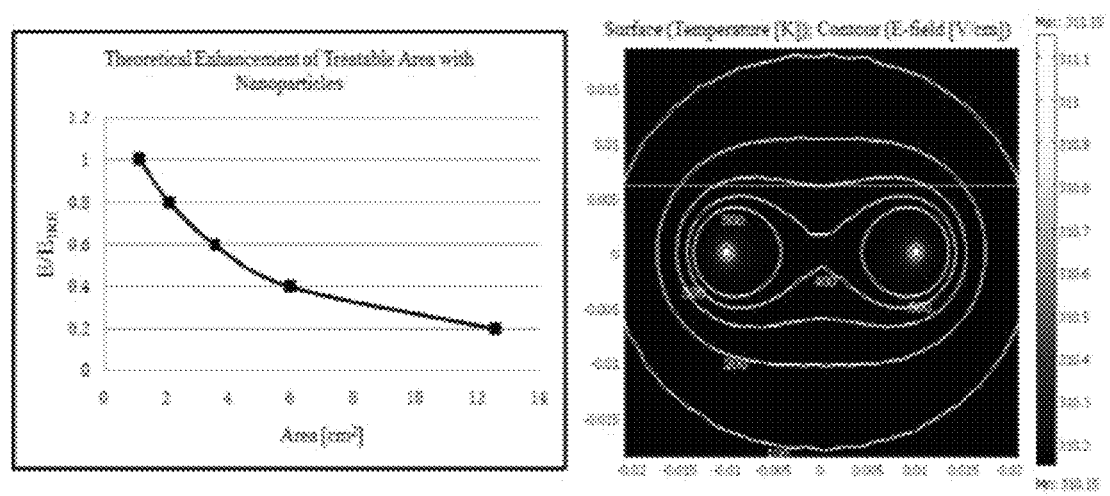
FIG. 21 depicts the results of a finite-element model, for predicting the treatment area resulting from an IRE procedure using 2 needle electrodes. The leftmost graph of FIG. 21 shows the resulting electric field distribution (contour) and temperature rise (surface). The rightmost image of FIG. 21 shows a ratio of the electric field within the tissue to the electric field threshold for IRE (500 V/Cm as determined experimentally) versus the area encompassed by the electric field within the tissue.

An assessment of the treatment area enhancement following IRE with the inclusion of nanoparticles is shown in FIG. 21. The developed two-dimensional finite-element model represents two parallel needle electrodes (1 mm in diameter separated by a distance of 2 cm) inserted within a tumor. It is assumed that the tumor was initially at physiologic temperature (310.15 K), and the simulation was run for a single, 50 μs pulse with an applied voltage of 1500 V set along the boundary of one of the electrodes with the other set as ground. The results indicate that if nanoparticles delivered to the tumor can amplify the electric field by a factor of 2 such that an area that was previously at 250 V/cm meets an electric field threshold of IRE (taken in this example to be 500 V/cm), then the treatable area will be increased by a factor of 4. Further, the predicted temperature rise of 1 K is far less than that required to induce thermal damage from the denaturation of proteins. As mentioned, by expand me the treated area without increasing the voltage applied through the electrodes, we will be able to treat infiltrative cancer cells beyond the tumor margin for preventing tumor recurrence and metastasis without inducing thermal damage.

Figure 19:
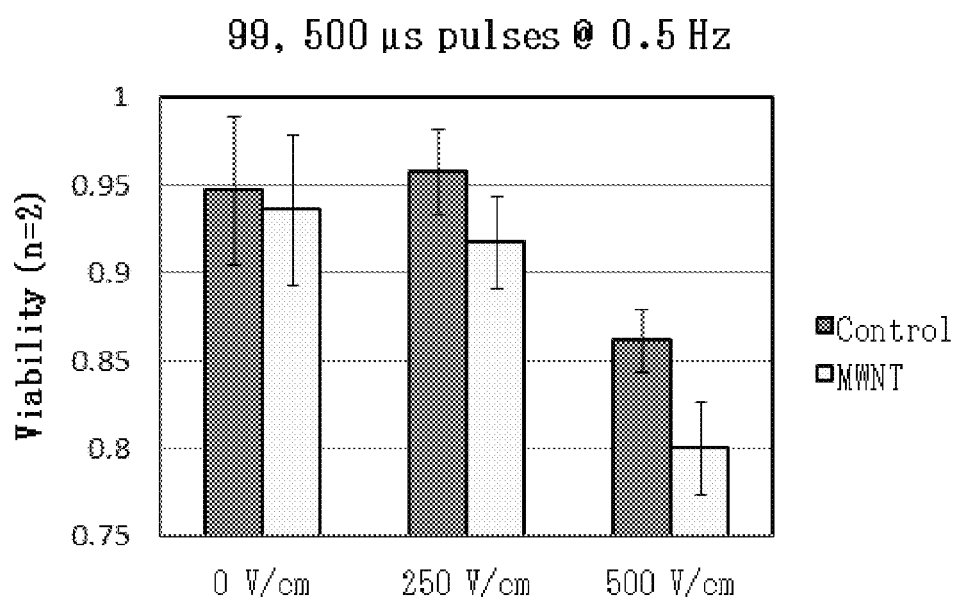
FIG. 19 depicts a bar graph showing the effect of electric field strength on cell viability following IRE treatment with and without nanoparticles.

FIG. 19 depicts a bar graph showing cell viability as a function of electric field for 99, 500 μs pulses delivered at a frequency of 0.5 Hz with a voltage ranging from 0-100 V (across 2 mm gap electrode). More specifically, the experimental evidence shown in FIG. 19 shows the ability of multi-walled carbon nanotubes to lower the electric field threshold for IRE. Human metastatic breast cancer cells (MDA-MB-231) were treated in vitro and in suspension with and without the inclusion of nanotubes. Nanotubes (0.5 mg/ml) were suspended in DEP buffer (8.5% sucrose [weight/volume], 0.3% glucose [weight/volume], and 0.725% RPMI [volume/volume]) supplemented with Plusonie 108 NF (BASF) for uniform dispersion, and cells were resuspended directly in this solution. Following treatment, cell viability was assessed through a nypan blue dye exclusion assay. Trypan blue was used to stain cells with a compromised plasma membrane, while viable cells remained unstained. Cells were counted conventionally on a hemacytometer with two trials per treatment group (n=2). The results indicate that multi-walled nanotubes caused enhanced cell death in an applied electric field of 500 V/cm, whereas cells treated with the same pulsing parameters without the inclusion of nanotubes remain significantly more viable.

Figure 20:
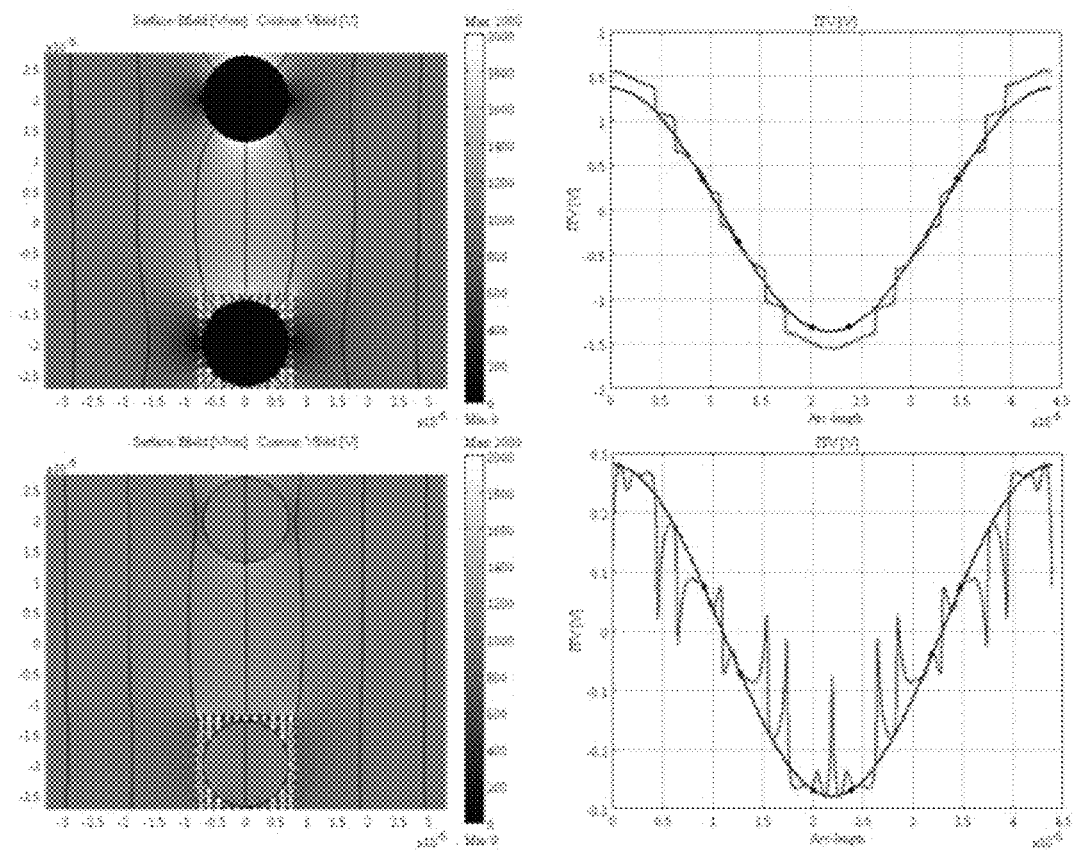
FIG. 20 depicts the results of a finite-element model showing the effect of polystyrene particles on delivery of electrical energy to a cell. A cell (14 μm diameter) with and without surrounding polystyrene beads (1 μm diameter) in a 1000 V/cm uniform DC electric field (upper left image) and a 1 MHz AC electric field (lower left image). The surface color map represents the electric field (V/cm), and the contours represent the electric potential (V). The induced transmembrane voltage (ITV) traced clockwise around a cell (14 μm diameter) with (wavy line trace) and without (smooth line trace) surrounding polystyrene heads (1 μm diameter) in a 1000 V/cm uniform DC electric field (upper right graph) and a 1 MHz AC electric field (lower right graph).

Computational FEMs for predicting the transmembrane potential across cells placed in a uniform elecuic field indicate that the inclusion of micro- and nanospheres can have a significant impact in terms of altering the induced transmembrane potential (ITV). More specifically, the data m FIG. 20 show that when polystyrene beads (1 um diameter) are inserted around one half of a cell (14 um diameter) in a 1000 V/cm uniform DC and 1 MHz AC electric field, an enhanced electrical field is created. When the applied pulses are DC, this electric field enhancement can alter the ITV and make the cell more susceptible to IRE. However, when the frequency of the applied field is larger than the inverse of the relaxation time of the cell (typically around one microsecond), the transmembrane potential is inversely proportional to the frequency. Therefore, at 1 MHz, the transmembrane potential does not reach values above 1 V, which are required for IRE. The enhanced cell death is presumably due to the localized electric field enhancement around the microspheres. Because the microspheres are insulators, they maintain their charged dipole orientation even in high frequency fields. In these simulations, the cell membrane boundary is treated as a distributed impedance, while the microsphere membranes are treated as continuous.

Example 19

Use of IRE and Nanoparticles with Modified Surface Chemistry

IRE has been shown to promote tumor regression. However, it cannot selectively kill cancer cells within a tumor mass without also killing healthy cells. The selectivity of pulsed electric field therapies can be enhanced through the use of nanoparticles. The surface of nanoparticles can be functionalized to target specific cancer cells with various antibodies and chemical compounds. Due to the ability of certain nanoparticles to enhance the electric field, and the ability of functionalized nanoparticles to target cancer cells, electric pulse protocols can be optimized such that only cancer cells with selectively bound nanoparticles experience a localized electric field above the threshold for achieving IRE, and healthy cells remain intact. The concept of use of functionalized surfaces for IRE is provided in FIG. 17, in the context of functionalizing an electrode tip. The same concept and general chemistry can be used to functionalize nanoparticles to create a specific association of the nanoparticles with target cells. This methodology can be employed to purge the body of cancer cells within and beyond the treatment margin, while maintaining proper organ function. Tumors can be up to 80% healthy cells, and selectively destroying the cancer cells, including cancer stern cells (CSCs), reduces the potential for tumor recurrence.

For example, CNTs may be injected into a region of tissue, with or without targeting antibodies, to mediate IRE for tumor ablation. CNTs may be injected directly into the tumor and CNTs with targeting antibodies may be introduced by intraperitoneal injection, a route that has been shown to produce good bio-distribution and tumor targeting. CNTs may be targeted to tumor cells via antibodies to the folate receptor to permit localized CNT mediated electric field amplification at selected tumor cell membranes causing targeted cell death.

Nanotube Selectivity: Selective destruction of tumor cells with CNT-mediated N-TIRE therapy is dependent upon targeting CNTs to the tumor cells of interest. In physiological conditions, cells uptake folic acid across the plasma membrane using the folate carrier to supply the folate requirements of most normal cells. In contrast, folate receptor (FR), a high affinity membrane folate-binding protein, is frequently overexpressed in a wide variety of cancer cells. Since it is generally either absent or present at only low levels in most normal cells, the FR has been identified as not only a marker of cancers but also a potential and attractive target for tumor specific drug delivery. Nanoparticles conjugated with folic acid (FA-NP) may be synthesized to evaluate the efficiency of targeted delivery of bioconjugated nanoparticles into cancer cells.

The cellular binding/uptake assay of the folate-conjugated nanoparticles using fluorescence microscopy has been established. FR-overexpressing cancer cells (KB) were incubated with nanoparticles conjugated with FITC and folic acid (FA-NP-FITC) as well as with control nanoparticles (FITC-NP) for 4 h at 37° C. The cells were then stained with Concanavalin A AlexaFluor 594 and the slides were examined on a Zeiss AXIO Imager Al m fluorescence microscope (Carl Zeiss MicroImaging, Inc., Thornwood, N.Y.). Images were acquired by AxioCam MRc5 Digital Imaging System. The images show green fluorescence of specifically bound/up-taken FA-NP-FITC was visible on the red-stained KB cells while only weak, non-specific green fluorescence was observed in cells incubated with FITC-NP. This technique can be utilized to examine the specific targeting ability of CNTs.

Example 20

Use of IRE with Nanoparticles Incorporating Drugs for Cancer Treatment

A portion of the treatment area that does not experience an electric field above the threshold for IRE still undergoes reversible electroporation. Therefore, microspheres and nanospheres can be used as carriers to get drugs, such as chemotherapeutic agents, into cells through reversible electroporation. Under normal conditions, these drugs would not be able to permeate the plasma membrane. Additionally, the pulsing parameters can be tuned to electrophoretically drive the microspheres or nanospheres loaded with drugs through the reversible pores. This addition to conventional IRE therapy can help to further reduce tumor recurrence.

It will be apparent to those skilled in the art that various modifications and variations can be made in the practice of the present invention without departing from the scope or spirit of the invention. Other embodiments of the invention will be apparent to those skilled in the art from consideration of the specification and practice of the invention. It is intended that the specification and examples be considered as exemplary only, with a true scope and spirit of the invention being indicated b the following claims.

The invention claimed is:

1. A method of treating a subject having a neoplasia, the method comprising:
    identifying a treatment area in the subject, wherein the treatment area comprises the neoplasia;
    providing nanoparticles modified to selectively bind to neoplastic cells of the neoplasia;
    administering the nanoparticles to the treatment area in an amount sufficient to permit at least some of the nanoparticles to bind to the neoplastic cells;
    positioning at least one electrode into or adjacent to the neoplastic cells; and
    applying an electric field to the treatment area by delivering electrical pulses from the at least one electrode to irreversibly electroporate the neoplastic cells.

2. The method of claim 1, wherein the nanoparticles comprise folic acid conjugations.

3. The method of claim 1, wherein the nanoparticles comprise antibody conjugations.

4. The method of claim 1, wherein the nanoparticles comprise a polymer coating.

5. The method of claim 1 further comprising:
    identifying the neoplasia presented as any one of: a leukemia, a non-solid tumor, a solid tumor, and tumors in the brain, bone marrow, liver, prostate, kidney, breast, and pancreas.

6. The method of claim 1, wherein the subject is a human.

7. The method of claim 1 further comprising:
    positioning a second electrode into Or adjacent to the neoplastic cells, and applying an electric field to the neoplastic cells by delivering electrical pulses from the second electrode to irreversibly electroporate the neoplastic cells.

8. The method of claim 1 further comprising:
    limiting, the electric field, to minimize disruption of or damage to healthy tissue surrounding the neoplastic cells.

9. The method of claim 1 further comprising:
    amplifying the electric field to lower the threshold required for inducing irreversible electroporation and enlarging the treatment area.

10. The method of claim 1, wherein the step of administering nanoparticles further comprises administering nanoparticles selected from the group comprising spherical nanoparticles, rod-shaped nanoparticles, fullerenes, endohedral metallofullerenes (EMFs), trimetallic nitride template endohedral metallofullerenes (TNT EMFs), single-walled and multi-walled carbon nanotubes, gold nanorods, silver nanorods, single-walled and multi-walled boron/nitride nanotubes, carbon nanotube peapods, carbon nanohorns, carbon nanohorn peapods, liposomes, nanoshells, dendrimers, quantum dots, superparamagnetic nanoparticles, nanorods, polystyrene beads, glass and polymer micro- and nano-spheres, biodegradable micro- and nano-spheres, glass nanospheres, polystyrene particles, polymer nanospheres, gold nanoparticles, silver nanoparticles, carbon nanoparticles, iron nanoparticles, conducting nanoparticles, semi-conducting nanoparticles, cellulose nanoparticles, and insulating nanoparticles, or a combination of two or more of these.

11. The method of claim 1 further comprising:
    positioning the nanoparticles such that the particles are parallel or perpendicular to the applied electric field.

12. The method of claim 1 further comprising:
    administering the nanoparticles after the step of delivering electrical pulses.

13. A method of treating a subject having a neoplasia, the method comprising:
    identifying in the subject a treatment area containing the neoplasia;
    administering to the treatment area a plurality of nanoparticles that have been functionalized to selectively target neoplastic cells of the neoplasia such that at least some of the nanoparticles bind to the neoplastic cells;
    positioning at least one electrode into or adjacent) the neoplastic cells; and
    applying through the at least one electrode a plurality of electrical pulses to the treatment area that have been administered with the functionalized nanoparticles to kill the neoplastic cells.

14. The method of claim 13, wherein the nanoparticles comprise folic acid conjugations.

15. The method of claim 13, wherein the nanoparticles comprise antibody conjugations.

16. The method of claim 13, wherein the nanoparticles comprise a polymer coating.

* * * * *